US009045416B2

(12) United States Patent
Lum et al.

(10) Patent No.: US 9,045,416 B2
(45) Date of Patent: Jun. 2, 2015

(54) WNT PROTEIN SIGNALLING INHIBITORS

(71) Applicant: THE BOARD OF REGENTS OF THE UNIVERSITY OF TEXAS SYSTEM, Austin, TX (US)

(72) Inventors: Lawrence Lum, Dallas, TX (US); Michael G. Roth, Dallas, TX (US); Baozhi Chen, Addison, TX (US); Chuo Chen, Dallas, TX (US); Michael E. Dodge, Irving, TX (US); Wei Tang, Beijing (CN)

(73) Assignee: The Board of Regents of the University of Texas System, Austin, TX (US)

( * ) Notice: Subject to any disclaimer, the term of this patent is extended or adjusted under 35 U.S.C. 154(b) by 189 days.

(21) Appl. No.: 13/875,170

(22) Filed: May 1, 2013

(65) Prior Publication Data
US 2014/0038922 A1 Feb. 6, 2014

Related U.S. Application Data

(62) Division of application No. 12/994,661, filed as application No. PCT/US2009/045340 on May 27, 2009, now Pat. No. 8,445,491.

(60) Provisional application No. 61/130,149, filed on May 27, 2008, provisional application No. 61/204,279, filed on Jan. 2, 2009.

(51) Int. Cl.
*C07D 209/94* (2006.01)
*C07D 239/54* (2006.01)
(Continued)

(52) U.S. Cl.
CPC ............ *C07D 209/48* (2013.01); *C07D 209/94* (2013.01); *C07D 239/54* (2013.01); *C07D 401/12* (2013.01); *C07D 401/14* (2013.01);
(Continued)

(58) Field of Classification Search
CPC .. C07D 209/48; C07D 209/94; C07D 239/54; C07D 401/10; C07D 401/12; C07D 401/14; C07D 403/10; C07D 413/04; C07D 417/12; C07D 471/04; C07D 519/00
USPC ................ 514/248, 314, 411, 259.41, 266.3, 514/260.1, 7.9, 9.8, 19.3; 435/375, 383; 544/283; 548/435
See application file for complete search history.

(56) References Cited

U.S. PATENT DOCUMENTS 6,897,220 B2   5/2005   Delorme et al.

FOREIGN PATENT DOCUMENTS

| WO | WO 02/44378 | 6/2002 |
| WO | WO 02/064080 | 8/2002 |

(Continued)

OTHER PUBLICATIONS

Barker and Clevers, "Mining the Wnt pathway for cancer therapeutics," *Nature Reviews. Drug Discovery*, 5(12):997-1014, 2006.
(Continued)

*Primary Examiner* — Savitha Rao
(74) *Attorney, Agent, or Firm* — Parker Highlander PLLC

(57) ABSTRACT

The present invention generally relates to protein signalling. In particular, compounds that inhibit the Wnt protein signalling pathway are disclosed. Such compounds may be used in the treatment of Wnt protein signalling-related diseases and conditions such as cancer, degenerative diseases, type II diabetes and osteopetrosis.

6 Claims, 25 Drawing Sheets

(51) Int. Cl.
- C07D 401/12 (2006.01)
- C07D 401/14 (2006.01)
- C07D 403/10 (2006.01)
- C07D 209/48 (2006.01)
- C07D 413/04 (2006.01)
- C07D 417/12 (2006.01)
- C07D 471/04 (2006.01)
- C07D 519/00 (2006.01)
- C07D 401/10 (2006.01)

(52) U.S. Cl.
CPC ............ *C07D 403/10* (2013.01); *C07D 413/04* (2013.01); *C07D 417/12* (2013.01); *C07D 471/04* (2013.01); *C07D 519/00* (2013.01); *C07D 401/10* (2013.01)

(56) References Cited

FOREIGN PATENT DOCUMENTS

| | | |
|---|---|---|
| WO | WO 02/064572 | 8/2002 |
| WO | WO 02/067939 | 9/2002 |
| WO | WO 03/024448 | 3/2003 |

OTHER PUBLICATIONS

Chen et al., "Small molecule-mediated disruption of Wnt-dependent signal transduction in tissue regeneration and cancer," *Nature Chem. Biol*, 5(2):100-107, 2009.

Dodge and Lum, "Drugging the cancer stem cell compartment: lessons learned from the Hh and Wnt signal transduction pathways," *Annu Rev Pharmacol Toxicol.*, 51:289-310, 2011.

Lu et al., "Structure/activity relationship studies of small-molecule inhibitors of Wnt response," *Bioorg Med Chem Lett.*, 19(14):3825-3827, 2009.

PCT International Preliminary Report on Patentability issued in International Application No. PCT/US2009/045340, mailed Dec. 9, 2010.

PCT International Search Report and Written Opinion issued in International Application No. PCT/US2009/045340, mailed Dec. 18, 2009.

PCT Invitation to Pay Additional Fees issued in International Application No. PCT/US2009/045340, mailed Oct. 7, 2009.

Veeman et al., "A second canon: functions and mechanisms of β-catenin-independent Wnt signaling," *Developmental Cell*, 5(3):367-377, 2003.

Office Action issued in Australian Application No. 2009260503, mailed Jun. 5, 2012.

Cremlyn et al., "Diels-Alder reactions using N-(p-chlorosulfonylphenyl)-maleimide as dienophile", *Phosphorus and Sulfur.*, 33:65-75, 1987.

Office Action issued in Australian Application No. 2009260503, mailed Aug. 14, 2013.

Office Action issued in Chinese Application No. 200980129430.0, mailed Jan. 11, 2013.

Office Action issued in European Application No. 09 767 313.1, mailed Feb. 1, 2013.

Office Action issued in Israeli Application No. 209556, dated Jul. 18, 2013.

Office Action issued in U.S. Appl. No. 12/994,661, mailed Oct. 2, 2012.

FIG. 2
A
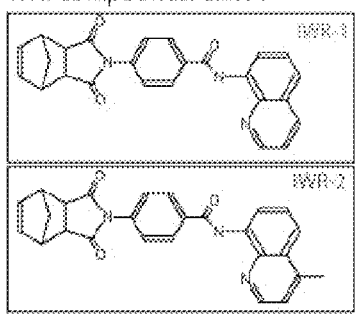
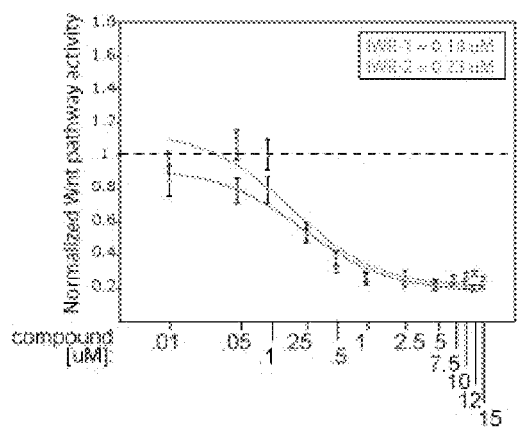
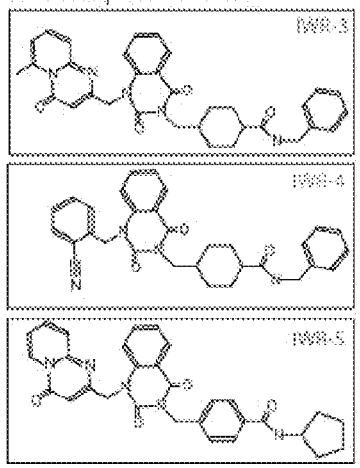
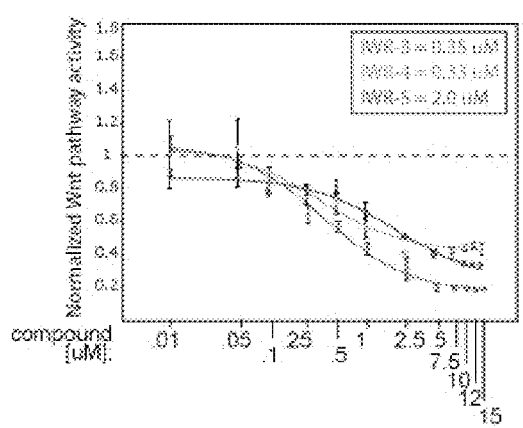
B
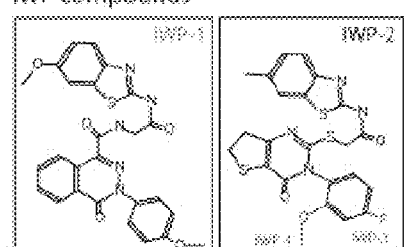
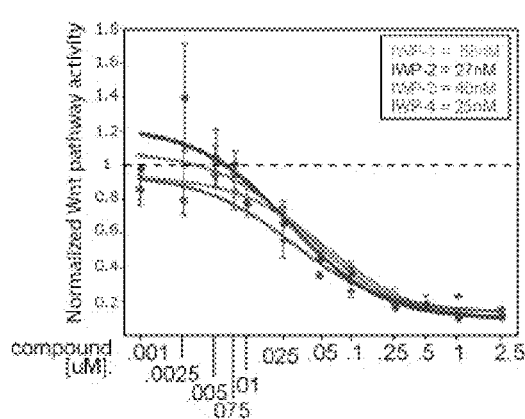

FIG. 9
A
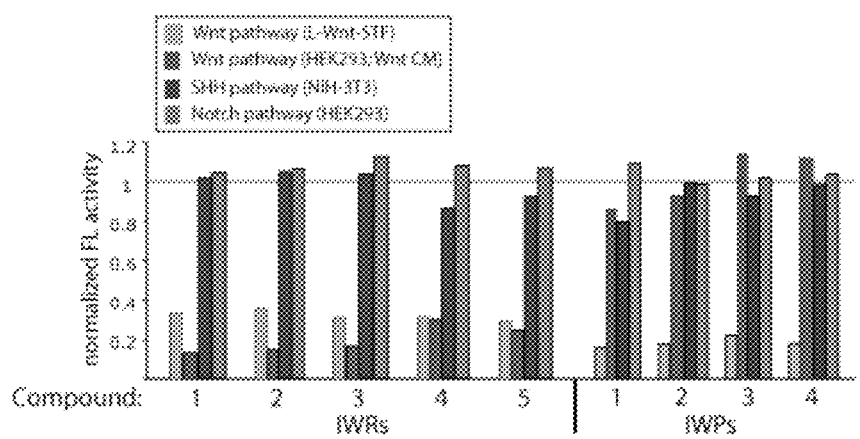
B
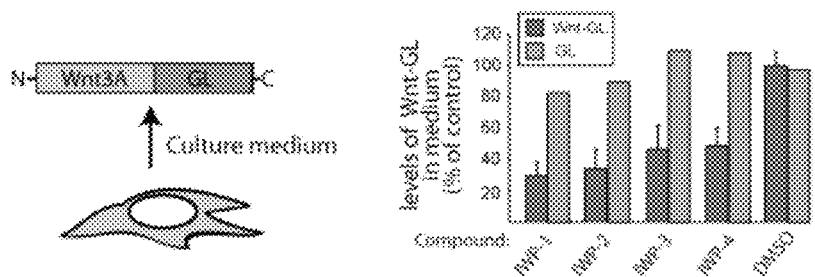
C
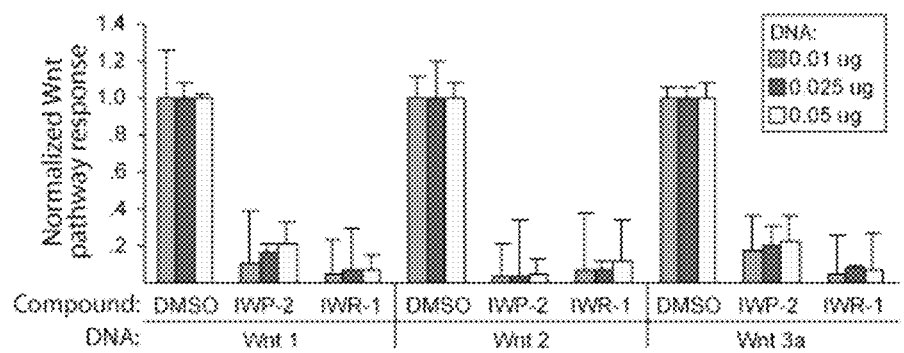

FIG. 11
A
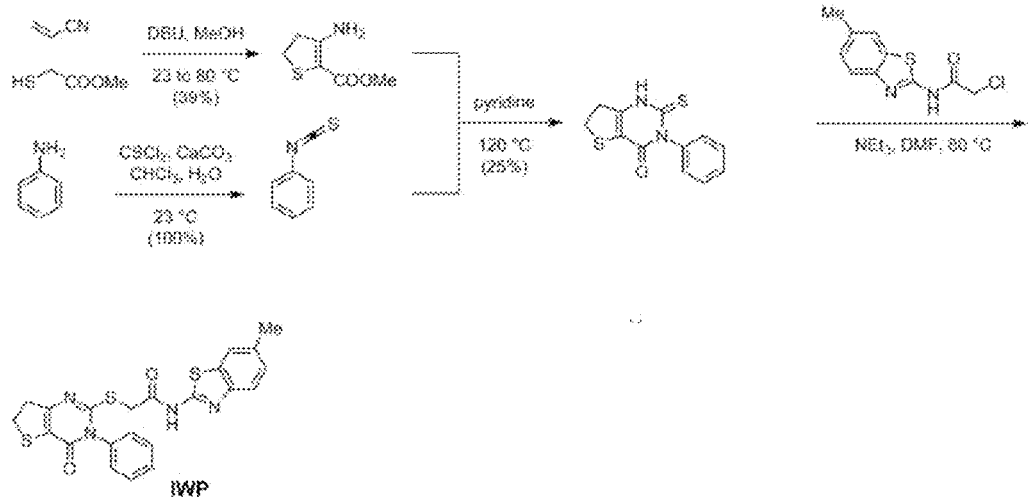
B
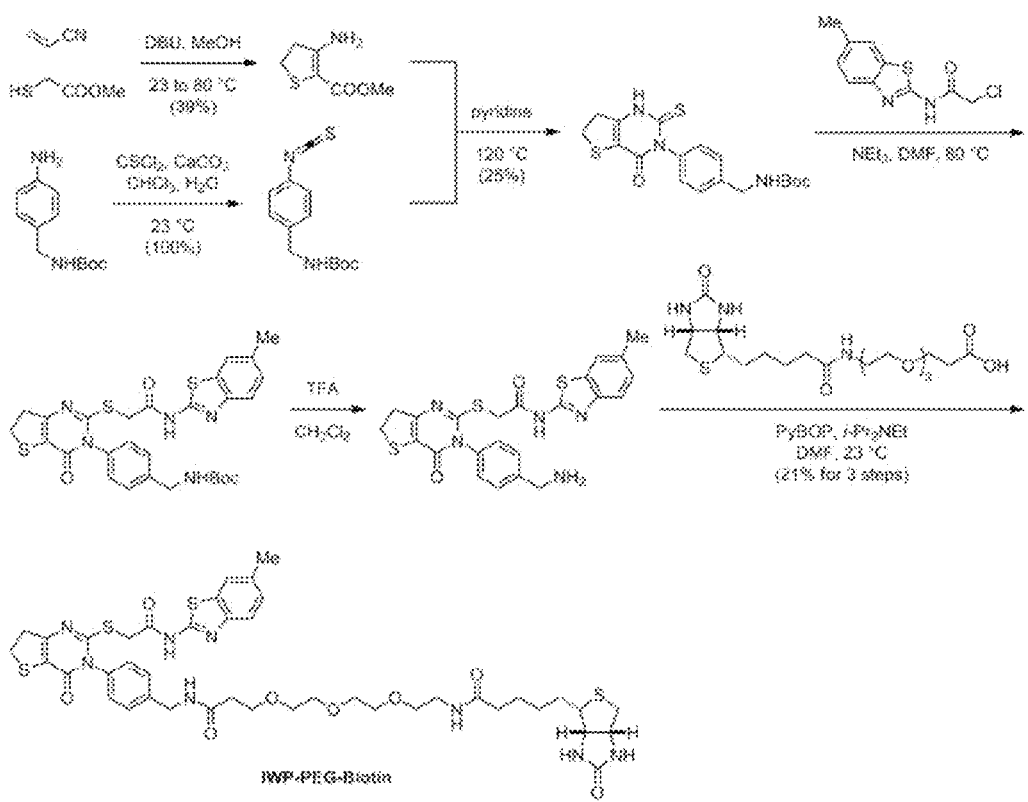

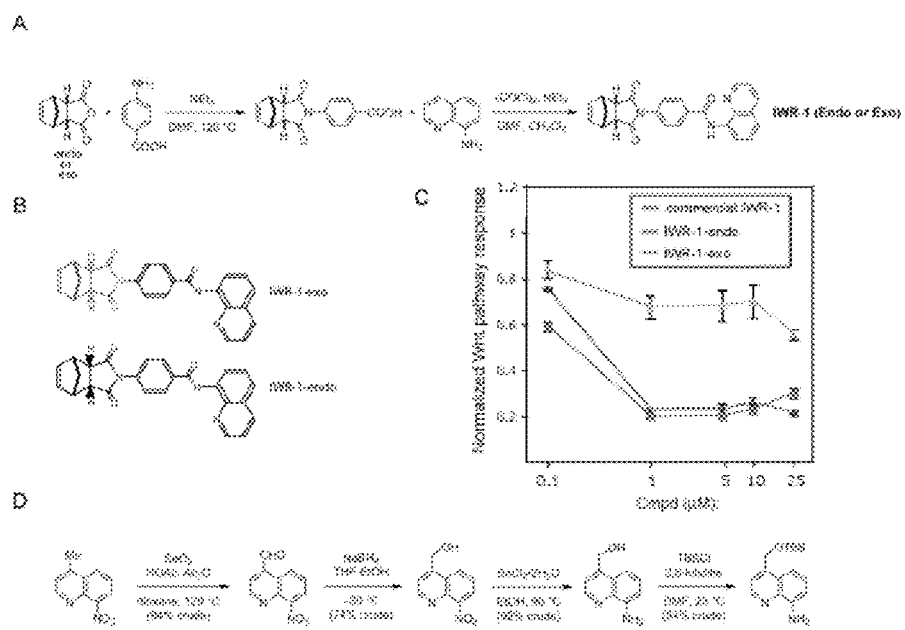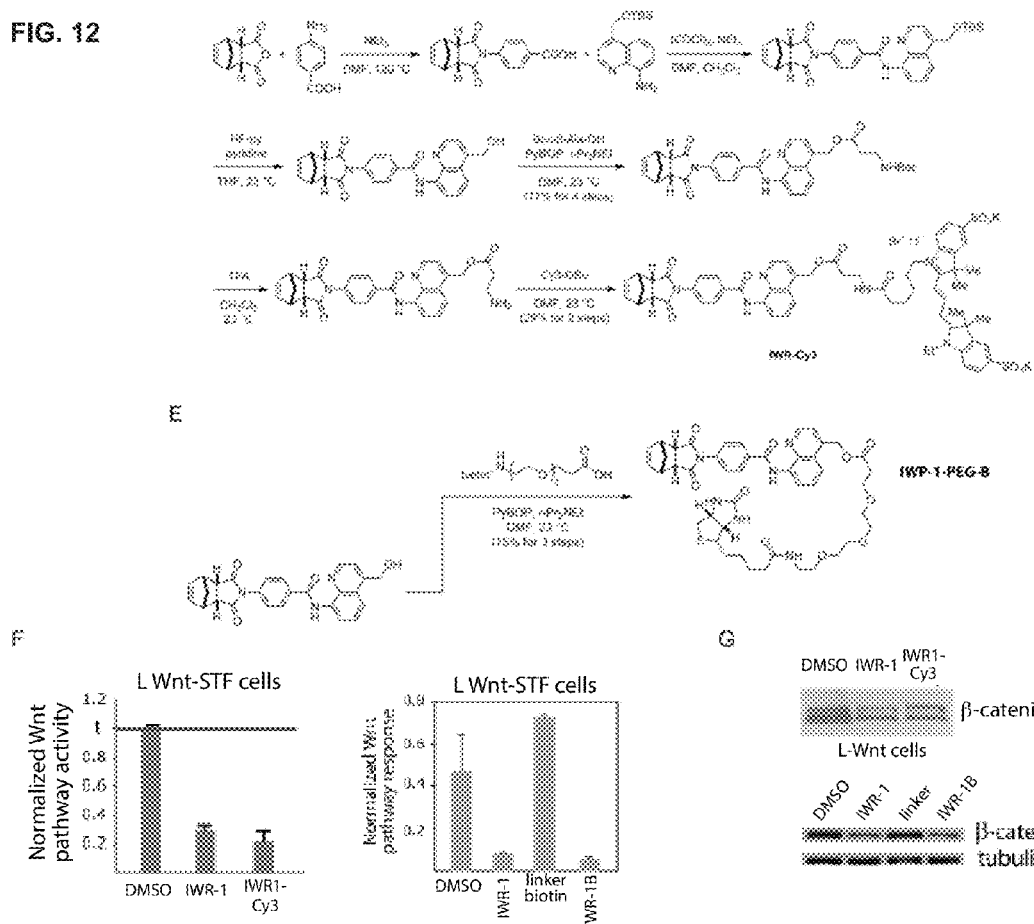
FIG. 12

FIG. 13
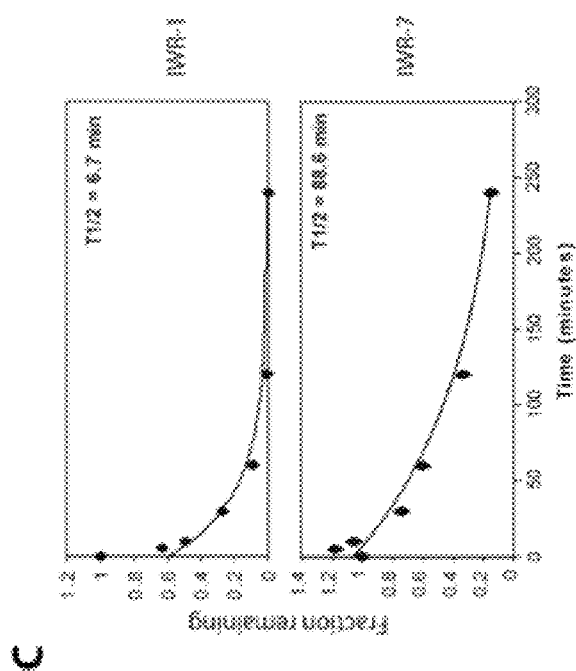
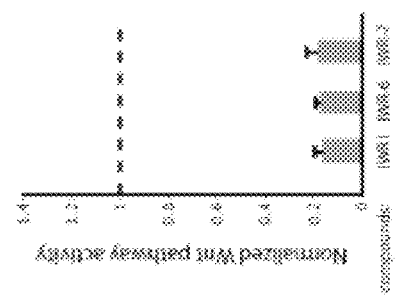
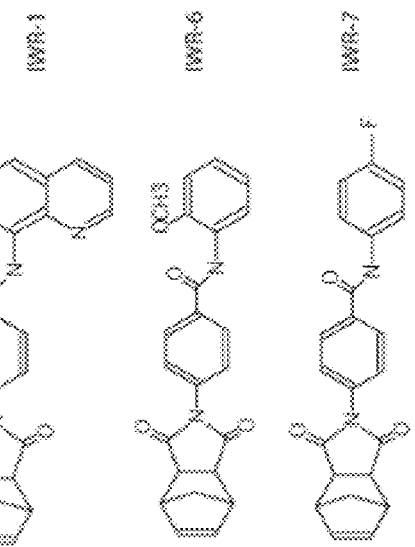

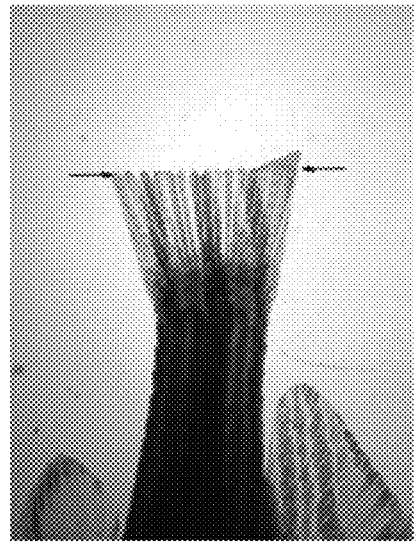
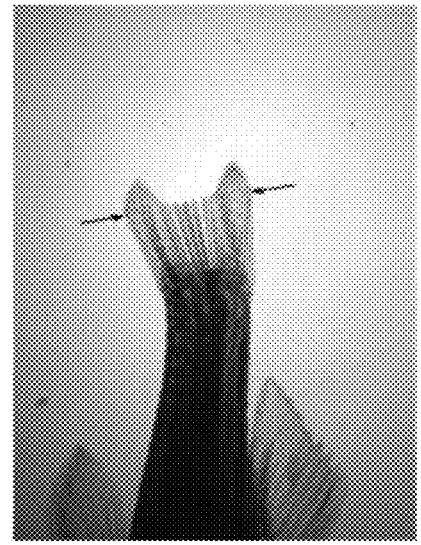
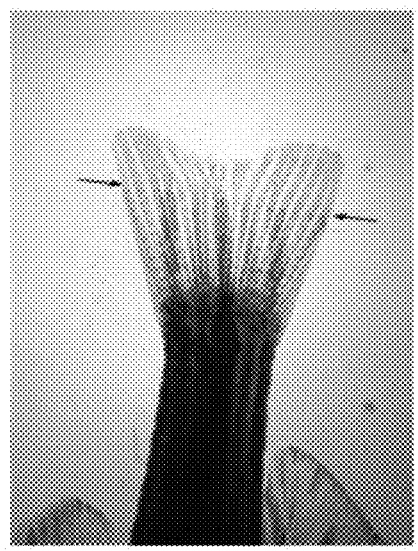
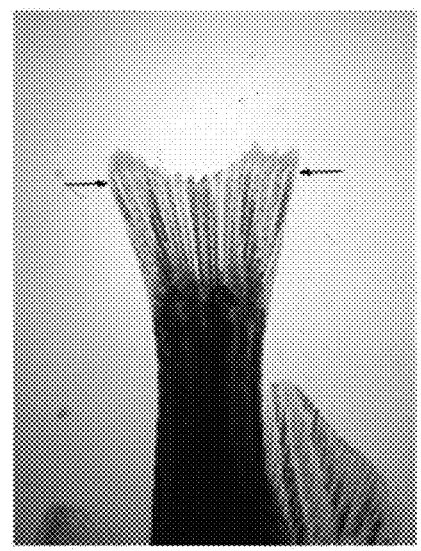
FIG. 25

WNT PROTEIN SIGNALLING INHIBITORS

The present application is a divisional of U.S. application Ser. No. 12/994,661, filed as a national phase application under 35 U.S.C. §371 of International Patent Application No. PCT/US2009/045340, filed May 27, 2009, which claims the benefit of priority to U.S. Provisional Application Nos. 61/130,149, filed May 27, 2008, and 61/204,279, filed Jan. 2, 2009. The entire text of each of the above-referenced disclosures is specifically incorporated herein by reference without disclaimer.

This invention was made with government support under grant number 1R01GM076398-01, awarded by the National Institutes of Health. The government has certain rights in the invention.

BACKGROUND OF THE INVENTION

1. Field of the Invention

The present invention generally relates to the fields of molecular biology and medicine. More particularly, it concerns the discovery of compounds that inhibit Wnt-mediated signal transduction pathways, including the Wnt/β-catenin pathway.

2. Description of Related Art

The secreted Wnt signalling proteins are deployed in almost all aspects of embryonic development in vertebrates (Clevers, 2006). In post-embryonic animals, their functions are essential to homeostatic tissue renewal and regeneration (Reya and Clevers, 2005). Similar to that of several other signal transduction pathways that have been shown to be important to cell fate decision-making, activity of the Wnt/β-catenin pathway maintains transcriptional programs that enable stem cells to retain their multi-potency (Cole et al., 2008; Van der Flier et al., 2007). Inability to sustain these transcription programs, perhaps through loss of members of the TCF/LEF family of transcriptional effectors or the β-catenin transcriptional co-activator, results in compromised ability of stem cells to self-renew (Cole et al., 2008; Fevr et al., 2007; Korinek et al., 1998; Muncan et al., 2007).

Pathological states that may arise from altered stem cell function, such as degenerative diseases and cancer, are frequently associated with changes in Wnt/β-catenin pathway activity. Indeed, hyperactivation of the Wnt/β-catenin pathway is thought to induce premature senescence of stem cells and age-related loss of stem cell function (Brack et al., 2007; Liu et al., 2007). In cancer, hyperactivation of the Wnt/β-catenin pathway, often in conjunction with mutations in other cell growth regulatory genes, can lead to aberrant cell growth (Reya and Clevers, 2005). Notably, 90% of colorectal cancers are initiated by the loss of the *adenomatosis polyposis coli* (APC) gene, a major suppressor of the Wnt/β-catenin pathway (Kinzler and Vogelstein, 1996; Sjoblom et al., 2006). Less frequently, loss of extracellular inhibitors that normally suppress Wnt protein function may give rise to Wnt ligand-dependent tumors (Polakis, 2007). More recently Wnt-mediated cellular responses that are not dependent upon β-catenin (so called "non-canonical pathways" have also been shown play important roles in cancer (Veeman et al., 2003).

Accordingly, identification of methods and compounds that modulate the Wnt-dependent cellular responses may offer an avenue for therapeutic treatment of diseases associated with aberrant activity of these pathways.

SUMMARY OF THE INVENTION

The present invention generally provides compounds and their use as Wnt protein signalling inhibitors. Also provided are methods of synthesis of these compounds and pharmaceutical compositions thereof.

Accordingly, in one aspect, the present invention provides a method of inhibiting Wnt protein signalling in a cell comprising administering to the cell an effective amount of a compound of formula (A):

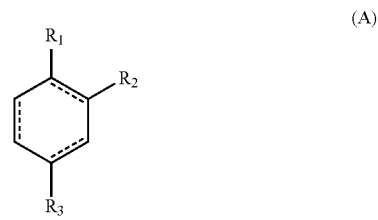

wherein:
$R_1$ is selected from the group consisting of

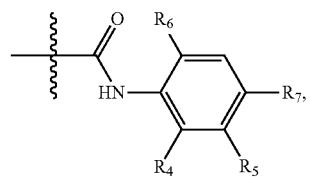

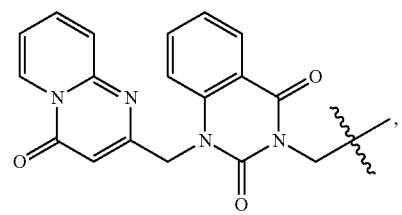

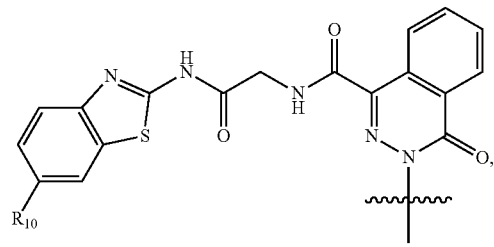

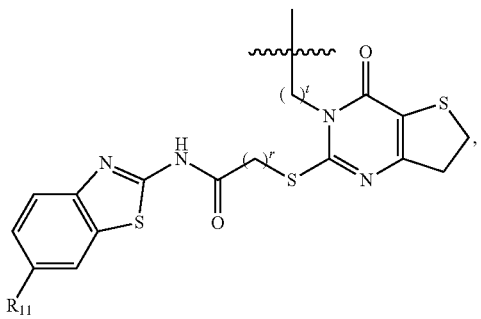

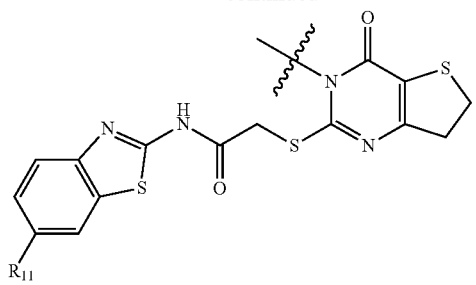

and

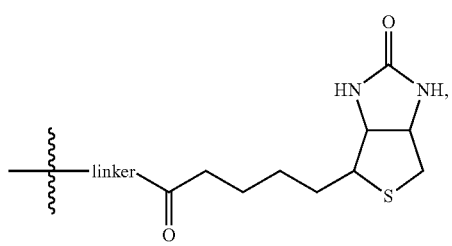

and $R_{12}$ is selected from the group consisting of

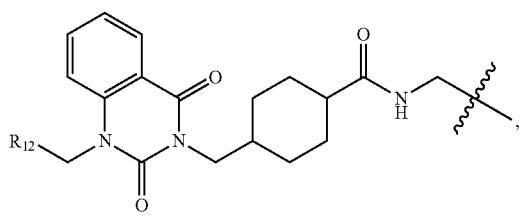

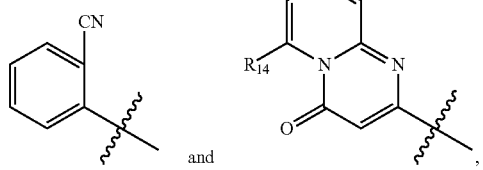

and wherein $R_4$ and $R_5$ are each independently selected from the group consisting of hydrogen, alkyl$_{(C\leq 4)}$, substituted alkyl$_{(C\leq 4)}$, alkoxy$_{(C\leq 4)}$, substituted alkoxy$_{(C\leq 4)}$ and

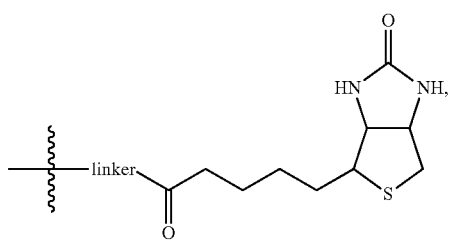

and r and t are each independently 0 or 1; or $R_4$ and $R_5$ taken together form the following moiety:

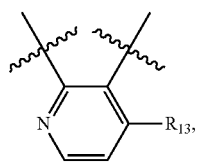

wherein $R_{13}$ is selected from the group consisting of hydrogen, halogen, alkyl$_{(C\leq 4)}$, substituted alkyl$_{(C\leq 4)}$, alkoxy$_{(C\leq 4)}$, substituted alkoxy$_{(C\leq 4)}$ and a label;

$R_6$, $R_7$ and $R_9$-$R_{11}$ are each independently selected from the group consisting of hydrogen, halogen, alkyl$_{(C\leq 4)}$, substituted alkyl$_{(C\leq 4)}$, alkoxy$_{(C\leq 4)}$, substituted alkoxy$_{(C\leq 4)}$ and wherein $R_{14}$ is selected from the group consisting of hydrogen, alkyl$_{(C\leq 4)}$, substituted alkyl$_{(C\leq 4)}$, alkoxy$_{(C\leq 4)}$ and substituted alkoxy$_{(C\leq 4)}$;

$R_2$ is selected from the group consisting of hydrogen, alkyl$_{(C\leq 4)}$, substituted alkyl$_{(C\leq 4)}$, alkoxy$_{(C\leq 4)}$ and substituted alkoxy$_{(C\leq 4)}$; and $R_3$ is selected from the group consisting of hydrogen, halogen, alkyl$_{(C\leq 4)}$, substituted alkyl$_{(C\leq 4)}$, alkoxy$_{(C\leq 4)}$, substituted alkoxy$_{(C\leq 4)}$,

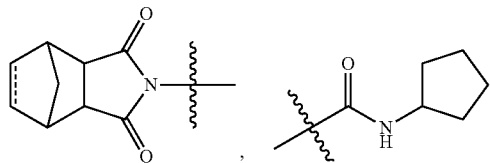

and

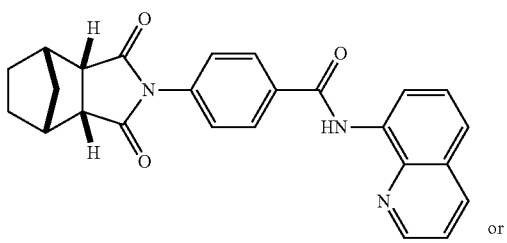

In some embodiments, the compound is:

or

-continued

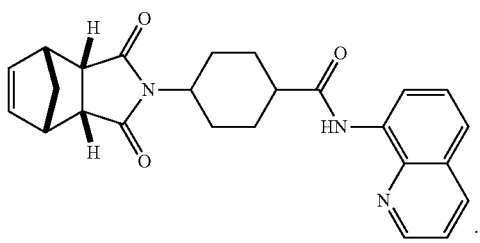

In some embodiments the compound is any of the compounds disclosed in section III below, entitled "Wnt Protein Signalling Inhibitors."

In some embodiments, the present invention provides a method of inhibiting Wnt protein signalling in a cell comprising administering to the cell an effective amount of a compound of formula (I):

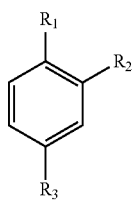

(I)

wherein: $R_1$ is selected from the group consisting of

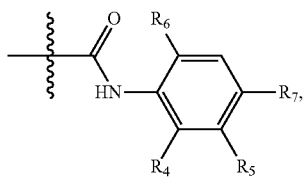

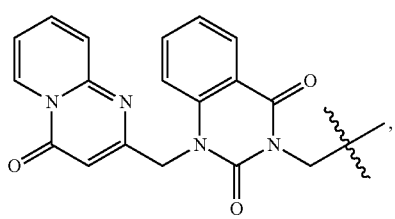

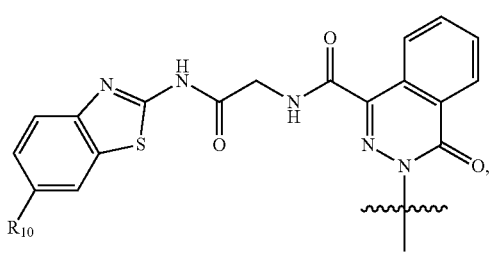

-continued

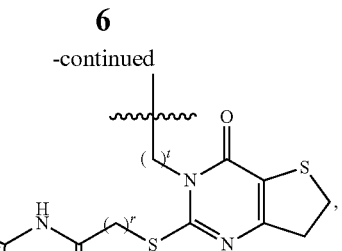

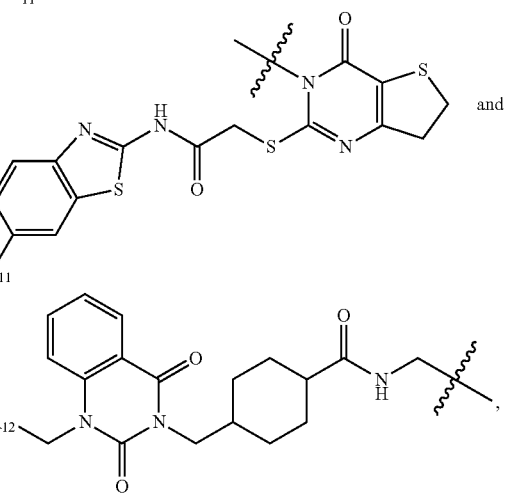

wherein $R_4$ and $R_5$ are each independently selected from the group consisting of hydrogen, alkyl$_{(C \leq 4)}$, substituted alkyl$_{(C \leq 4)}$, alkoxy$_{(C \leq 4)}$, substituted alkoxy$_{(C \leq 4)}$ and

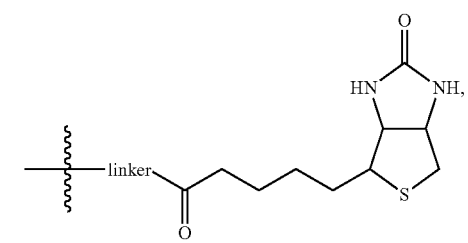

and r and t are each independently 0 or 1, or $R_4$ and $R_5$ taken together form the following moiety:

wherein $R_{13}$ is selected from the group consisting of hydrogen, halogen, alkyl$_{(C \leq 4)}$, substituted alkyl$_{(C \leq 4)}$, alkoxy$_{(C \leq 4)}$, substituted alkoxy$_{(C \leq 4)}$ and a label; $R_6$, $R_7$ and $R_9$-$R_{11}$ are each independently selected from the group consisting of hydrogen, halogen, alkyl$_{(C \leq 4)}$, substituted alkyl$_{(C \leq 4)}$, alkoxy$_{(C \leq 4)}$, substituted alkoxy$_{(C \leq 4)}$ and

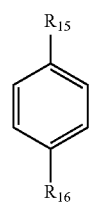

(II)

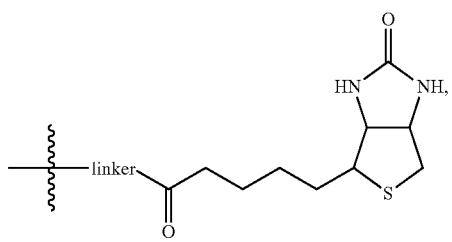

and $R_{12}$ is selected from the group consisting of wherein: $R_{15}$ is selected from the group consisting of

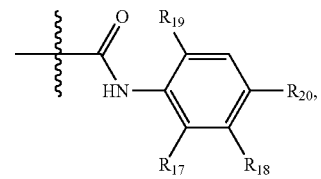

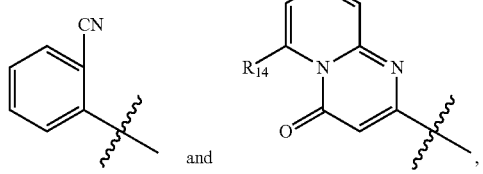

wherein $R_{14}$ is selected from the group consisting of hydrogen, alkyl$_{(C\leq 4)}$, substituted alkyl$_{(C\leq 4)}$, alkoxy$_{(C\leq 4)}$ and substituted alkoxy$_{(C\leq 4)}$; $R_2$ is selected from the group consisting of hydrogen, alkyl$_{(C\leq 4)}$, substituted alkyl$_{(C\leq 4)}$, alkoxy$_{(C\leq 4)}$ and substituted alkoxy$_{(C\leq 4)}$; and $R_3$ is selected from the group consisting of hydrogen, halogen, alkyl$_{(C\leq 4)}$, substituted alkyl$_{(C\leq 4)}$, alkoxy$_{(C\leq 4)}$, substituted alkoxy$_{(C\leq 4)}$,

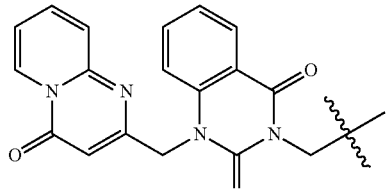

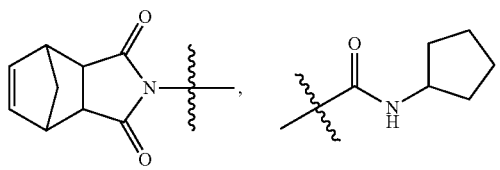

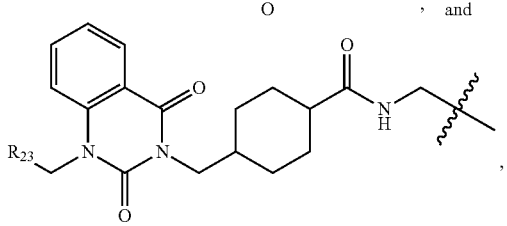

wherein: $R_{17}$ and $R_{18}$ are each independently selected from the group consisting of hydrogen, alkyl$_{(C\leq 4)}$, substituted alkyl$_{(C\leq 4)}$, alkoxy$_{(C\leq 4)}$, substituted alkoxy$_{(C\leq 4)}$ and

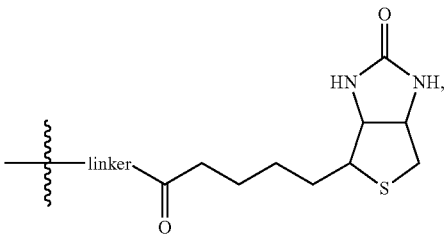

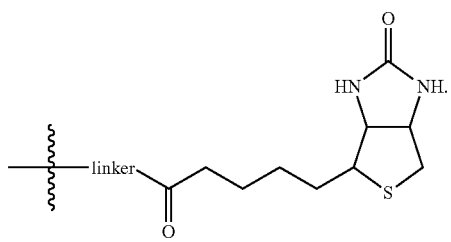

or $R_{17}$ and $R_{18}$ taken together form the following moiety:

Moreover, this or any other method regarding a cell may take place wherein the cell is in vitro, or wherein the cell is in vivo.

In certain embodiments, a method of the present invention (e.g., a method of inhibiting Wnt protein signalling in a cell) may be further defined as a method of inhibiting Wnt response.

In certain embodiments, such as but not limited to methods of inhibiting Wnt response, a compound of formula (I) may be further defined as a compound of formula (II):

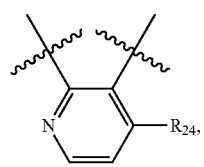

wherein $R_{24}$ is selected from the group consisting of hydrogen, halogen, alkyl$_{(C\leq 4)}$, substituted alkyl$_{(C\leq 4)}$, alkoxy$_{(C\leq 4)}$, substituted alkoxy$_{(C\leq 4)}$, and a label; $R_{10}$ and $R_{20}$ are each independently selected from the group consisting of hydrogen, halogen, alkyl$_{(C\leq4)}$, substituted alkyl$_{(C\leq4)}$, alkoxy$_{(C\leq4)}$, substituted alkoxy$_{(C\leq4)}$ and

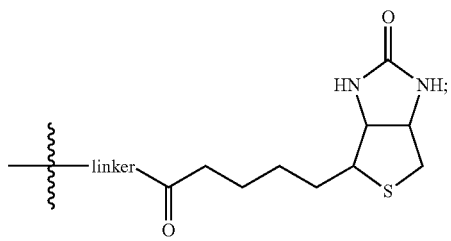

R$_{23}$ is selected from the group consisting of

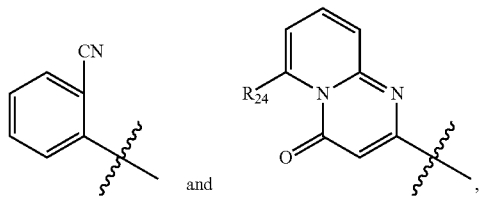

wherein R$_{24}$ is selected from the group consisting of hydrogen, alkyl$_{(C\leq4)}$, substituted alkyl$_{(C\leq4)}$, alkoxy$_{(C\leq4)}$, substituted alkoxy$_{(C\leq4)}$; and R$_{16}$ is selected from the group consisting of hydrogen, alkyl$_{(C\leq4)}$, substituted alkyl$_{(C\leq4)}$,

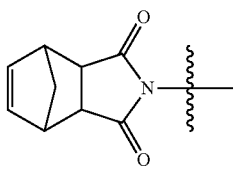 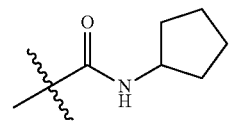

In particular embodiments, the compound of formula (II) may be further defined as any one or more of the following:

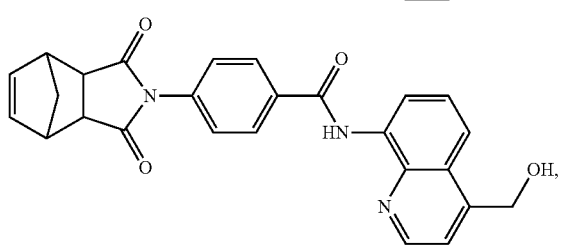 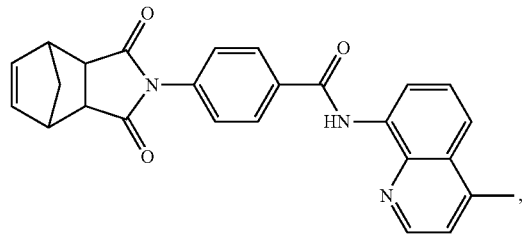

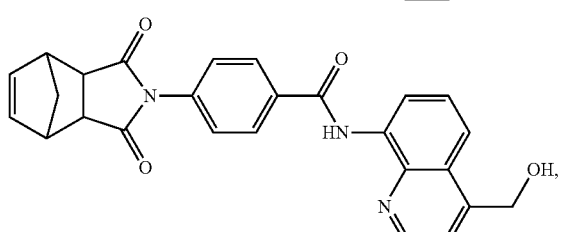 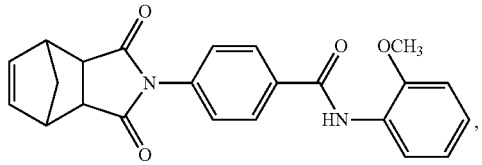

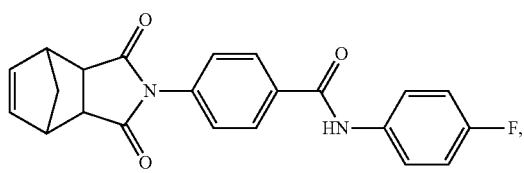

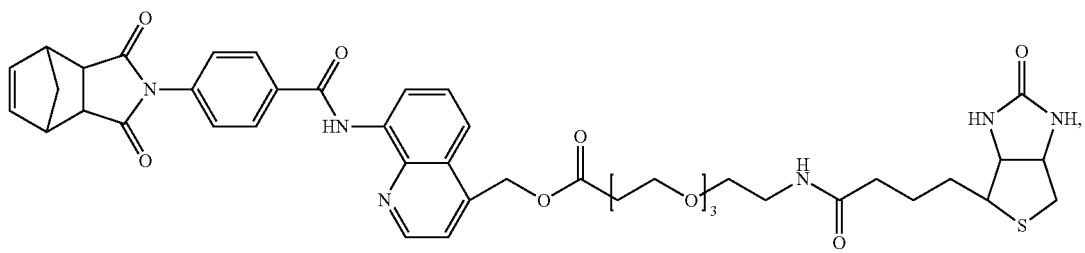

-continued

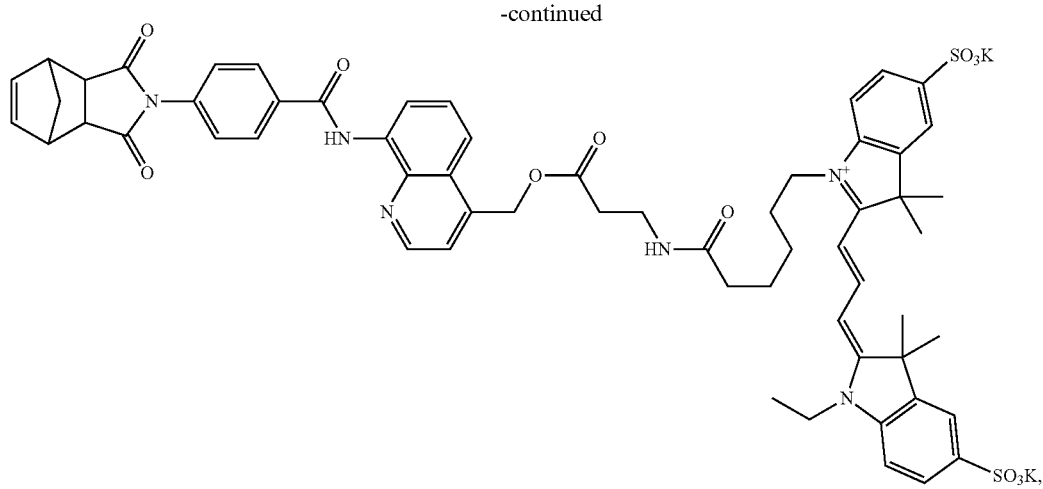

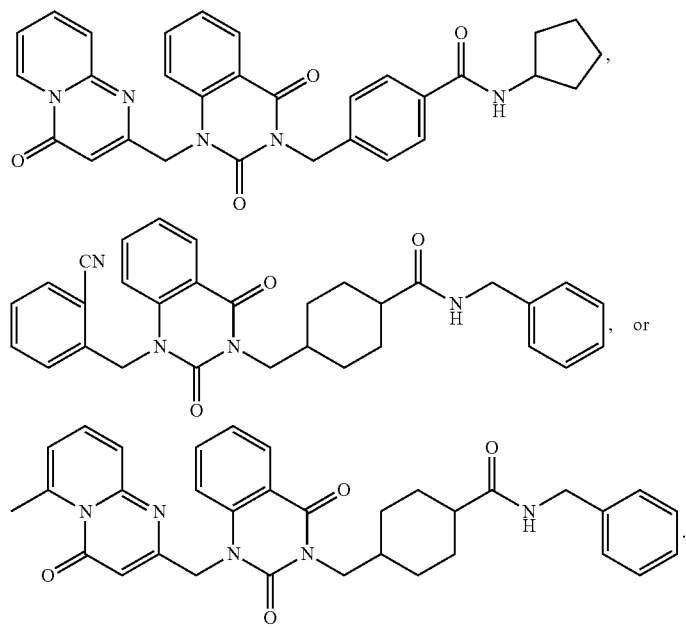

In certain embodiments, a method of the present invention (e.g., a method of inhibiting Wnt protein signalling) may be further defined as a method of inhibiting Wnt protein production. For example, a method of inhibiting Wnt protein production in a cell may comprise administering a compound of formula (I) to the cell. In certain embodiments, the compound of formula (I) may be further defined as a compound of formula (III):

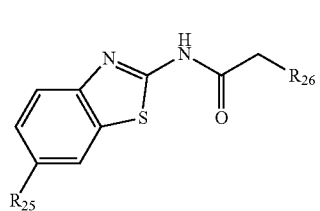

(III)

wherein: $R_{25}$ is alkyl$_{(C \leq 4)}$, substituted alkyl$_{(C \leq 4)}$, alkoxy$_{(C \leq 4)}$, or substituted alkoxy$_{(C \leq 4)}$; and $R_{26}$ is selected from the group consisting of

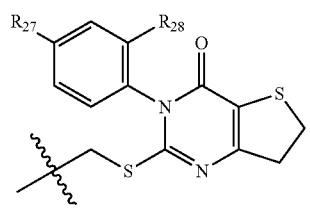

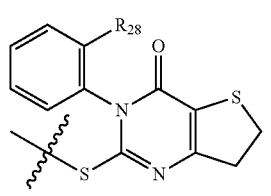

13
-continued
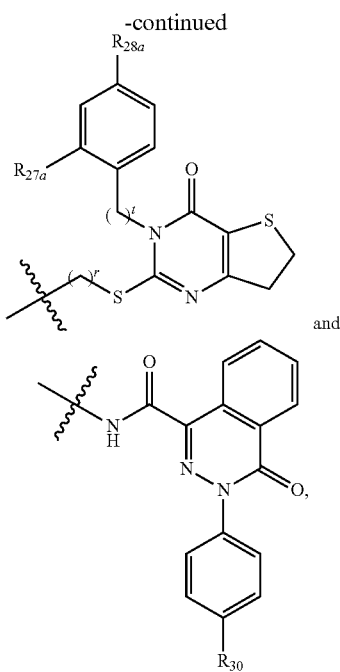
and
14
wherein $R_{27}$-$R_{30}$, $R_{27a}$ and $R_{28a}$ are each independently selected from the group consisting of hydrogen, halogen, alkyl$_{(C \leq 4)}$, substituted alkyl$_{(C \leq 4)}$, alkoxy$_{(C \leq 4)}$, substituted alkoxy$_{(C \leq 4)}$ and
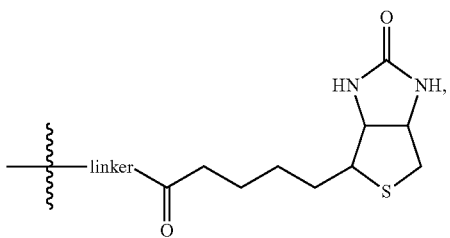
and r and t are each independently 0 or 1. In certain embodiments, the compound of formula (III) is further defined as any one or more of the following:
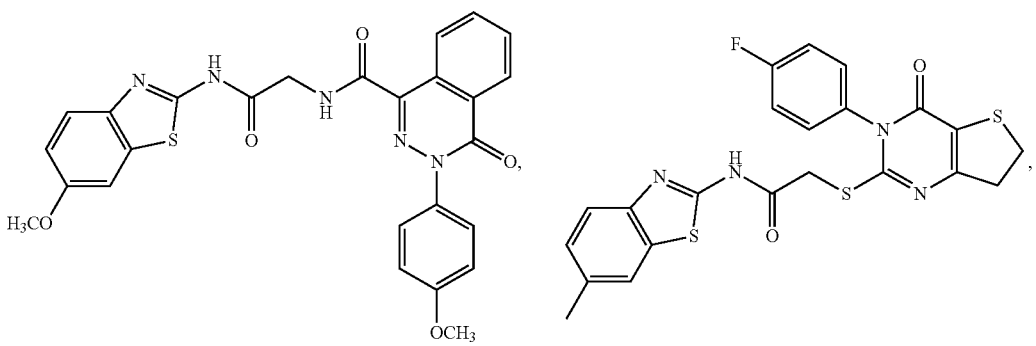
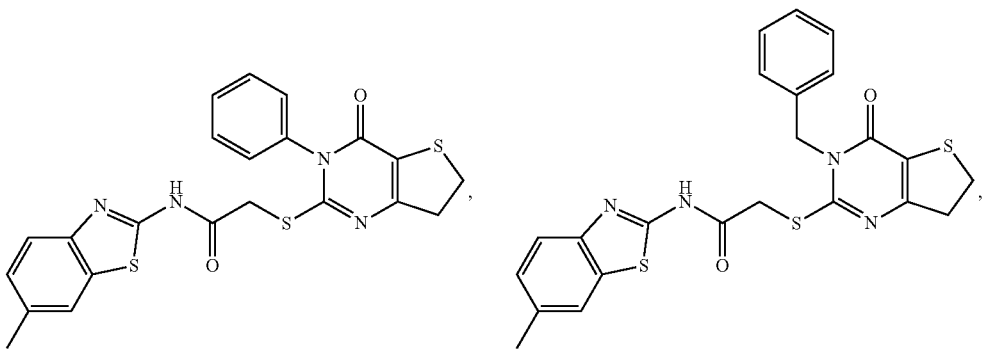

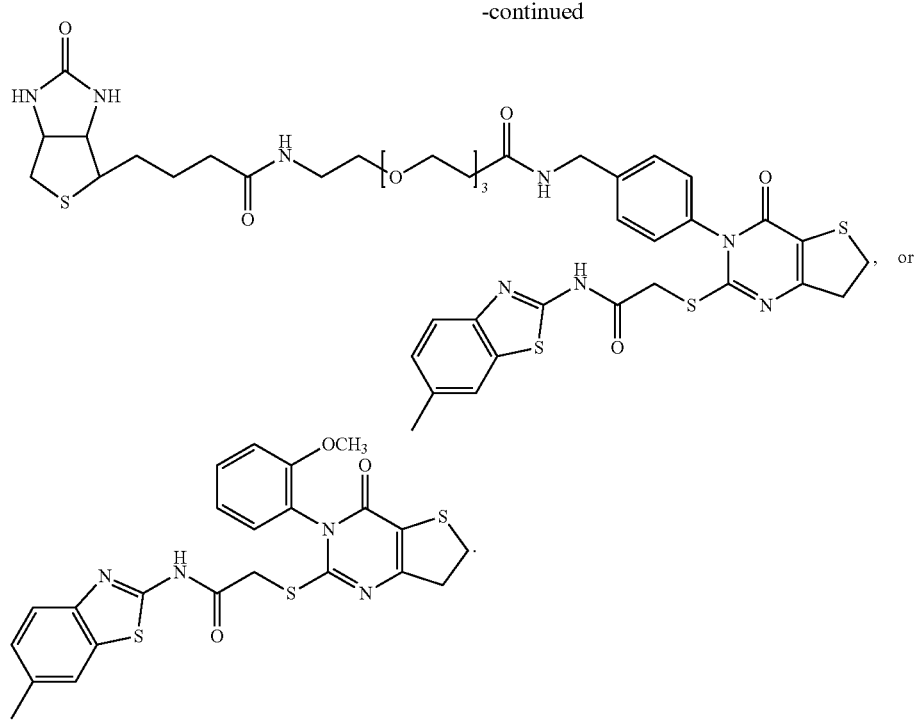, or

In certain embodiments, the compound of formula (I) is further defined as a compound of formula (IV):

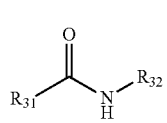   (IV)

wherein: $R_{31}$ is selected from the group consisting of

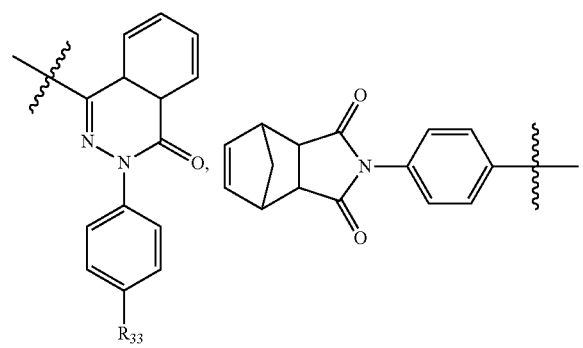

and

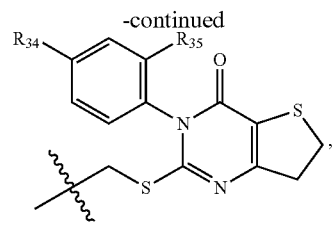

wherein $R_{33}$-$R_{35}$ are selected from the group consisting of hydrogen, halogen, alkyl$_{(C\leq 4)}$, substituted alkyl$_{(C\leq 4)}$, alkoxy$_{(C\leq 4)}$, substituted alkoxy$_{(C\leq 4)}$ and

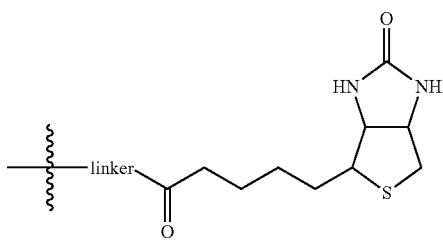

and t is 0 or 1; and $R_{32}$ is selected from the group consisting of

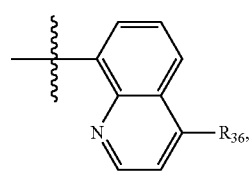

-continued

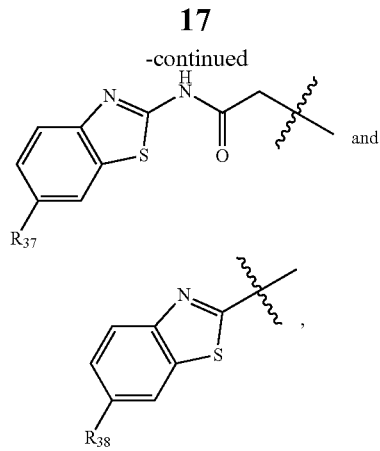

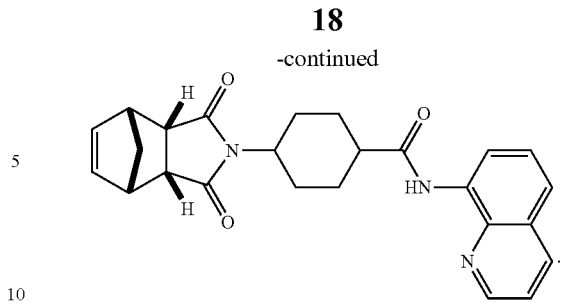

wherein R₃₆-R₃₈ are selected from the group consisting of hydrogen, halogen, alkyl$_{(C≤4)}$, substituted alkyl$_{(C≤4)}$, alkoxy$_{(C≤4)}$ and substituted alkoxy$_{(C≤4)}$.

Labels employed in methods, compounds and compositions of the present invention may be any type known to those of skill in the art. For example, a label may be further defined as comprising biotin, such as the following:

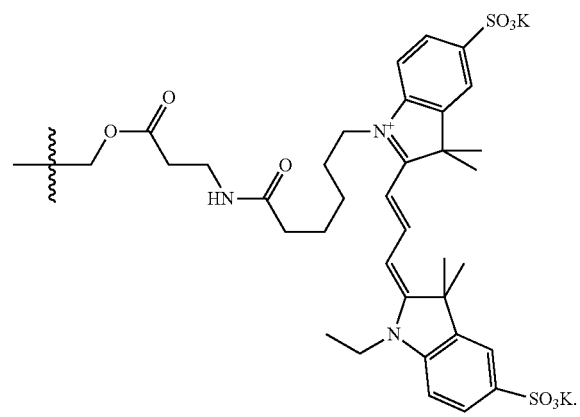

Alternatively, the label may comprise a fluorophore, such as the following:

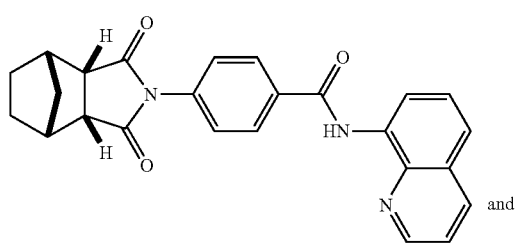

In another aspect, the present invention provides the compounds:

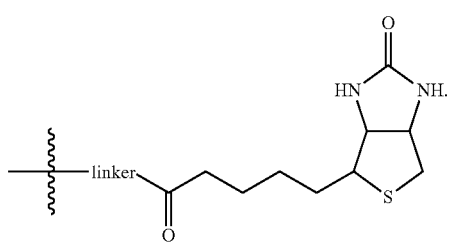

-continued

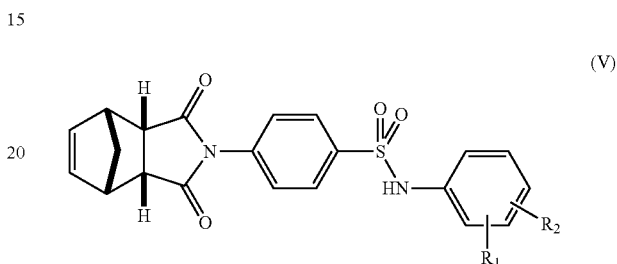

In yet another aspect the present invention provides compounds of formula (V) or formula (VI):

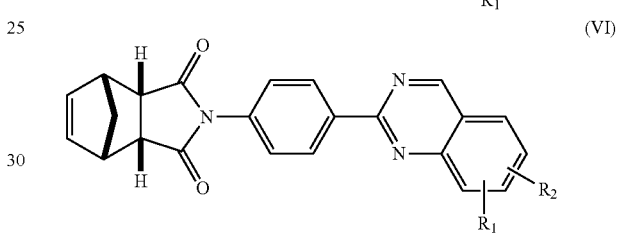

wherein for either formula:

R₁ and R₂ when taken alone, are each independently:

hydrogen, hydroxy, halo, amino, nitro, hydroxyamino, cyano, azido or mercapto; or alkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, heteroaralkyl$_{(C≤12)}$, alkoxy$_{(C≤12)}$, alkenyloxy$_{(C≤12)}$, alkynyloxy$_{(C≤12)}$, aryloxy$_{(C≤12)}$, aralkoxy$_{(C≤12)}$, heteroaryloxy$_{(C≤12)}$, heteroaralkoxy$_{(C≤12)}$, acyloxy$_{(C≤12)}$, alkylamino$_{(C≤12)}$, dialkylamino$_{(C≤12)}$, alkoxyamino$_{(C≤12)}$, alkenylamino$_{(C≤12)}$, alkynylamino$_{(C≤12)}$, arylamino$_{(C≤12)}$, aralkylamino$_{(C≤12)}$, heteroarylamino$_{(C≤12)}$, heteroaralkylamino$_{(C≤12)}$, amido$_{(C≤12)}$, or a substituted version of any of these groups; or R₁ and R₂, when taken together, are alkanediyl$_{(C2-12)}$, alkenediyl$_{(C2-12)}$, or a substituted version of either of these groups.

In some embodiments, R₁ and R₂ when taken together are:

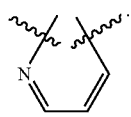

In other embodiments, R₁ or R₂ is halo. In some variations, R₁ or R₂ is bromo. In other embodiments, R₁ or R₂ is alkoxy$_{(C≤6)}$, for example, R₁ or R₂ can be methoxy. Examples of compounds provided by the present invention include:

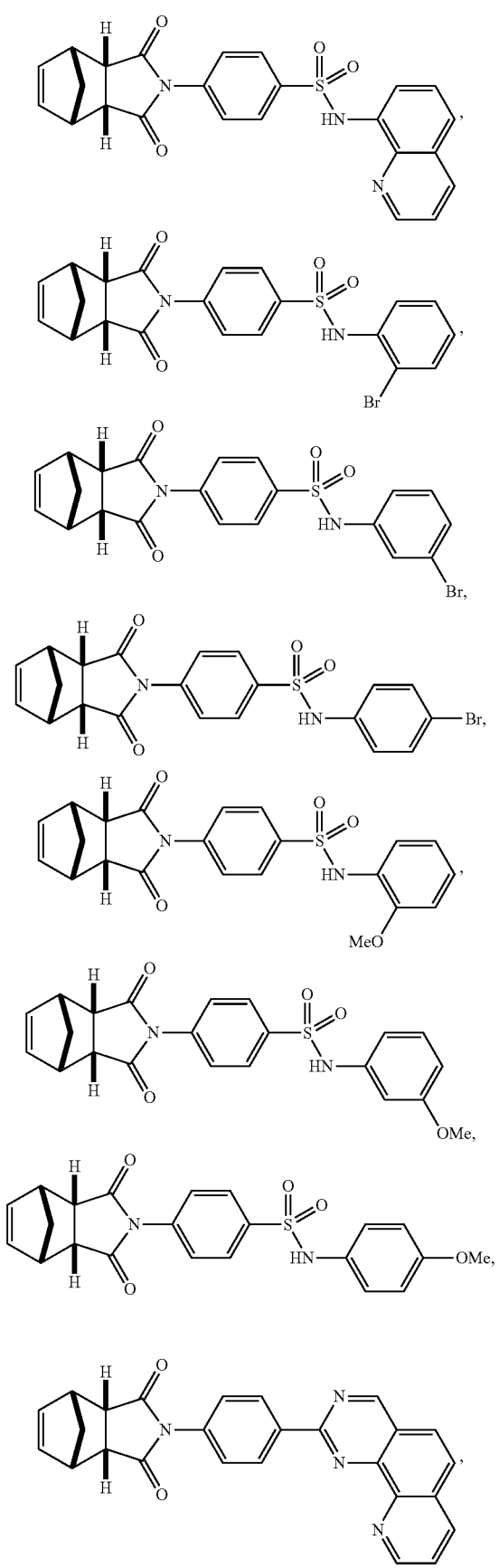
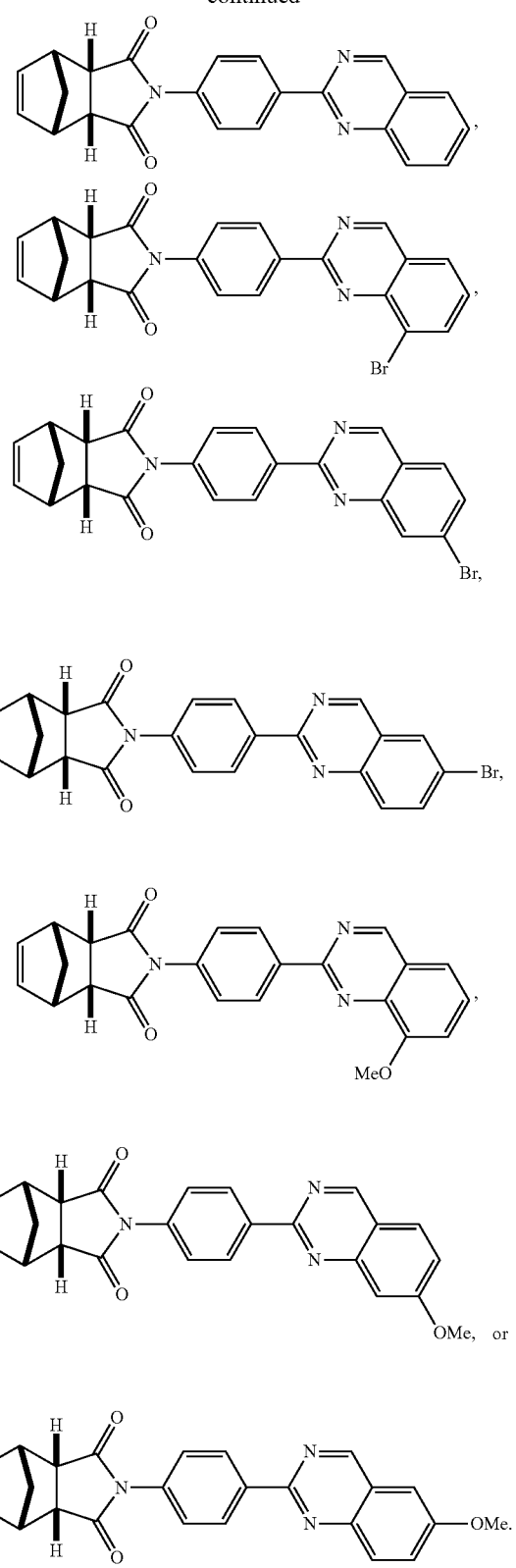
In another aspect, the invention provides a method of inhibiting Wnt protein signalling in a cell comprising administering to the cell an effective amount of a compound of either formula (V) or formula (VI):

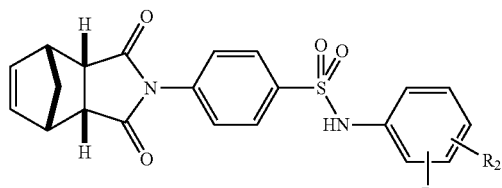

(V)

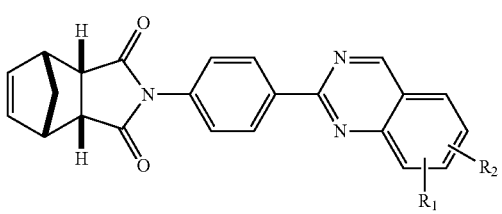

(VI)

wherein for either formula:
  $R_1$ and $R_2$ when taken alone, are each independently:
    hydrogen, hydroxy, halo, amino, nitro, hydroxyamino, cyano, azido or mercapto; or
    alkyl$_{(C\le12)}$, alkenyl$_{(C\le12)}$, alkynyl$_{(C\le12)}$, aryl$_{(C\le12)}$, aralkyl$_{(C\le12)}$, heteroaryl$_{(C\le12)}$, heteroaralkyl$_{(C\le12)}$, alkoxy$_{(C\le12)}$, alkenyloxy$_{(C\le12)}$, alkynyloxy$_{(C\le12)}$, aryloxy$_{(C\le12)}$, aralkoxy$_{(C\le12)}$, heteroaryloxy$_{(C\le12)}$, heteroaralkoxy$_{(C\le12)}$, acyloxy$_{(C\le12)}$, alkylamino$_{(C\le12)}$, dialkylamino$_{(C\le12)}$, alkoxyamino$_{(C\le12)}$, alkenylamino$_{(C\le12)}$, alkynylamino$_{(C\le12)}$, arylamino$_{(C\le12)}$, aralkylamino$_{(C\le12)}$, heteroarylamino$_{(C\le12)}$, heteroaralkylamino$_{(C\le12)}$, amido$_{(C\le12)}$, or a substituted version of any of these groups; or
  $R_1$ and $R_2$, when taken together, are alkanediyl$_{(C2-12)}$, alkenediyl$_{(C2-12)}$, or a substituted version of either of these groups.

In some embodiments, the cell is in vitro. In other embodiments, the cell is in vivo. In some embodiments, the method of inhibiting Wnt protein signalling is further defined as a method of inhibiting Wnt response. In some embodiments, the method further comprises one of the specific compounds described above.

Methods of treatment are also contemplated by the present invention. Such methods may employ any compounds of the compounds described herein. For example, such methods may employ compounds of formulas (A) and (I)-(VI), described above and below. For example, the present invention contemplates a method of treating cancer in a patient comprising administering to the patient an effective amount of a compound of formula (A) or any of its sub-generic formulas (I), (II), (III), and/or (IV). Similarly, the present invention contemplates a method of treating cancer in a patient comprising administering to the patient an effective amount of a compound of formula (V) or (VI) or any of their sub-generic formulas. The specific compounds described herein are also contemplated in methods of treating cancer. For example, this includes any of the compounds disclosed in section III below, entitled "Wnt Protein Signalling Inhibitors."

The cancer may be colorectal, breast, liver, lung, or prostate cancer. Methods of treating cancer may also further comprise administration of a chemotherapeutic, radiation therapy, immunotherapy, hormone therapy, toxin therapy, or gene therapy: such additional methodologies are well-known in the art. Methods of administration may include intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, subcutaneously, subconjunctival, intravesicularlly, mucosally, intrapericardially, intraumbilically, intraocularally, orally, locally, via inhalation, via injection, via infusion, via continuous infusion, via localized perfusion bathing target cells directly, via a catheter, via a lavage, in cremes, in lipid compositions, or any combination thereof. Dosages may include, e.g., about 1 μg/kg to about 100 mg/kg, or any range derivable therein.

In any method described herein, the compounds disclosed herein may be combined with a pharmaceutically acceptable carrier, diluent, and/or excipient in a pharmaceutical composition.

As noted above, pharmaceutical compositions are contemplated by the present invention. In certain embodiments, a pharmaceutical composition comprising a pharmaceutically acceptable carrier, diluent, and/or excipient and any one or more of the following compounds is contemplated:

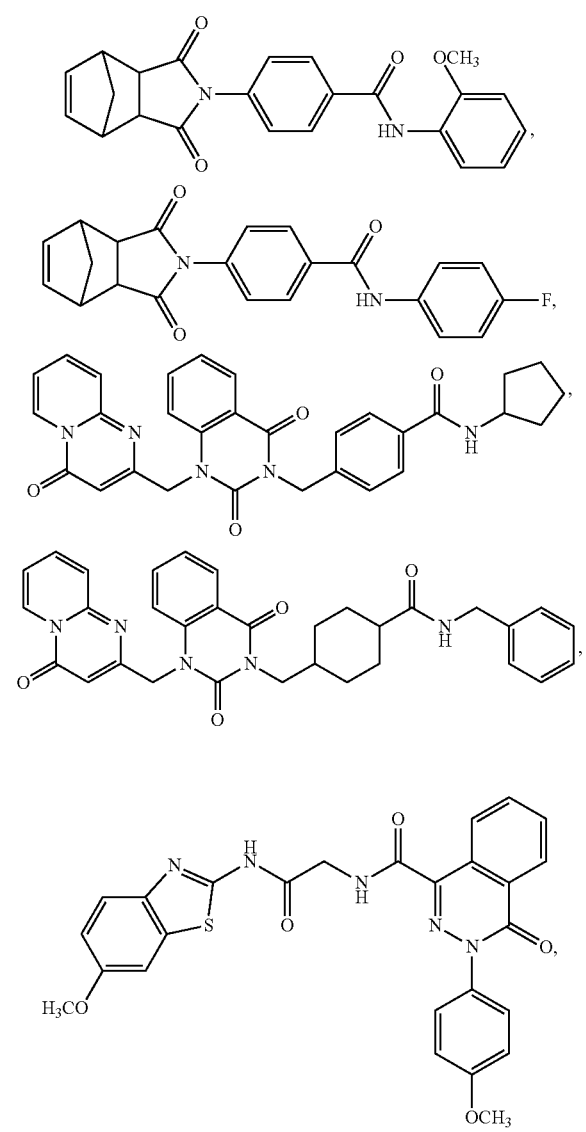

-continued

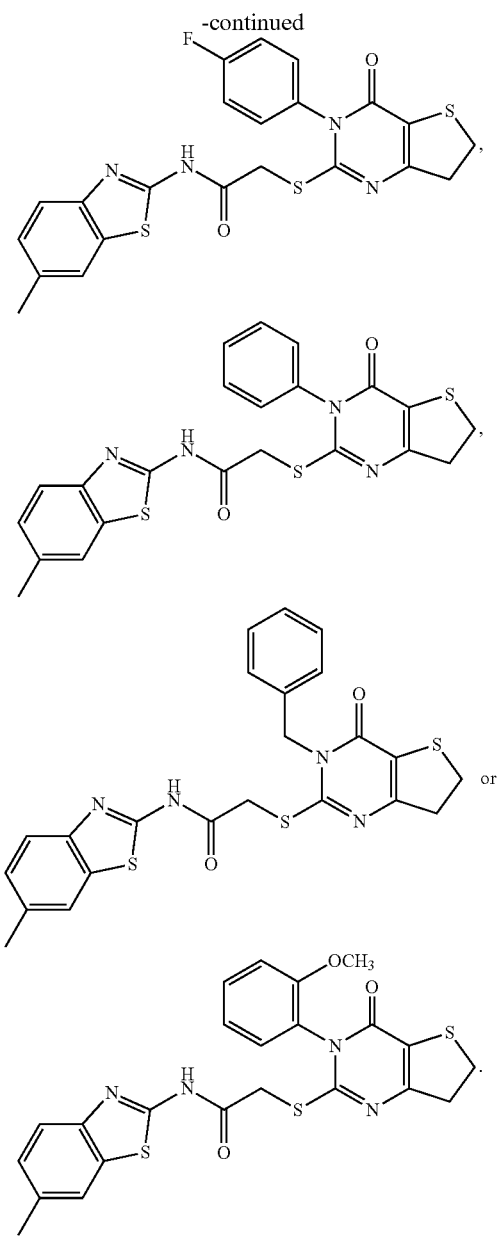

Another general aspect of the present invention contemplates a method of treating or preventing osteopetrosis in a patient comprising administering to the patient an effective amount of a compound disclosed herein. Such methods may further comprise administration of a second osteopetrosis-treating agent or a second osteopetrosis-preventing agent. Administration of the compound of interest may take place via a route selected from the group consisting of intravenously, intradermally, intraarterially, intraperitoneally, intralesionally, intracranially, intraarticularly, intranasally, topically, intramuscularly, subcutaneously, intraumbilically, orally, locally, via inhalation, via injection, via infusion, via continuous infusion, via localized perfusion bathing target cells directly, via a catheter, in cremes, in lipid compositions, or any combination thereof. Dosage amounts may range between, for example, about 1 μg/kg to about 100 mg/kg, or any range derivable therein.

Also contemplated by the present invention are methods of treating a degenerative disease in a patient comprising administering to the patient an effective amount of a compound disclosed herein. The degenerative disease may be, for example, type II diabetes or age-related impairment of tissue repair. Methods may further comprise administration of a second agent to treat the degenerative disease. Methods of administration may be selected from the group consisting of intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intramuscularly, subcutaneously, subconjunctival, intravesicularlly, mucosally, intrapericardially, intraumbilically, intraocularally, orally, locally, via inhalation, via injection, via infusion, via continuous infusion, via localized perfusion bathing target cells directly, via a catheter, via a lavage, in cremes, in lipid compositions, or any combination thereof. Dosage amounts may range between, for example, about 1 μg/kg to about 100 mg/kg, or any range derivable therein.

Also disclosed herein are methods of treating type II diabetes in a patient comprising administering to the patient an effective amount of a compound disclosed herein. Such methods may further comprise administration of a second agent to treat diabetes. Methods of administration may be selected from the group consisting of intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intramuscularly, subcutaneously, subconjunctival, intravesicularlly, mucosally, intrapericardially, intraumbilically, intraocularally, orally, locally, via inhalation, via injection, via infusion, via continuous infusion, via localized perfusion bathing target cells directly, via a catheter, via a lavage, in cremes, in lipid compositions, or any combination thereof. Dosage amounts may range between, for example, about 1 μg/kg to about 100 mg/kg, or any range derivable therein.

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2. Chemical structure and potency of IWR and IWP compounds. FIG. 2A. Structure and potency of IWR compounds. Two IWR compounds that differ by only a single methyl group and that share similar IC50's (as determined in L-Wnt-STF cells; upper right of graphs) were designated Class I compounds. The remaining three IWRs which share structural similarity (see also FIG. 10) were designated Class II compounds. FIG. 2B. Structure and potency of IWP compounds. All IWP compounds share structural similarity and IC50's with IWPs 2-4 sharing the same core structure (IWP-2) and differing only by either the presence of an additional fluoro or methoxy adduct (IWP-3 and IWP-4, respectively).

FIG. 4A Overexpression of the O-acyltransferase Porc but not the Wnt chaperone Evi counters the effects of IWP compounds on Wnt/b-catenin pathway activity in HEK293 cells. Wnt/b-catenin pathway activity was measured using the STF reporter as before in a 24 hr assay. FIG. 4B. Overexpression of Porc reverses the block in Wnt protein secretion induced by IWP compounds. Decreased cellular secretion of Wnt protein as measured using a Wnt3A-*Gaussia luciferase* fusion protein (see FIG. 1 and FIG. 9) that is decreased in IWP-treated cells is restored to control levels upon overexpression of Porc. FIG. 4C. IWP compounds inhibit lipidation of Wnt3A in a Porc-dependent manner. Lipidated Wnt3A protein, found in the detergent fraction of an established phase-separation assay used to detect modified Wnt proteins, is absent in IWP-treated cells. In cells overexpressing Porc, detergent-soluble Wnt3A is retained even in the presence of IWP-2. FIG. 4D. IWP compounds do no inhibit lipidation of ShhN protein. Using the same phase separation assay in FIG. 4C, no change in levels of detergent-soluble ShhN protein are observed in cells treated with an IWP compound. Note the slowest migrating form of ShhN (arrow) is absent in samples with ShhNC25S (which cannot be palmitoylated). FIG. 4E. Structure of biotinylated IWP-2 and its association with Porc. In order to generate an IWP-2 compound that could be affixed to a streptavidin-based solid support for biochemical studies (IWP-PEG-Biotin; see FIG. 13 for synthetic scheme), a linker and biotin group were attached to IWP-2 at the para position in the phenyl group that can likely accommodate modifications without affecting interaction with target protein (left; see FIG. 2C, IWP-3,4). Biotinylated IWP-2 or the control PEG-biotin group bound to streptavidin-coated sepharose beads was incubated with cellular lysate containing myc epitope-tagged Porc protein in the presence or absence of unmodified IWP-2 (right). Porc-Myc binding to IWP-2-beads can be competed with soluble unmodified IWP, as determined by Western blot analysis of material bound to beads. FIG. 4F. Model of IWP action. IWPs inhibit Porc function thereby rendering Wnt proteins non-functional.

FIG. 5A. IWR compounds block β-catenin accumulation induced by loss of APC tumor suppressor. Accumulation of β-catenin protein in mouse L-cells treated with APC siRNAs can be blocked by IWR-1. FIG. 5B. IWRs block aberrant Wnt/β-catenin pathway activity in the colorectal cancer (CRC) cells. Aberrant Wnt/β-catenin pathway activity in DLD-1 cells, CRC cells which harbor a loss-of-function mutation in APC, is abrogated by IWR compounds. Pathway activity was monitored using the STF reporter and normalized to RL control reporter as before. FIG. 5C. IWRs induce accumulation of Axin2 protein. Western blot analysis of proteins involved in regulating β-catenin levels in DLD-1 cells reveal accumulation of Axin2 protein in cells treated with IWR compounds with little change in expression levels of other pathway components. Note that the APC protein is truncated in these cells. FIG. 5D. Levels of β-catenin in CRC cells available for Wnt response are decreased in the presence of IWR compounds. Depletion of β-catenin bound to E-cadherin receptor proteins reveals levels of β-catenin available for Wnt pathway response in cells are decreased in cell treated with IWR. FIG. 5E. IWR stabilizes Axin2 protein. Rapid destruction of Axin2 protein is apparent in DLD-1 cells treated with the protein synthesis inhibitor cycloheximide. Cells treated with both cycloheximide and IWR-1 exhibit little turn-over of Axin2, suggesting that IWR compounds prevent destruction of Axin2 rather than induce its expression. FIG. 5F. Structure of biotinylated IWR-1 (IWR-1-PEG-B). FIG. 5G. Axin2 interacts with IWR-1-PEG-B. Lysates derived from cells transfected with either a control, Axin2, or Axin2 lacking the DAX C-terminal domain (Axin2ΔDAX) expression construct were incubated with IWR-1-PEG-B, strepavidin agarose beads, and either DMSO or IWR-1. FIG. 5H. A proposed model of IWR action. Addition of IWR to cells induces stabilization of Axin2 protein with consequential increase in β-catenin destruction.

FIG. 6A. IWR-1 prevents caudal fin regeneration in zebrafish. Adult zebrafish with resected caudal fins were placed in water containing DMSO carrier or IWR-1 (10 µM) for four days with replenishment of water and compounds every day. Consistent with inhibition of Wnt/β-catenin pathway response by IWR-1, fish treated with IWR-1 but not DMSO failed to regenerate fin tissue. Length of regenerated tissue is indicated by bar. FIG. 6B. IWR-1 blocks normal homeostatic renewal of the GI tract. Representative histological sections of mid-intestinal tissue from fish treated with carrier or IWR-1 (10 µM) for 8 or 14 days, then stained either with hematoxylin and eosin (H&E) or for BrdU incorporation. Loss of BrdU-labeled cells in the base of intestinal folds in IWR-1-treated fish (8 days; arrows) is followed by gross changes in intestinal tissue architecture after prolonged chemical exposure (14 days). FIG. 6C. Quantification of BrudU-labeled cells in the intestinal tract of control or IWR-1-treated fish. Histological sections as seen in FIG. 5B (middle column) were scored for the percentage of intestinal folds that contain BrdU-labeled cells. Four independent scorers analyzed sections from eight fish either from control and IWR-1 treated groups. Ratios provided represent the number of BrdU-labeled cells in the numerator and the number of intestinal folds scored in the denominator.

FIG. 7A. Growth-inhibitory effects of IWR and IWP compounds on cancerous cells. Cells derived from either lung or colon cancer, with known molecular changes that result in aberrant Wnt pathway response, were treated with increasing concentrations of either IWR-4 or IWP-1 for 6 days with medium and compounds replenished daily. Cell viability was measured using Cell-Titer Glo assays. FIG. 7B. Biochemical changes of Wnt pathway components in cancerous cells treated with either IWR or IWP compounds. Lysates from H460, or DLD-1 cells were treated with IWR or IWP and Western blotted for either Dvl2, Axin2, Axin1, or Actin. Whereas both cell lines express Axin2, Axin2 expression is absent in H460 cells. FIG. 7C. Genetic evidence for non-β-catenin dependent Wnt-mediated signalling in cancerous cells. Targeting of Porc using RNAi in lung cancer or CRC cell lines results in loss of clonal density cell growth whereas targeting β-catenin with a similar approach altered growth in only the DLD-1 cells. FIG. 7D. Inhibition of ligand-dependent and -independent Wnt pathway activities with IWR and IWP compounds: a proposed mechanism. Based on the proposed mechanism of action as shown in FIG. 7D, IWP and IWR compounds may inhibit pathway response that is driven in a ligand-dependent manner. Additionally, IWR compounds may block ligand-independent pathway responses such as those induced by loss of APC in colorectal cancer cells.

FIGS. 9A-C. IWR and IWP compounds specifically inhibit the Wnt/β-catenin pathway. FIG. 9A. Summary of results relating to IWR and IWP compounds from the screening process. Wnt pathway tests were performed in either cells responding to autonomously-produced Wnt protein (L-Wnt-STF cells) or exogenously provided Wnt in conditioned medium (HEK293 cells). FIG. 9B. IWP compounds inhibit Wnt3A secretion. Left: schematic of Wnt-*Gaussia* luciferase (Wnt-GL) fusion protein used to monitor levels of secreted Wnt protein in the cell medium. Right: levels of Wnt-GL but not GL secreted from cells treated with IWP compounds are decreased as compared to cells treated with carrier. The Wnt-GL protein elicits levels of Wnt/β-catenin pathway response similar to that of Wnt3a protein (data not shown). FIG. 9C. IWR and IWP compounds generally inhibit Wnt/β-catenin pathway response induced by Wnt proteins. Pathway activity induced by Wntl, Wnt2, or Wnt3a, and monitored using the STF reporter, is decreased in cells treated with either IWR-1 or IWP-2. FL activity was normalized to control RL activity as before.

FIGS. 11A-B. Synthetic scheme for IWP-2 and IWP-PEG-Biotin. Synthetic routes for IWP-2 (FIG. 11A) and IWP-PEG-Biotin (FIG. 11B) are shown.

FIGS. 12A-G. Synthetic scheme for IWR-1, IWR-1-PEG-B, and IWR-Cy3 compound. FIG. 12A. Synthetic route for IWR-1. Endo and exo diastereomers result depending on the starting material. FIG. 12B. Diagram of endo and exo IWR-1 structures. FIG. 12C. Normalized data regarding endo and exo IWR-1 on Wnt pathway response. FIG. 12D. Synthetic scheme for IWR-Cy3. FIG. 12E. Synthetic scheme for IWR-1-PEG-B. FIG. 12F. IWR-Cy3 and IWR-1-PEG-B retains activity against the Wnt/β-catenin pathway as measured using L-Wnt-STF cells. FIG. 12G. IWR-Cy3 and IWR-1-PEG B, like their parental compound IWR-1, inhibit accumulation of β-catenin in L-Wnt cells.

FIGS. 13A-C. A second-generation IWR compound with increased metabolic stability. As part of a search for IWR-related compounds with either greater potency or more favorable pharmacokinetic parameters that those observed for IWR-1, two (IWR-6 and IWR-7; FIG. 13A) were identified that retain ability to inhibit Wnt/β-catenin pathway response (FIG. 13B). One of these (IWR-7) also has a greater half-life than IWR-1 as measured using a hepatocyte co-culture assay (FIG. 13C).

FIG. 14A. IWP-2 does not induce destruction of Porcn. Levels of overexpressed Porcn increase in the presence of IWP-2. FIG. 14B. IWP-2 does not appear to alter localization of Porcn. FIG. 14C. Chemical structure and activity of several compounds related to IWP-2. IWP-2-v2 retains activity against the Wnt/β-catenin pathway as measured using the STF reporter (right), whereas IWP-2-v1 and -v3 do not.

FIG. 15 corresponds to compound IWR-8. FIG. 16 corresponds to compound IWR-9. FIG. 17 corresponds to compound IWR-10. FIG. 18 corresponds to compound IWR-11. FIG. 19 corresponds to compound IWR-12. FIG. 20 corresponds to compound IWR-13. FIG. 21 corresponds to compound IWR-14. FIG. 22 corresponds to compound IWR-15. FIG. 23 corresponds to compound IWR-18. FIG. 24 corresponds to compound IWR-19.

FIG. 25. Inhibition of Fin Regeneration in Zebrafish by IWRs. Arrows indicate the points of resection. The minimum inhibitory concentration of IWR-1 is 0.5 µM. Only partial inhibition of fin regeneration was observed with moderate inhibitors 13 and 43. The weak inhibitor 17 only retarded the growth of the tail fin (picture not shown).

DESCRIPTION OF ILLUSTRATIVE EMBODIMENTS

Figure 1:
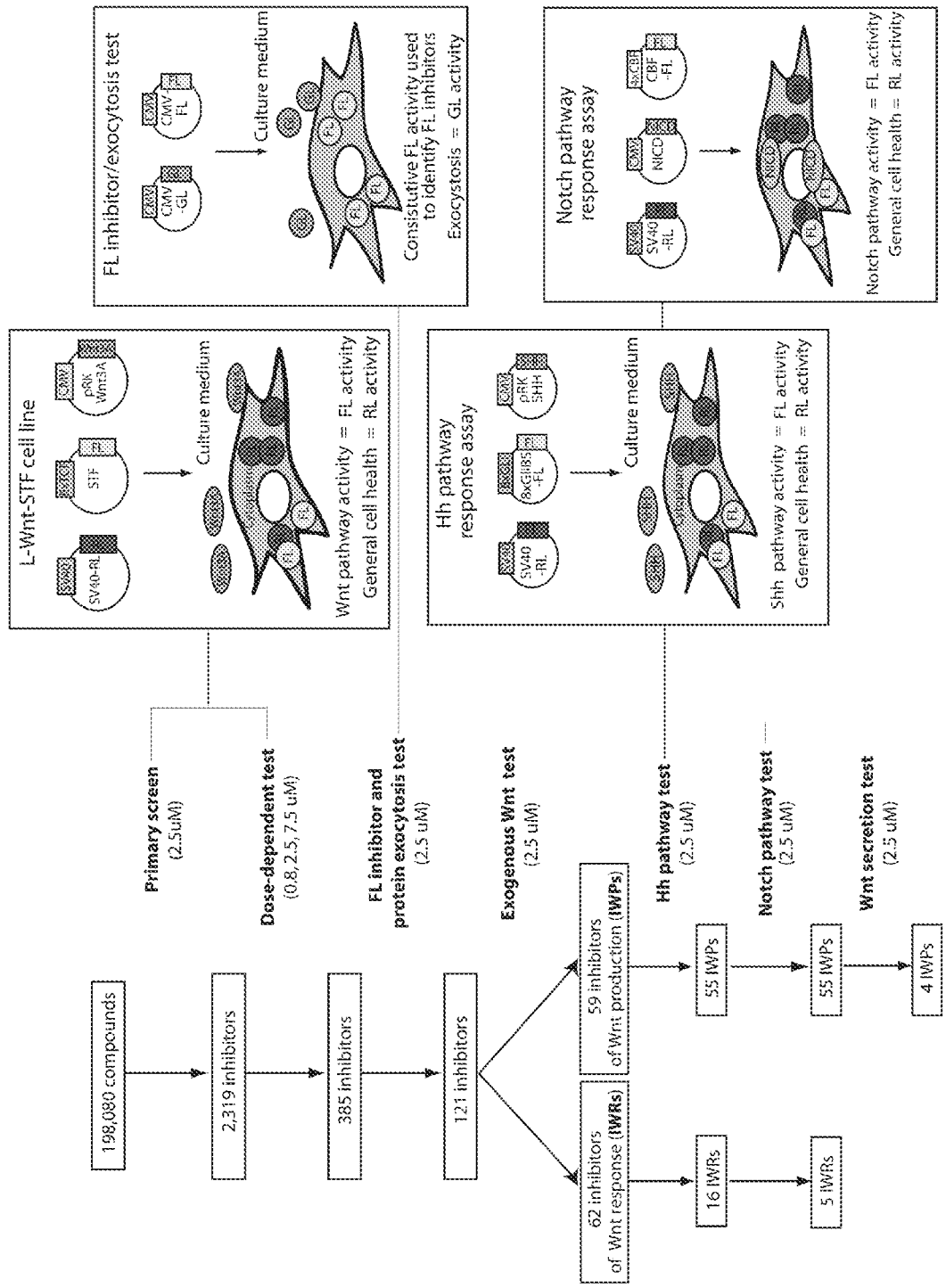
FIG. 1. Identification of small molecule antagonists of the Wnt/β-catenin signal transduction pathway. A ~200K chemical library from U.T. Southwestern (Dallas, Tex.) (UTSW) was screened using a cell line with constitutive Wnt/β-catenin pathway activity maintained by cell-autonomous Wnt3A protein production (L-Wnt-STF cells; Primary screen). Potential Wnt/β-catenin pathway antagonists were identified using a stably transfected Wnt-responsive firefly luciferase (FL) and control *Renilla* luciferase (RL) reporters. Approximately 1% of the compounds in the library that were scored as hits was tested again in a dose-dependent manner to identify the most potent compounds with minimal cellular toxicity (Dose-dependent test). Compounds that abrogated FL activity possibly by directly inhibition of FL activity, or that generally blocked cellular secretion of proteins were removed (FL inhibitor and exocytosis test). To separate compounds that either inhibit Wnt/β-catenin pathway response or Wnt3A protein production, compounds were tested in HEK293 cells using the same assay as described in the Primary screen with the exception that exogenous Wnt3A protein (provided in conditioned medium) was used to stimulate pathway response (Exogenous Wnt test). Compounds that retained their anti-pathway activity in this test were considered Inhibitors of Wnt response (IWRs), whereas those that did not were considered Inhibitors of Wnt production (IWPs). Compounds from both categories were tested for effects on two other signal transduction pathways (the Hh and Notch pathways) using cultured cell-based assays similar to those used to identify Wnt/β-catenin pathway antagonists (Hh and Notch pathway tests). Hh and Notch pathways were activated using either Shh or an activated Notch (NICD) cDNA constructs, respectively. Those compounds that minimally impacted these two pathways were considered to have specific activity for the Wnt/β-catenin pathway. Lastly, IWPs were directly tested for their ability to inhibit Wnt3A protein secretion (Wnt secretion test; see FIG. 9). Criteria for selecting hits are provided in FIG. 1. In the end, five IWRs and four IWPs with high specificity for attacking the Wnt/β-catenin pathway were selected for further analysis (FIG. 9). Concentration of compounds used in each test is noted. Insets show schematics of assays used in the screen and secondary tests with the utility of each luciferase read-out.

Small molecules that target Wnt-dependent signal transduction pathways, such as the Wnt/β-catenin pathway, have been identified. These small molecules reveal chemically-sensitive regulatory mechanisms within these signal transduction pathway that may be exploited by pharmacological means for medical use, such as regenerative and anti-cancer therapy.

I. THE WNT SIGNAL TRANSDUCTION PATHWAYS

The Wnt gene family encodes secreted ligand proteins that serve key roles in differentiation and development. This family comprises at least 15 vertebrate and invertebrate genes including the *Drosophila* segment polarity gene wingless and one of its vertebrate homologues, integrated from which the Wnt name derives. As noted above, the Wnt proteins appear to facilitate a number of developmental and homeostatic processes.

The Wnt signalling pathways comprises a number of proteins involved in the transduction of cellular responses to secreted Wnt/wingless signalling proteins. Wnt proteins that control "non-canonical" pathways, such as the Wnt/calcium and planar cell polarity pathways, induce cellular responses that are not-dependent upon β-catenin. In the Wnt/β-catenin pathway, the Frizzled receptor then activates Disheveled protein, which blocks the inhibiting action of Zeste-white-3 kinase (or GSK3β in vertebrates, Glycogen Synthase Kinase-3β) upon the Armadillo protein (a β-catenin protein). The β-catenin protein transduces the Wnt signal from the cytoplasm to the nucleus. In the absence of Wnt signalling, β-catenin is constitutively degraded by the proteasome and can be found in a multimeric complex with conductin (or axin), APC (*Adenomatous Polyposis Coli*) and GSK3β. APC mediates the binding of β-catenin to conductin and serves to activate the conductin protein. Conductin acts as a scaffold to assemble the components of the degradation pathway of β-catenin. GSK3β, a serine/threonine kinase, phosphorylates β-catenin, thus stimulating its degradation by the proteasome.

Upon Wnt signalling, GSK3β kinase is inactivated, leading to stabilization of the β-catenin protein. β-Catenin is then released from the multimeric complex and translocates into the nucleus. Once in the nucleus, β-catenin interacts with the LEF/TCF (Lymphoid Enhancer Factor/T-Cell Factor) family of HMG (High Mobility Group) box transcription factors. The LEF/TCF factors are stimulated through interaction with β-catenin to become potent transactivators of a number of genes including c-myc and cyclin D1.

II. THERAPEUTIC IMPLICATIONS OF WNT-CONTROLLED SIGNAL TRANSDUCTION PATHWAYS

As noted above, evidence suggests that targeting the Wnt-mediated signal transduction pathways would be therapeutically useful in a broad range of diseases (Barker and Clevers, 2006) (Veeman et al, 2003). Aged mice or mice that exhibit premature stem cell senescence that are treated with extracellular protein inhibitors of Wnt pathways exhibit improved regenerative capacity in various tissues (Brack et al., 2007; Liu et al., 2007). Mutations leading to constitutive activation of the Wnt pathway are critical events in a variety of human cancers including colon cancer, melanoma, hepatocellular carcinoma and others. The end result of constitutive activation of the Wnt/β-catenin pathway is a dramatic increase in the level of β-catenin protein in the cytoplasm. Inappropriate stabilization of β-catenin, leading to increased levels of the protein, can be caused by mutations in a variety of proteins in the Wnt signalling pathway. Blockade of the Wnt/β-catenin pathway in a variety of cancers using either genetic or chemical approaches been shown to abrogate aberrant cell growth (Barker and Clevers, 2006). Furthermore, inhibition of this pathway may directly influence the cells that sustain cancer cell growth and enable metastasis, and that are thought to be resistant to traditional chemotherapeutic agents (Ailles and Weissman, 2007).

Figure 6:
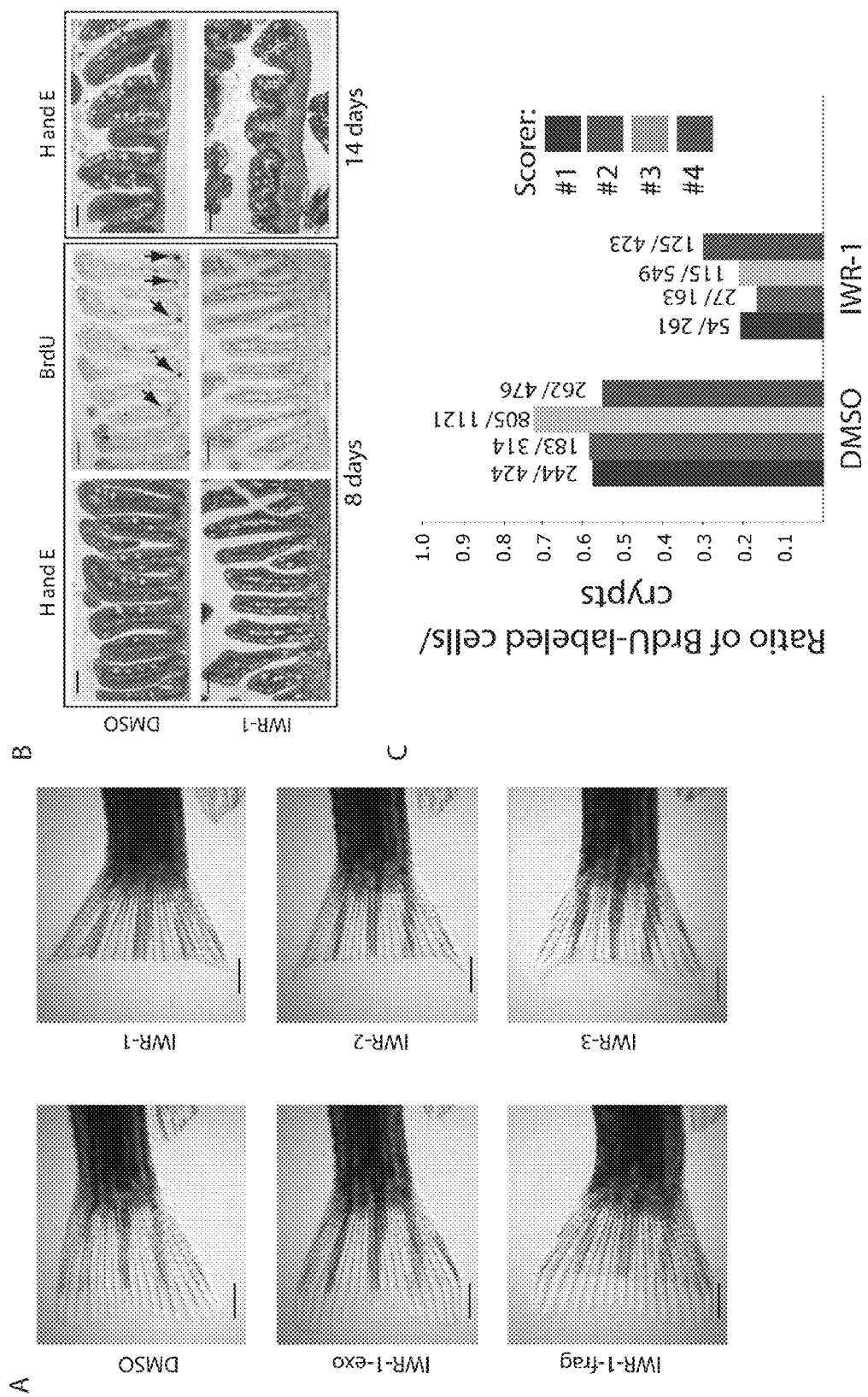
FIGS. 6A-C. Chemical inhibition of the Wnt/β-catenin pathway in regeneration and cancer.

The pervasive influence of the Wnt proteins in tissue homeostasis and tumorigenesis suggests areas such as regenerative medicine and anti-cancer therapy may benefit from therapies that target this pathway. Achieving transient repression of pathological Wnt response without incurring permanent damage to normal stem cell function is a key anticancer therapeutic goal. We tested for the ability of zebrafish to resume regenerative processes following a chemically induced blockade of fin regrowth. Fish with resected caudal fins that were bred in water containing IWR-1 for 7 d were able to regenerate tissue to nearly normal levels after chemical removal, which suggests that transient inhibition of Wnt/β-catenin response does not permanently alter the ability of stem cells to self-renew (FIG. 6a).

Aberrant Wnt-mediated pathway responses, sustained by genetic changes that result either in altered Wnt ligand activity or in altered functioning of pathway regulators, have been associated with a broad range of cancers. See Clevers, 2006 and Polakis, 2007, both of which are incorporated herein by reference. Notably, more than 90% of colorectal cancer (CRC) tumors harbor a loss-of-function mutation in APC, a suppressor of the Wnt/b-catenin pathway. See Sjoblom et al., 2006, which is incorporated herein by reference. The ability of IWR compounds to stabilize Axin proteins and induce β-catenin destruction even in the absence of normal APC protein function suggests that they may block aberrant cell growth supported by hyperactivation of Wnt/β-catenin responses.

Indeed, IWR compounds are able to inhibit aberrant Wnt/β-catenin activity as a consequence of Apc loss in both mouse L cells (using Apc small interfering RNAs) and DLD-1 colorectal cancer cells (that harbor a loss-of-function mutation in APC). The ability of IWR-3 to mimic the cell growth effects of β-catenin siRNAs in several cancer cell lines that exhibit differences in growth dependency on Wnt/β-catenin pathway activity was also tested. Notably, IWR-3 mimicked the effects of b-catenin siRNAs on the growth of cells derived from cancers of the colon (DLD-1) and prostate (DU145) but not lung (H460), which suggests that IWR-3 successfully targeted the Wnt/b-catenin pathway in these cells. Indeed, overexpression of b-catenin can overcome the effects of IWR-3 on DLD-1 cell growth.

Aberrant transcriptional induction of Wnt/b-catenin target genes is typically observed in CRC cells that harbor loss-of-function mutations in the APC tumor suppressor. Consistent with the ability of IWR compounds to inhibit cancerous Wnt/β-catenin pathway responses, a decrease in the expression of Axin2 in DLD-1 cells after exposure to IWR-1 for 2 h was observed. Thus, Axin protein stability can be chemically controlled in order to suppress cancerous Wnt/b-catenin activity, as demonstrated by IWR compounds. See Chen et al. (2007), which is incorporated herein by reference.

III. WNT PROTEIN SIGNALLING INHIBITORS

Accordingly, the present invention provides small molecules that inhibit the Wnt protein signalling pathway.

Examples of such compounds include IWR-1 and IWR-2, as shown here along with their respective in vitro activities:

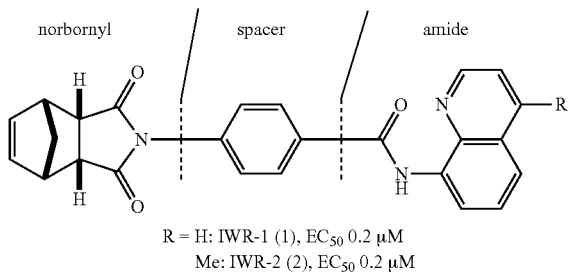

R = H: IWR-1 (1), EC$_{50}$ 0.2 μM
Me: IWR-2 (2), EC$_{50}$ 0.2 μM

Tables 1 and 2 provides further examples of such compounds, as well as their activities as determined by a luciferase-based reporter assay that measures Wnt/β-catenin-dependent transcriptional response.

TABLE 1

Examples of Small Molecule Wnt Inhibitors.

| Compounds | R | EC50 (μM) |
|---|---|---|
| 3 | 7-methylquinolin-8-yl | 0.8 |
| 4 | 5,6,7,8-tetrahydroquinolin-8-yl | 10 |
| 5 | 2-methoxyphenyl | 1 |
| 6 | phenyl | >25 |
| 7 | 2-fluorophenyl | >25 |
| 8 | 2-chlorophenyl | >25 |
| 9 | 2-bromophenyl | >25 |
| 10 | 3-fluorophenyl | >25 |
| 11 | 3-chlorophenyl | >25 |
| 12 | 3-bromophenyl | 9 |
| 13 | 4-fluorophenyl | 4 |
| 14 | 4-chlorophenyl | 3 |
| 15 | 4-bromophenyl | 1 |
| 16 | 2,3-difluorophenyl | >25 |
| 17 | 2,4-difluorophenyl | 9 |
| 18 | 2,4-dichlorophenyl | 10 |
| 19 | 2,4-dibromophenyl | >25 |
| 20 | 2,5-difluorophenyl | >25 |
| 21 | 2,6-difluorophenyl | >25 |
| 22 | 3,4-difluorophenyl | 3 |
| 23 | 3,4-dichlorophenyl | 5 |
| 24 | 3,4-dibromophenyl | 10 |
| 25 | 3,5-difluorophenyl | >25 |
| 26 | 2-(trifluoromethyl)phenyl | >25 |
| 27 | 3-(trifluoromethyl)phenyl | 20 |
| 28 | 4-(trifluoromethyl)phenyl | >25 |
| 29 | benzyl | 20 |
| 30 | (2-pyridyl)methyl | >25 |
| 31 | (3-pyridyl)methyl | >25 |
| 32 | (4-pyridyl)methyl | 10 |
| 33 | trans-(2-methoxy)cyclohexyl | 2 |
| 34 | trans-(2-hydroxy)cyclohexyl | >25 |
| 35 | cyclohexyl | >25 |

TABLE 2

Further Examples of Small Molecule Wnt Inhibitors.

| Compounds | R | R' | Ar | EC$_{50}$ (μM) |
|---|---|---|---|---|
| 36 | a | 2-chloro | quinolin-8-y | >25 |
| 37 | a | 2-methyl | quinolin-8-y | >25 |
| 38 | a | 2-methoxy | quinolin-8-y | >25 |
| 39 | a | 3-chloro | quinolin-8-y | 1 |
| 40 | a | 3-methyl | quinolin-8-y | 2 |
| 41 | a | 3-methoxy | quinolin-8-y | >25 |
| 42 | b | — | quinolin-8-yl | >25 |
| 43 | c | — | quinolin-8-yl | 0.4 |
| 44 | c | — | 4-methylquinolin-8-yl | 1 |
| 45 | c | — | 7-methylquinolin-8-yl | 1 |
| 46 | d | — | quinolin-8-yl | >25 |
| 47 | d | — | 4-methylquinolin-8-yl | >25 |
| 48 | d | — | 7-methylquinolin-8-yl | 10 |
| 49 | e | — | quinolin-8-yl | 10 |

Still further examples of Wnt signaling inhibitors are compounds 50, 51 and 52:

50 EC$_{50}$ > 25 μM

51 EC$_{50}$ = 5 μM

52 EC$_{50}$ = 0.2 μM

Yet still further examples include:
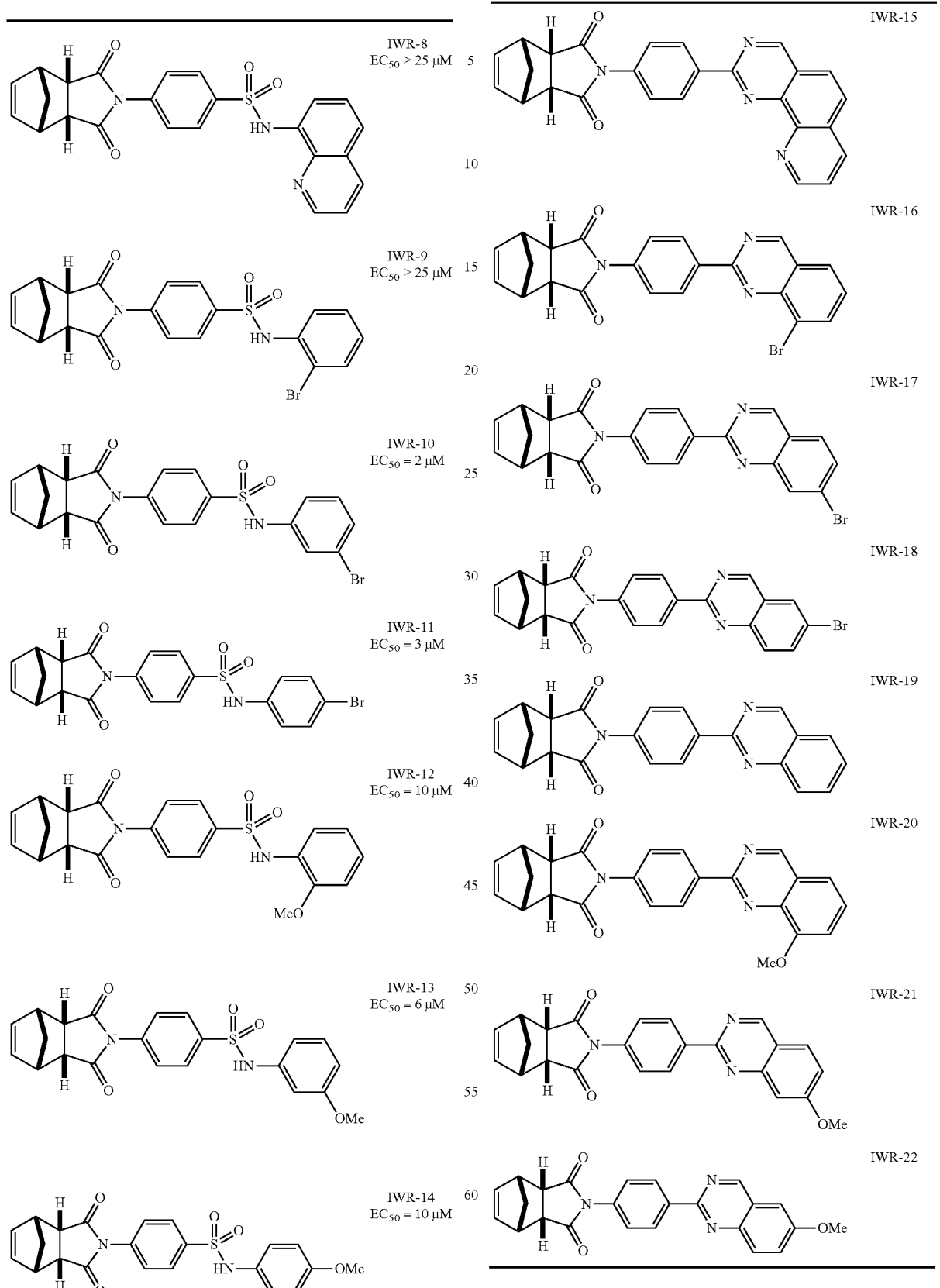
Some of the compounds above were made using the methods provided by Chen et al. (2009), which is incorporated by reference in its entirety. Some small molecule Wnt signaling inhibitors disclosed herein were made by the methods outlined below, in FIGS. 11 and 12, and in the Examples section. Variations of these methods provided further small molecule Wnt signaling inhibitors. Exemplary characterization data is also provided in the Examples section.

Some of the small molecule Wnt signaling inhibitors disclosed herein are novel. Of these, compounds IWR-8 through IWR-14 can be made according to the following scheme:

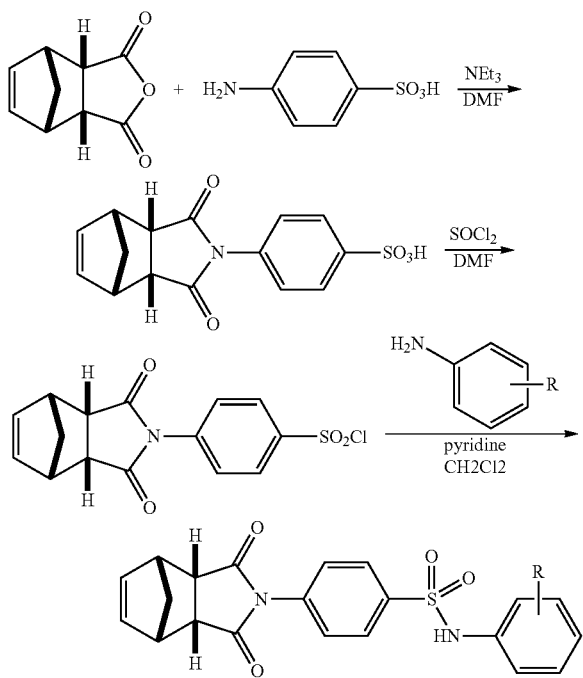

Some of the compounds disclosed herein, e.g., IWR-15 through IWR-22, may be made according to the following scheme:

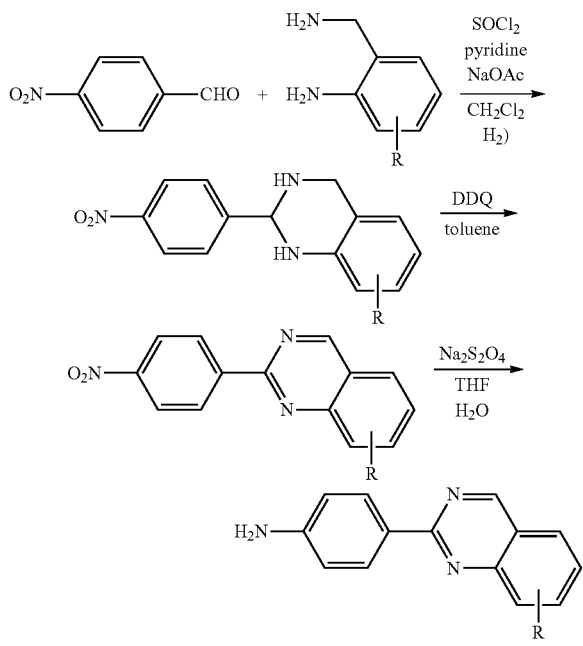

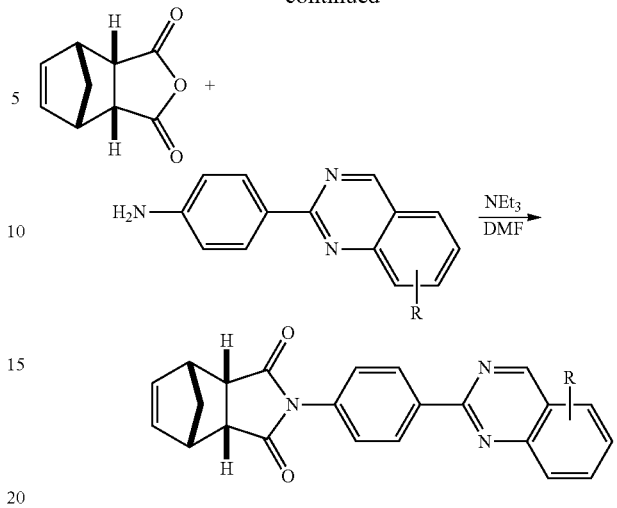

It is noted that compounds IWR-16, IWR-17, IWR-20, IWR-21 and IWR-22 are prophetic and have neither been made nor tested.

All of these methods can be further modified and optimized using the principles and techniques of organic chemistry as applied by a person skilled in the art. Such principles and techniques are taught, for example, in March's Advanced Organic Chemistry: Reactions, Mechanisms, and Structure (2007), which is incorporated by reference herein.

IV. DEFINITIONS

As used herein, "Wnt protein signalling pathway" refers to the pathways by which binding of the Wnt protein to extracellular receptors is either translated into the nucleus and results in transcriptional activation of a variety of genes, or otherwise results in biochemical changes that influence cell behavior. The Wnt protein signalling pathways involve a variety of proteins including Frizzled, Disheveled, Axin, APC, GSK3β, β-catenin, LEF/TCF transcription factors, etc. Cells from many different species express homologs of the proteins involved in Wnt protein signalling pathways and accordingly have functionally equivalent Wnt protein signalling pathways.

As used herein, a "Wnt protein signalling inhibitor" is an organopharmaceutical (that is, a small organic molecule) that inhibits Wnt protein signalling activity. Wnt protein signalling inhibitors typically have a molecular weight of about 1000 g/mol or less.

As used herein, "a method of inhibiting Wnt response" refers to methods of inhibiting known biochemical events associated with production of functional Wnt proteins or with cellular responses to Wnt proteins. As discussed herein, small organic molecules may inhibit Wnt response in accordance with this definition.

As used herein, "hydrogen" means —H; "hydroxy" means —OH; "oxo" means =O; "halo" means independently —F, —Cl, —Br or —I; "amino" means —NH$_2$ (see below for definitions of groups containing the term amino, e.g., alkylamino); "hydroxyamino" means —NHOH; "nitro" means —NO$_2$; imino means =NH (see below for definitions of groups containing the term imino, e.g., alkylamino); "cyano" means —CN; "azido" means —N$_3$; "phosphate" means —OP(O)(OH)$_2$; "mercapto" means —SH; "thio" means =S; "sulfonamido" means —NHS(O)$_2$— (see below for definitions of groups containing the term sulfonamido, e.g., alkyl-sulfonamido); "sulfonyl" means —S(O)$_2$— (see below for definitions of groups containing the term sulfonyl, e.g., alkylsulfonyl); "sulfinyl" means —S(O)— (see below for definitions of groups containing the term sulfinyl, e.g., alkylsulfinyl); and "silyl" means —SiH$_3$ (see below for definitions of group(s) containing the term silyl, e.g., alkylsilyl).

For the groups below, the following parenthetical subscripts further define the groups as follows: "(Cn)" defines the exact number (n) of carbon atoms in the group. "(C≤n)" defines the maximum number (n) of carbon atoms that can be in the group, with the minimum number of carbon atoms in such at least one, but otherwise as small as possible for the group in question. E.g., it is understood that the minimum number of carbon atoms in the group "alkenyl$_{(C≤8)}$" is 2. For example, "alkoxy$_{(C≤10)}$" designates those alkoxy groups having from 1 to 10 carbon atoms (e.g., 1, 2, 3, 4, 5, 6, 7, 8, 9, or 10, or any range derivable therein (e.g., 3-10 carbon atoms)). (Cn-n') defines both the minimum (n) and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3-10 carbon atoms)).

The term "alkyl" when used without the "substituted" modifier refers to a non-aromatic monovalent group with a saturated carbon atom as the point of attachment, a linear or branched, cyclo, cyclic or acyclic structure, no carbon-carbon double or triple bonds, and no atoms other than carbon and hydrogen. The groups, —CH$_3$ (Me), —CH$_2$CH$_3$ (Et), —CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neo-pentyl), cyclobutyl, cyclopentyl, cyclohexyl, and cyclohexylmethyl are non-limiting examples of alkyl groups. The term "substituted alkyl" refers to a non-aromatic monovalent group with a saturated carbon atom as the point of attachment, a linear or branched, cyclo, cyclic or acyclic structure, no carbon-carbon double or triple bonds, and at least one atom independently selected from the group consisting of N, O, F, Cl, Br, I, Si, P, and S. The following groups are non-limiting examples of substituted alkyl groups: —CH$_2$OH, —CH$_2$Cl, —CH$_2$Br, —CH$_2$SH, —CF$_3$, —CH$_2$CN, —CH$_2$C(O)H, —CH$_2$C(O)OH, —CH$_2$C(O)O CH$_3$, —CH$_2$C(O)NH$_2$, —CH$_2$C(O)NHCH$_3$, —CH$_2$C(O)CH$_3$, —CH$_2$OCH$_3$, —CH$_2$OCH$_2$CF$_3$, —CH$_2$OC(O)CH$_3$, —CH$_2$NH$_2$, —CH$_2$NHCH$_3$, —CH$_2$N(CH$_3$)$_2$, —CH$_2$CH$_2$Cl, —CH$_2$CH$_2$OH, —CH$_2$CF$_3$, —CH$_2$CH$_2$OC(O)CH$_3$, —CH$_2$CH$_2$NHCO$_2$C(CH$_3$)$_3$, and —CH$_2$Si(CH$_3$)$_3$.

The term "alkanediyl" when used without the "substituted" modifier refers to a non-aromatic divalent group, wherein the alkanediyl group is attached with two σ-bonds, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, —CH$_2$CH$_2$CH$_2$—, and

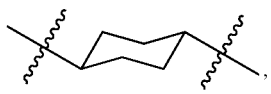 [SMILES: *C1CCC(*)CC1]

are non-limiting examples of alkanediyl groups. The term "substituted alkanediyl" refers to a non-aromatic monovalent group, wherein the alkynediyl group is attached with two σ-bonds, with one or two saturated carbon atom(s) as the point(s) of attachment, a linear or branched, cyclo, cyclic or acyclic structure, no carbon-carbon double or triple bonds, and at least one atom independently selected from the group consisting of N, O, F, Cl, Br, I, Si, P, and S. The following groups are non-limiting examples of substituted alkanediyl groups: —CH(F)—, —CF$_2$—, —CH(Cl)—, —CH(OH)—, —CH(OCH$_3$)—, and —CH$_2$CH(Cl)—.

The term "alkenyl" when used without the "substituted" modifier refers to a monovalent group with a nonaromatic carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH═CH$_2$ (vinyl), —CH═CHCH$_3$, —CH═CHCH$_2$CH$_3$, —CH$_2$CH═CH$_2$ (allyl), —CH$_2$CH═CHCH$_3$, and —CH═CH—C$_6$H$_5$. The term "substituted alkenyl" refers to a monovalent group with a nonaromatic carbon atom as the point of attachment, at least one nonaromatic carbon-carbon double bond, no carbon-carbon triple bonds, a linear or branched, cyclo, cyclic or acyclic structure, and at least one atom independently selected from the group consisting of N, O, F, Cl, Br, I, Si, P, and S. The groups, —CH═CHF, —CH═CHCl and —CH═CHBr, are non-limiting examples of substituted alkenyl groups.

The term "alkenediyl" when used without the "substituted" modifier refers to a non-aromatic divalent group, wherein the alkenediyl group is attached with two σ-bonds, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH═CH—, —CH═C(CH$_3$)CH$_2$—, —CH═CHCH$_2$—, and

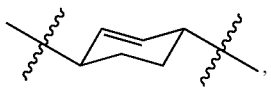 [SMILES: *C1C=CC(*)CC1]

are non-limiting examples of alkenediyl groups. The term "substituted alkenediyl" refers to a non-aromatic divalent group, wherein the alkenediyl group is attached with two σ-bonds, with two carbon atoms as points of attachment, a linear or branched, cyclo, cyclic or acyclic structure, at least one nonaromatic carbon-carbon double bond, no carbon-carbon triple bonds, and at least one atom independently selected from the group consisting of N, O, F, Cl, Br, I, Si, P, and S. The following groups are non-limiting examples of substituted alkenediyl groups: —CF═CH—, —C(OH)═CH—, and —CH$_2$CH═C(Cl)—.

The term "alkynyl" when used without the "substituted" modifier refers to a monovalent group with a nonaromatic carbon atom as the point of attachment, a linear or branched, cyclo, cyclic or acyclic structure, at least one carbon-carbon triple bond, and no atoms other than carbon and hydrogen. The groups, —C≡CH, —C≡CCH$_3$, —C≡CC$_6$H$_5$ and —CH$_2$C≡CCH$_3$, are non-limiting examples of alkynyl groups. The term "substituted alkynyl" refers to a monovalent group with a nonaromatic carbon atom as the point of attachment and at least one carbon-carbon triple bond, a linear or branched, cyclo, cyclic or acyclic structure, and at least one atom independently selected from the group consisting of N, O, F, Cl, Br, I, Si, P, and S. The group, —C≡CSi(CH$_3$)$_3$, is a non-limiting example of a substituted alkynyl group.

The term "alkynediyl" when used without the "substituted" modifier refers to a non-aromatic divalent group, wherein the alkynediyl group is attached with two σ-bonds, with two carbon atoms as points of attachment, a linear or branched, cyclo, cyclic or acyclic structure, at least one carbon-carbon triple bond, and no atoms other than carbon and hydrogen. The groups, —C≡C—, —C≡CCH$_2$—, and —C≡CCH(CH$_3$)— are non-limiting examples of alkynediyl groups. The term "substituted alkynediyl" refers to a non-aromatic divalent group, wherein the alkynediyl group is attached with two σ-bonds, with two carbon atoms as points of attachment, a linear or branched, cyclo, cyclic or acyclic structure, at least one carbon-carbon triple bond, and at least one atom independently selected from the group consisting of N, O, F, Cl, Br, I, Si, P, and S. The groups —C≡CCFH— and —C≡CHCH(Cl)— are non-limiting examples of substituted alkynediyl groups.

The term "aryl" when used without the "substituted" modifier refers to a monovalent group with an aromatic carbon atom as the point of attachment, said carbon atom forming part of a six-membered aromatic ring structure wherein the ring atoms are all carbon, and wherein the monovalent group consists of no atoms other than carbon and hydrogen. Non-limiting examples of aryl groups include phenyl (Ph), methylphenyl, (dimethyl)phenyl, —C$_6$H$_4$CH$_2$CH$_3$ (ethylphenyl), —C$_6$H$_4$CH$_2$CH$_2$CH$_3$ (propylphenyl), —C$_6$H$_4$CH(CH$_3$)$_2$, —C$_6$H$_4$CH(CH$_2$)$_2$, —C$_6$H$_3$(CH$_3$)CH$_2$CH$_3$ (methylethylphenyl), —C$_6$H$_4$CH═CH$_2$ (vinylphenyl), —C$_6$H$_4$CH═CHCH$_3$, —C$_6$H$_4$C≡CH, —C$_6$H$_4$C≡CCH$_3$, naphthyl, and the monovalent group derived from biphenyl. The term "substituted aryl" refers to a monovalent group with an aromatic carbon atom as the point of attachment, said carbon atom forming part of a six-membered aromatic ring structure wherein the ring atoms are all carbon, and wherein the monovalent group further has at least one atom independently selected from the group consisting of N, O, F, Cl, Br, I, Si, P, and S. Non-limiting examples of substituted aryl groups include the groups: —C$_6$H$_4$F, —C$_6$H$_4$Cl, —C$_6$H$_4$Br, —C$_6$H$_4$I, —C$_6$H$_4$OH, —C$_6$H$_4$OCH$_3$, —C$_6$H$_4$OCH$_2$CH$_3$, C$_6$H$_4$OC(O)CH$_3$, —C$_6$H$_4$NH$_2$, —C$_6$H$_4$NHCH$_3$, —C$_6$H$_4$N(CH$_3$)$_2$, —C$_6$H$_4$CH$_2$OH, —C$_6$H$_4$CH$_2$OC(O)CH$_3$, —C$_6$H$_4$CH$_2$NH$_2$, —C$_6$H$_4$CF$_3$, —C$_6$H$_4$CN, —C$_6$H$_4$CHO, —C$_6$H$_4$CHO, —C$_6$H$_4$C(O)CH$_3$, C$_6$H$_4$C(O)C$_6$H$_5$, C$_6$H$_4$CO$_2$H, —C$_6$H$_4$CO$_2$CH$_3$, —C$_6$H$_4$CONH$_2$, —C$_6$H$_4$CONHCH$_3$, and —C$_6$H$_4$CON(CH$_3$)$_2$.

The term "arenediyl" when used without the "substituted" modifier refers to a divalent group, wherein the arenediyl group is attached with two σ-bonds, with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. Non-limiting examples of arenediyl groups include:

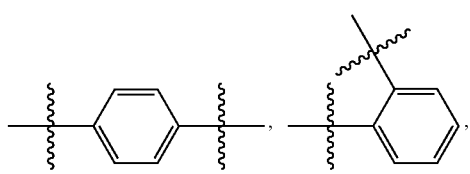

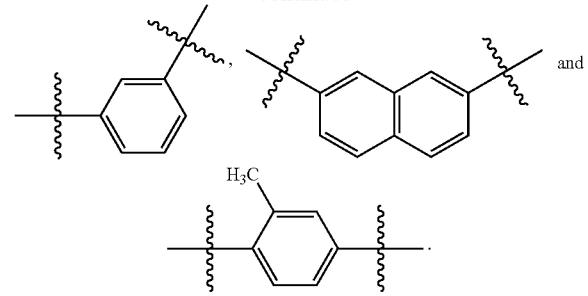

The term "substituted arenediyl" refers to a divalent group, wherein the arenediyl group is attached with two σ-bonds, with two aromatic carbon atoms as points of attachment, said carbon atoms forming part of one or more six-membered aromatic rings structure(s), wherein the ring atoms are all carbon, and wherein the divalent group further has at least one atom independently selected from the group consisting of N, O, F, Cl, Br, I, Si, P, and S.

The term "aralkyl" when used without the "substituted" modifier refers to the monovalent group-alkanediyl-aryl, in which the terms alkanediyl and aryl are each used in a manner consistent with the definitions provided above. Non-limiting examples of aralkyls are: phenylmethyl (benzyl, Bn), 1-phenyl-ethyl, 2-phenyl-ethyl, indenyl and 2,3-dihydro-indenyl, provided that indenyl and 2,3-dihydro-indenyl are only examples of aralkyl in so far as the point of attachment in each case is one of the saturated carbon atoms. When the term "aralkyl" is used with the "substituted" modifier, either one or both the alkanediyl and the aryl is substituted. Non-limiting examples of substituted aralkyls are: (3-chlorophenyl)-methyl, 2-oxo-2-phenyl-ethyl (phenylcarbonylmethyl), 2-chloro-2-phenyl-ethyl, chromanyl where the point of attachment is one of the saturated carbon atoms, and tetrahydroquinolinyl where the point of attachment is one of the saturated atoms.

The term "heteroaryl" when used without the "substituted" modifier refers to a monovalent group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the monovalent group consists of no atoms other than carbon, hydrogen, aromatic nitrogen, aromatic oxygen and aromatic sulfur. Non-limiting examples of aryl groups include acridinyl, furanyl, imidazoimidazolyl, imidazopyrazolyl, imidazopyridinyl, imidazopyrimidinyl, indolyl, indazolinyl, methylpyridyl, oxazolyl, phenylimidazolyl, pyridyl, pyrrolyl, pyrimidyl, pyrazinyl, quinolyl, quinazolyl, quinoxalinyl, tetrahydroquinolinyl, thienyl, triazinyl, pyrrolopyridinyl, pyrrolopyrimidinyl, pyrrolopyrazinyl, pyrrolotriazinyl, pyrroloimidazolyl, chromenyl (where the point of attachment is one of the aromatic atoms), and chromanyl (where the point of attachment is one of the aromatic atoms). The term "substituted heteroaryl" refers to a monovalent group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the monovalent group further has at least one atom independently selected from the group consisting of non-aromatic nitrogen, non-aromatic oxygen, non aromatic sulfur F, Cl, Br, I, Si, and P.

The term "heteroarenediyl" when used without the "substituted" modifier refers to a divalent group, wherein the heteroarenediyl group is attached with two σ-bonds, with an aromatic carbon atom or nitrogen atom as the point of attachment, said carbon atom or nitrogen atom two aromatic atoms as points of attachment, said carbon atoms forming part of one or more six-membered aromatic ring structure(s) wherein the ring atoms are all carbon, and wherein the monovalent group consists of no atoms other than carbon and hydrogen. Non-limiting examples of heteroarenediyl groups include:

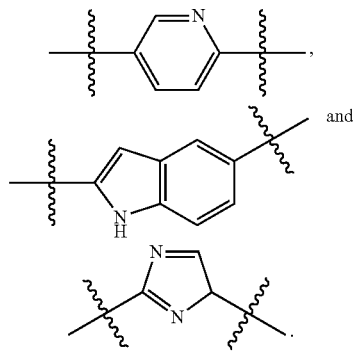

The term "substituted heteroarenediyl" refers to a divalent group, wherein the heteroarenediyl group is attached with two σ-bonds, with two aromatic carbon atoms as points of attachment, said carbon atoms forming part of one or more six-membered aromatic rings structure(s), wherein the ring atoms are all carbon, and wherein the divalent group further has at least one atom independently selected from the group consisting of N, O, F, Cl, Br, I, Si, P, and S.

The term "heteroaralkyl" when used without the "substituted" modifier refers to the monovalent group -alkanediyl-heteroaryl, in which the terms alkanediyl and heteroaryl are each used in a manner consistent with the definitions provided above. Non-limiting examples of aralkyls are: pyridylmethyl, and thienylmethyl. When the term "heteroaralkyl" is used with the "substituted" modifier, either one or both the alkanediyl and the heteroaryl is substituted.

The term "acyl" when used without the "substituted" modifier refers to a monovalent group with a carbon atom of a carbonyl group as the point of attachment, further having a linear or branched, cyclo, cyclic or acyclic structure, further having no additional atoms that are not carbon or hydrogen, beyond the oxygen atom of the carbonyl group. The groups, —CHO, —C(O)CH$_3$ (acetyl, Ac), —C(O)CH$_2$CH$_3$, —C(O) CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)C$_6$H$_4$CH$_2$CH$_3$, —COC$_6$H$_3$(CH$_3$)$_2$, and —C(O)CH$_2$C$_6$H$_5$, are non-limiting examples of acyl groups. The term "acyl" therefore encompasses, but is not limited to groups sometimes referred to as "alkyl carbonyl" and "aryl carbonyl" groups. The term "substituted acyl" refers to a monovalent group with a carbon atom of a carbonyl group as the point of attachment, further having a linear or branched, cyclo, cyclic or acyclic structure, further having at least one atom, in addition to the oxygen of the carbonyl group, independently selected from the group consisting of N, O, F, Cl, Br, I, Si, P, and S. The groups, —C(O) CH$_2$CF$_3$, —CO$_2$H (carboxyl), —CO$_2$CH$_3$ (methylcarboxyl), —CO$_2$CH$_2$CH$_3$, —CO$_2$CH$_2$CH$_2$CH$_3$, —CO$_2$C$_6$H$_5$, —CO$_2$CH(CH$_3$)$_2$, —CO$_2$CH(CH$_2$)$_2$, —C(O)NH$_2$ (carbamoyl), —C(O)NHCH$_3$, —C(O)NHCH$_2$CH$_3$, —CONHCH (CH$_3$)$_2$, —CONHCH(CH$_2$)$_2$, —CON(CH$_3$)$_2$, —CONHCH$_2$CF$_3$, —CO-pyridyl, —CO-imidazoyl, and —C(O)N$_3$, are non-limiting examples of substituted acyl groups. The term "substituted acyl" encompasses, but is not limited to, "heteroaryl carbonyl" groups.

The term "alkylidene" when used without the "substituted" modifier refers to the divalent group =CRR', wherein the alkylidene group is attached with one σ-bond and one π-bond, in which R and R' are independently hydrogen, alkyl, or R and R' are taken together to represent alkanediyl. Non-limiting examples of alkylidene groups include: =CH$_2$, =CH(CH$_2$CH$_3$), and =C(CH$_3$)$_2$. The term "substituted alkylidene" refers to the group =CRR', wherein the alkylidene group is attached with one σ-bond and one π-bond, in which R and R' are independently hydrogen, alkyl, substituted alkyl, or R and R' are taken together to represent a substituted alkanediyl, provided that either one of R and R' is a substituted alkyl or R and R' are taken together to represent a substituted alkanediyl.

The term "alkoxy" when used without the "substituted" modifier refers to the group —OR, in which R is an alkyl, as that term is defined above. Non-limiting examples of alkoxy groups include: —OCH$_3$, —OCH$_2$CH$_3$, —OCH$_2$CH$_2$CH$_3$, —OCH(CH$_3$)$_2$, —OCH(CH$_2$)$_2$, —O-cyclopentyl, and —O-cyclohexyl. The term "substituted alkoxy" refers to the group —OR, in which R is a substituted alkyl, as that term is defined above. For example, —OCH$_2$CF$_3$ is a substituted alkoxy group.

Similarly, the terms "alkenyloxy", "alkynyloxy", "aryloxy", "aralkoxy", "heteroaryloxy", "heteroaralkoxy" and "acyloxy", when used without the "substituted" modifier, refers to groups, defined as —OR, in which R is alkenyl, alkynyl, aryl, aralkyl, heteroaryl, heteroalkyl and acyl, respectively, as those terms are defined above. When any of the terms alkenyloxy, alkynyloxy, aryloxy, aralkyloxy and acyloxy is modified by "substituted," it refers to the group —OR, in which R is substituted alkenyl, alkynyl, aryl, aralkyl, heteroaryl, heteroalkyl and acyl, respectively.

The term "alkylamino" when used without the "substituted" modifier refers to the group —NHR, in which R is an alkyl, as that term is defined above. Non-limiting examples of alkylamino groups include: —NHCH$_3$, —NHCH$_2$CH$_3$, —NHCH$_2$CH$_2$CH$_3$, —NHCH(CH$_3$)$_2$, —NHCH(CH$_2$)$_2$, —NHCH$_2$CH$_2$CH$_2$CH$_3$, —NHCH(CH$_3$)CH$_2$CH$_3$, —NHCH$_2$CH(CH$_3$)$_2$, —NHC(CH$_3$)$_3$, —NH-cyclopentyl, and —NH-cyclohexyl. The term "substituted alkylamino" refers to the group —NHR, in which R is a substituted alkyl, as that term is defined above. For example, —NHCH$_2$CF$_3$ is a substituted alkylamino group.

The term "dialkylamino" when used without the "substituted" modifier refers to the group —NRR', in which R and R' can be the same or different alkyl groups, or R and R' can be taken together to represent an alkanediyl having two or more saturated carbon atoms, at least two of which are attached to the nitrogen atom. Non-limiting examples of dialkylamino groups include: —NHC(CH$_3$)$_3$, —N(CH$_3$)CH$_2$CH$_3$, —N(CH$_2$CH$_3$)$_2$, N-pyrrolidinyl, and N-piperidinyl. The term "substituted dialkylamino" refers to the group —NRR', in which R and R' can be the same or different substituted alkyl groups, one of R or R' is an alkyl and the other is a substituted alkyl, or R and R' can be taken together to represent a substituted alkanediyl with two or more saturated carbon atoms, at least two of which are attached to the nitrogen atom.

The terms "alkoxyamino", "alkenylamino", "alkynylamino", "arylamino", "aralkylamino", "heteroarylamino", "heteroaralkylamino", and "alkylsulfonylamino" when used without the "substituted" modifier, refers to groups, defined as —NHR, in which R is alkoxy, alkenyl, alkynyl, aryl, aralkyl, heteroaryl, heteroalkyl and alkylsulfonyl, respectively, as those terms are defined above. A non-limiting example of an arylamino group is —NHC$_6$H$_5$. When any of the terms alkoxyamino, alkenylamino, alkynylamino, arylamino, aralkylamino, heteroarylamino, heteroaralkylamino and alkylsulfonylamino is modified by "substituted," it refers to the group —NHR, in which R is substituted alkoxy, alkenyl, alkynyl, aryl, aralkyl, heteroaryl, heteroaralkyl and alkylsulfonyl, respectively.

The term "amido" (acylamino), when used without the "substituted" modifier, refers to the group —NHR, in which R is acyl, as that term is defined above. A non-limiting example of an acylamino group is —NHC(O)CH$_3$. When the term amido is used with the "substituted" modifier, it refers to groups, defined as —NHR, in which R is substituted acyl, as that term is defined above. The groups —NHC(O)OCH$_3$ and —NHC(O)NHCH$_3$ are non-limiting examples of substituted amido groups.

The term "alkylimino" when used without the "substituted" modifier refers to the group =NR, wherein the alkylimino group is attached with one σ-bond and one π-bond, in which R is an alkyl, as that term is defined above. Non-limiting examples of alkylimino groups include: =NCH$_3$, =NCH$_2$CH$_3$ and =N-cyclohexyl. The term "substituted alkylimino" refers to the group =NR, wherein the alkylimino group is attached with one σ-bond and one π-bond, in which R is a substituted alkyl, as that term is defined above. For example, =NCH$_2$CF$_3$ is a substituted alkylimino group.

Similarly, the terms "alkenylimino", "alkynylimino", "arylimino", "aralkylimino", "heteroarylimino", "heteroaralkylimino" and "acylimino", when used without the "substituted" modifier, refers to groups, defined as =NR, wherein the alkylimino group is attached with one σ-bond and one π-bond, in which R is alkenyl, alkynyl, aryl, aralkyl, heteroaryl, heteroaralkyl and acyl, respectively, as those terms are defined above. When any of the terms alkenylimino, alkynylimino, arylimino, aralkylimino and acylimino is modified by "substituted," it refers to the group =NR, wherein the alkylimino group is attached with one σ-bond and one π-bond, in which R is substituted alkenyl, alkynyl, aryl, aralkyl, heteroaryl, heteroaralkyl and acyl, respectively.

The term "fluoroalkyl" when used without the "substituted" modifier refers to an alkyl, as that term is defined above, in which one or more fluorines have been substituted for hydrogens. The groups, —CH$_2$F, —CF$_3$, and —CH$_2$CF$_3$ are non-limiting examples of fluoroalkyl groups. The term "substituted fluoroalkyl" refers to a non-aromatic monovalent group with a saturated carbon atom as the point of attachment, a linear or branched, cyclo, cyclic or acyclic structure, at least one fluorine atom, no carbon-carbon double or triple bonds, and at least one atom independently selected from the group consisting of N, O, Cl, Br, I, Si, P, and S. The following group is a non-limiting example of a substituted fluoroalkyl: —CFHOH.

The term "alkylphosphate" when used without the "substituted" modifier refers to the group —OP(O)(OH)(OR), in which R is an alkyl, as that term is defined above. Non-limiting examples of alkylphosphate groups include: —OP(O)(OH)(OMe) and —OP(O)(OH)(OEt). The term "substituted alkylphosphate" refers to the group —OP(O)(OH)(OR), in which R is a substituted alkyl, as that term is defined above.

The term "dialkylphosphate" when used without the "substituted" modifier refers to the group —OP(O)(OR)(OR'), in which R and R' can be the same or different alkyl groups, or R and R' can be taken together to represent an alkanediyl having two or more saturated carbon atoms, at least two of which are attached via the oxygen atoms to the phosphorus atom. Non-limiting examples of dialkylphosphate groups include: —OP(O)(OMe)$_2$, —OP(O)(OEt)(OMe) and —OP(O)(OEt)$_2$. The term "substituted dialkylphosphate" refers to the group —OP(O)(OR)(OR'), in which R and R' can be the same or different substituted alkyl groups, one of R or R' is an alkyl and the other is a substituted alkyl, or R and R' can be taken together to represent a substituted alkanediyl with two or more saturated carbon atoms, at least two of which are attached via the oxygen atoms to the phosphorous.

The term "alkylthio" when used without the "substituted" modifier refers to the group —SR, in which R is an alkyl, as that term is defined above. Non-limiting examples of alkylthio groups include: —SCH$_3$, —SCH$_2$CH$_3$, —SCH$_2$CH$_2$CH$_3$, —SCH(CH$_3$)$_2$, —SCH(CH$_2$)$_2$, —S-cyclopentyl, and —S-cyclohexyl. The term "substituted alkylthio" refers to the group —SR, in which R is a substituted alkyl, as that term is defined above. For example, —SCH$_2$CF$_3$ is a substituted alkylthio group.

Similarly, the terms "alkenylthio", "alkynylthio", "arylthio", "aralkylthio", "heteroarylthio", "heteroaralkylthio", and "acylthio", when used without the "substituted" modifier, refers to groups, defined as —SR, in which R is alkenyl, alkynyl, aryl, aralkyl, heteroaryl, heteroaralkyl and acyl, respectively, as those terms are defined above. When any of the terms alkenylthio, alkynylthio, arylthio, aralkylthio, heteroarylthio, heteroaralkylthio, and acylthio is modified by "substituted," it refers to the group —SR, in which R is substituted alkenyl, alkynyl, aryl, aralkyl, heteroaryl, heteroaralkyl and acyl, respectively.

The term "thioacyl" when used without the "substituted" modifier refers to a monovalent group with a carbon atom of a thiocarbonyl group as the point of attachment, further having a linear or branched, cyclo, cyclic or acyclic structure, further having no additional atoms that are not carbon or hydrogen, beyond the sulfur atom of the carbonyl group. The groups, —CHS, —C(S)CH$_3$, —C(S)CH$_2$CH$_3$, —C(S)CH$_2$CH$_2$CH$_3$, —C(S)CH(CH$_3$)$_2$, —C(S)CH(CH$_2$)$_2$, —C(S)C$_6$H$_5$, —C(S)C$_6$H$_4$CH$_3$, —C(S)C$_6$H$_4$CH$_2$CH$_3$, —C(S)C$_6$H$_3$(CH$_3$)$_2$, and —C(S)CH$_2$C$_6$H$_5$, are non-limiting examples of thioacyl groups. The term "thioacyl" therefore encompasses, but is not limited to, groups sometimes referred to as "alkyl thiocarbonyl" and "aryl thiocarbonyl" groups. The term "substituted thioacyl" refers to a radical with a carbon atom as the point of attachment, the carbon atom being part of a thiocarbonyl group, further having a linear or branched, cyclo, cyclic or acyclic structure, further having at least one atom, in addition to the sulfur atom of the carbonyl group, independently selected from the group consisting of N, O, F, Cl, Br, I, Si, P, and S. The groups, —C(S)CH$_2$CF$_3$, —C(S)O$_2$H, —C(S)OCH$_3$, —C(S)OCH$_2$CH$_3$, —C(S)OCH$_2$CH$_2$CH$_3$, —C(S)OC$_6$H$_5$, —C(S)OCH(CH$_3$)$_2$, —C(S)OCH(CH$_2$)$_2$, —C(S)NH$_2$, and —C(S)NHCH$_3$, are non-limiting examples of substituted thioacyl groups. The term "substituted thioacyl" encompasses, but is not limited to, "heteroaryl thiocarbonyl" groups.

The term "alkylsulfonyl" when used without the "substituted" modifier refers to the group —S(O)$_2$R, in which R is an alkyl, as that term is defined above. Non-limiting examples of alkylsulfonyl groups include: —S(O)$_2$CH$_3$, —S(O)$_2$CH$_2$CH$_3$, —S(O)$_2$CH$_2$CH$_2$CH$_3$, —S(O)$_2$CH(CH$_3$)$_2$, —S(O)$_2$CH(CH$_2$)$_2$, —S(O)$_2$-cyclopentyl, and —S(O)$_2$-cyclohexyl. The term "substituted alkylsulfonyl" refers to the group —S(O)$_2$R, in which R is a substituted alkyl, as that term is defined above. For example, —S(O)$_2$CH$_2$CF$_3$ is a substituted alkylsulfonyl group.

Similarly, the terms "alkenylsulfonyl", "alkynylsulfonyl", "arylsulfonyl", "aralkylsulfonyl", "heteroarylsulfonyl", and "heteroaralkylsulfonyl" when used without the "substituted"

modifier, refers to groups, defined as —S(O)₂R, in which R is alkenyl, alkynyl, aryl, aralkyl, heteroaryl, and heteroaralkyl, respectively, as those terms are defined above. When any of the terms alkenylsulfonyl, alkynylsulfonyl, arylsulfonyl, aralkylsulfonyl, heteroarylsulfonyl, and heteroaralkylsulfonyl is modified by "substituted," it refers to the group —S(O)₂R, in which R is substituted alkenyl, alkynyl, aryl, aralkyl, heteroaryl and heteroaralkyl, respectively.

The term "alkylsulfinyl" when used without the "substituted" modifier refers to the group —S(O)R, in which R is an alkyl, as that term is defined above. Non-limiting examples of alkylsulfinyl groups include: —S(O)CH₃, —S(O)CH₂CH₃, —S(O)CH₂CH₂CH₃, —S(O)CH(CH₃)₂, —S(O)CH(CH₂)₂, —S(O)-cyclopentyl, and —S(O)-cyclohexyl. The term "substituted alkylsulfinyl" refers to the group —S(O)R, in which R is a substituted alkyl, as that term is defined above. For example, —S(O)CH₂CF₃ is a substituted alkylsulfinyl group.

Similarly, the terms "alkenylsulfinyl", "alkynylsulfinyl", "arylsulfinyl", "aralkylsulfinyl", "heteroarylsulfinyl", and "heteroaralkylsulfinyl" when used without the "substituted" modifier, refers to groups, defined as —S(O)R, in which R is alkenyl, alkynyl, aryl, aralkyl, heteroaryl, and heteroaralkyl, respectively, as those terms are defined above. When any of the terms alkenylsulfinyl, alkynylsulfinyl, arylsulfinyl, aralkylsulfinyl, heteroarylsulfinyl, and heteroaralkylsulfinyl is modified by "substituted," it refers to the group —S(O)R, in which R is substituted alkenyl, alkynyl, aryl, aralkyl, heteroaryl and heteroaralkyl, respectively.

The term "alkylammonium" when used without the "substituted" modifier refers to a group, defined as —NH₂R⁺, —NHRR'⁺, or —NRR'R"⁺, in which R, R' and R" are the same or different alkyl groups, or any combination of two of R, R' and R" can be taken together to represent an alkanediyl. Non-limiting examples of alkylammonium cation groups include: —NH₂(CH₃)⁺, —NH₂(CH₂CH₃)+, —NH₂(CH₂CH₂CH₃)+, —NH(CH₃)₂, —NH(CH₂CH₃)₂⁺, —NH(CH₂CH₂CH₃)₂⁺, —N(CH₃)₃⁺, —N(CH₃)(CH₂CH₃)₂⁺, —N(CH₃)₂(CH₂CH₃)⁺, —NH₂C(CH₃)₃⁺, —NH(cyclopentyl)₂⁺ and —NH₂(cyclohexyl)⁺. The term "substituted alkylammonium" refers —NH₂R⁺, —NHRR'⁺, or —NRR'R"⁺, in which at least one of R, R' and R" is a substituted alkyl or two of R, R' and R" can be taken together to represent a substituted alkanediyl. When more than one of R, R' and R" is a substituted alkyl, they can be the same of different. Any of R, R' and R" that are not either substituted alkyl or substituted alkanediyl, can be either alkyl, either the same or different, or can be taken together to represent a alkanediyl with two or more carbon atoms, at least two of which are attached to the nitrogen atom shown in the formula.

The term "alkylsulfonium" when used without the "substituted" modifier refers to the group —SRR'⁺, in which R and R' can be the same or different alkyl groups, or R and R' can be taken together to represent an alkanediyl. Non-limiting examples of alkylsulfonium groups include: —SH(CH₃)⁺, —SH(CH₂CH₃)⁺, —SH(CH₂CH₂CH₃)⁺, —S(CH₃)₂⁺, —S(CH₂CH₃)₂⁺, —S(CH₂CH₂CH₃)₂⁺, —SH(cyclopentyl)⁺, and —SH(cyclohexyl)⁺. The term "substituted alkylsulfonium" refers to the group —SRR'⁺, in which R and R' can be the same or different substituted alkyl groups, one of R or R' is an alkyl and the other is a substituted alkyl, or R and R' can be taken together to represent a substituted alkanediyl. For example, —SH(CH₂CF₃)⁺ is a substituted alkylsulfonium group.

The term "alkylsilyl" when used without the "substituted" modifier refers to a monovalent group, defined as —SiH₂R, —SiHRR', or —SiRR'R", in which R, R' and R" can be the same or different alkyl groups, or any combination of two of R, R' and R" can be taken together to represent an alkanediyl. The groups, —SiH₂CH₃, —SiH(CH₃)₂, —Si(CH₃)₃ and —Si(CH₃)₂C(CH₃)₃, are non-limiting examples of unsubstituted alkylsilyl groups. The term "substituted alkylsilyl" refers —SiH₂R, —SiHRR', or —SiRR'R", in which at least one of R, R' and R" is a substituted alkyl or two of R, R' and R" can be taken together to represent a substituted alkanediyl. When more than one of R, R' and R" is a substituted alkyl, they can be the same of different. Any of R, R' and R" that are not either substituted alkyl or substituted alkanediyl, can be either alkyl, either the same or different, or can be taken together to represent a alkanediyl with two or more saturated carbon atoms, at least two of which are attached to the silicon atom.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include ¹³C and ¹⁴C. Similarly, it is contemplated that one or more carbon atom(s) of a compound of the present invention may be replaced by a silicon atom(s). Furthermore, it is contemplated that one or more oxygen atom(s) of a compound of the present invention may be replaced by a sulfur or selenium atom(s).

A compound having a formula that is represented with a dashed bond is intended to include the formulae optionally having zero, one or more double bonds. Thus, for example, the structure

includes the structures

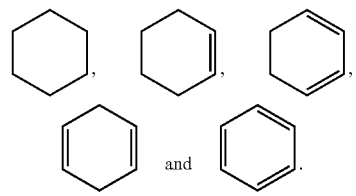

As will be understood by a person of skill in the art, no one such ring atom forms part of more than one double bond.

Any undefined valency on an atom of a structure shown in this application implicitly represents a hydrogen atom bonded to the atom.

A ring structure shown with an unconnected "R" group, indicates that any implicit hydrogen atom on that ring can be replaced with that R group. In the case of a divalent R group (e.g., oxo, imino, thio, alkylidene, etc.), any pair of implicit hydrogen atoms attached to one atom of that ring can be replaced by that R group. This concept is as exemplified below:

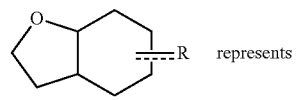

-continued

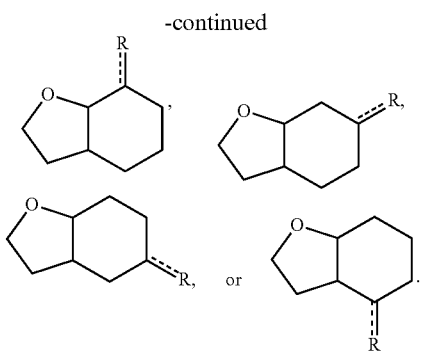

As used herein, a "chiral auxiliary" refers to a removable chiral group that is capable of influencing the stereoselectivity of a reaction. Persons of skill in the art are familiar with such compounds, and many are commercially available.

As used herein, a "label" is any composition or moiety detectable by spectroscopic, photochemical, biochemical, immunochemical, or chemical means. Labels that may be employed in the present invention include radioactive labels (e.g., $^{32}P$, $^{125}I$, $^{14}C$, $^{3}H$, and $^{35}S$) and fluorescent dyes (e.g., Cy3). An examples of a label that is not directly detected but is detected through the use of indirect methods is biotin.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "$IC_{50}$" refers to an inhibitory dose which is 50% of the maximum response obtained.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002), As used herein, "predominantly one enantiomer" means that a compound contains at least about 85% of one enantiomer, or more preferably at least about 90% of one enantiomer, or even more preferably at least about 95% of one enantiomer, or most preferably at least about 99% of one enantiomer. Similarly, the phrase "substantially free from other optical isomers" means that the composition contains at most about 15% of another enantiomer or diastereomer, more preferably at most about 10% of another enantiomer or diastereomer, even more preferably at most about 5% of another enantiomer or diastereomer, and most preferably at most about 1% of another enantiomer or diastereomer.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

The term "saturated" when referring to an atom means that the atom is connected to other atoms only by means of single bonds.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers.

The invention contemplates that for any stereocenter or axis of chirality for which stereochemistry has not been defined, that stereocenter or axis of chirality can be present in its R form, S form, or as a mixture of the R and S forms, including racemic and non-racemic mixtures.

"Substituent convertible to hydrogen in vivo" means any group that is convertible to a hydrogen atom by enzymological or chemical means including, but not limited to, hydrolysis and hydrogenolysis. Examples include hydrolyzable groups, such as acyl groups, groups having an oxycarbonyl group, amino acid residues, peptide residues, o-nitrophenylsulfenyl, trimethylsilyl, tetrahydro-pyranyl, diphenylphosphinyl, and the like. Examples of acyl groups include formyl, acetyl, trifluoroacetyl, and the like. Examples of groups having an oxycarbonyl group include ethoxycarbonyl, tert-butoxycarbonyl (—C(O)OC(CH$_3$)$_3$), benzyloxycarbonyl, p-methoxy-benzyloxycarbonyl, vinyloxycarbonyl, β-(p-toluenesulfonyl)ethoxycarbonyl, and the like. Suitable amino acid residues include, but are not limited to, residues of Gly (glycine), Ala (alanine), Arg (arginine), Asn (asparagine), Asp (aspartic acid), Cys (cysteine), Glu (glutamic acid), His (histidine), Ile (isoleucine), Leu (leucine), Lys (lysine), Met (methionine), Phe (phenylalanine), Pro (proline), Ser (serine), Thr (threonine), Trp (tryptophan), Tyr (tyrosine), Val (valine), Nva (norvaline), Hse (homoserine), 4-Hyp (4-hydroxyproline), 5-Hyl (5-hydroxylysine), Orn (ornithine) and β-Ala. Examples of suitable amino acid residues also include amino acid residues that are protected with a protecting group. Examples of suitable protecting groups include those typically employed in peptide synthesis, including acyl groups (such as formyl and acetyl), arylmethyloxycarbonyl groups (such as benzyloxycarbonyl and p-nitrobenzyloxycarbonyl), tert-butoxycarbonyl groups (—C(O)OC(CH$_3$)$_3$), and the like. Suitable peptide residues include peptide residues comprising two to five, and optionally amino acid residues. The residues of these amino acids or peptides can be present in stereochemical configurations of the D-form, the L-form or mixtures thereof. In addition, the amino acid or peptide residue may have an asymmetric carbon atom. Examples of suitable amino acid residues having an asymmetric carbon atom include residues of Ala, Leu, Phe, Trp, Nva, Val, Met, Ser, Lys, Thr and Tyr. Peptide residues having an asymmetric carbon atom include peptide residues having one or more constituent amino acid residues having an asymmetric carbon atom. Examples of suitable amino acid protecting groups include those typically employed in peptide synthesis, including acyl groups (such as formyl and acetyl), arylmethyloxycarbonyl groups (such as benzyloxycarbonyl and p-nitrobenzyloxycarbonyl), tert-butoxycarbonyl groups (—C(O)OC(CH$_3$)$_3$), and the like. Other examples of substituents "convertible to hydrogen in vivo" include reductively eliminable hydrogenolyzable groups. Examples of suitable reductively eliminable hydrogenolyzable groups include, but are not limited to, arylsulfonyl groups (such as o-toluenesulfonyl); methyl groups substituted with phenyl or benzyloxy (such as benzyl, trityl and benzyloxymethyl); arylmethoxycarbonyl groups (such as benzyloxycarbonyl and o-methoxybenzyloxycarbonyl); and haloethoxycarbonyl groups (such as β,β,β-trichloroethoxycarbonyl and β-iodoethoxycarbonyl).

"Therapeutically effective amount" or "pharmaceutically effective amount" means that amount which, when administered to a subject or patient for treating a disease, is sufficient to effect such treatment for the disease.

The term "therapeutic benefit" or "therapeutically effective" as used throughout this application refers to anything that promotes or enhances the well-being of the subject with respect to the medical treatment of a condition. This includes, but is not limited to, a reduction in the onset, frequency, duration, or severity of the signs or symptoms of a disease. For example, a therapeutically effective amount of a compound of the present invention (that is, a Wnt protein signalling inhibitor) may be an amount sufficient to treat or prevent osteopetrosis.

The terms "inhibiting," or "reducing" or any variation of these terms, when used in the claims and/or the specification, includes any measurable decrease or complete inhibition to achieve a desired result. For example, there may be a decrease of 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, reduction of activity compared to normal. In a further example, following administering of a Wnt protein signalling inhibitor, a cancer patient may experience a reduction in tumor size.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

The terms "contacted" and "exposed," when applied to a cell, are used herein to describe the process by which a compound of the present invention is administered or delivered to a target cell, or are placed in direct juxtaposition with the target cell. The terms "administered" and "delivered" are used interchangeably with "contacted" and "exposed."

As used herein, the term "water soluble" means that the compound dissolves in water at least to the extent of 0.010 mole/liter or is classified as soluble according to literature precedence.

Other abbreviations used herein are as follows: DMSO, dimethyl sulfoxide; NO, nitric oxide; iNOS, inducible nitric oxide synthase; COX-2, cyclooxygenase-2; NGF, nerve growth factor; IBMX, isobutylmethylxanthine; FBS, fetal bovine serum; GPDH, glycerol 3-phosphate dehydrogenase; RXR, retinoid X receptor; TGF-β, transforming growth factor-β; IFNγ or IFN-γ, interferon-γ; LPS, bacterial endotoxic lipopolysaccharide; TNFα or TNF-α, tumor necrosis factor-α; IL-1β, interleukin-1β; GAPDH, glyceraldehyde-3-phosphate dehydrogenase; MTT, 3-[4,5-dimethylthiazol-2-yl]-2, 5-diphenyltetrazolium bromide; TCA, trichloroacetic acid; HO-1, inducible heme oxygenase.

Modifications or derivatives of the compounds, agents, and active ingredients disclosed throughout this specification are contemplated as being useful with the methods and compositions of the present invention. Derivatives may be prepared and the properties of such derivatives may be assayed for their desired properties by any method known to those of skill in the art, such as methods described herein.

In certain aspects, "derivative" refers to a chemically-modified compound that still retains the desired effects of the compound prior to the chemical modification. A "Wnt protein signalling inhibitor derivative," therefore, refers to a chemically modified Wnt protein signalling inhibitor that still retains the desired effects of the parent Wnt protein signalling inhibitor prior to its chemical modification. Such effects may be enhanced (e.g., slightly more effective, twice as effective, etc.) or diminished (e.g., slightly less effective, 2-fold less effective, etc.) relative to the parent Wnt protein signalling inhibitor, but may still be considered a Wnt protein signalling inhibitor derivative. Such derivatives may have the addition, removal, or substitution of one or more chemical moieties on the parent molecule. Non-limiting examples of the types of modifications that can be made to the compounds and structures disclosed herein include the addition or removal of lower unsubstituted alkyls such as methyl, ethyl, propyl, or substituted lower alkyls such as hydroxymethyl or aminomethyl groups; carboxyl groups and carbonyl groups; hydroxyls; nitro, amino, amide, imide, and azo groups; sulfate, sulfonate, sulfono, sulfhydryl, sulfenyl, sulfonyl, sulfoxido, sulfonamide, phosphate, phosphono, phosphoryl groups, and halide substituents. Additional modifications can include an addition or a deletion of one or more atoms of the atomic framework, for example, substitution of an ethyl by a propyl, or substitution of a phenyl by a larger or smaller aromatic group. Alternatively, in a cyclic or bicyclic structure, heteroatoms such as N, S, or O can be substituted into the structure instead of a carbon atom.

Prodrugs and solvates of the compounds of the present invention are also contemplated herein. The term "prodrug," as used herein, is understood as being a compound which, upon administration to a subject, such as a mammal, undergoes chemical conversion by metabolic or chemical processes to yield a compound any of the formulas herein, or a salt and/or solvate thereof. Solvates of the compounds of the present invention are preferably hydrates.

As used herein, "protecting group" refers to a moiety attached to a functional group to prevent an otherwise unwanted reaction of that functional group. The term "functional group" generally refers to how persons of skill in the art classify chemically reactive groups. Examples of functional groups include hydroxyl, amine, sulfhydryl, amide, carboxyl, carbonyl, etc. Protecting groups are well-known to those of skill in the art. Non-limiting exemplary protecting groups fall into categories such as hydroxy protecting groups, amino protecting groups, sulfhydryl protecting groups and carbonyl protecting groups. Such protecting groups may be found in Greene and Wuts, 1999, incorporated herein by reference in its entirety. The Wnt protein signalling inhibitors described herein are also contemplated as protected by one or more protecting groups—that is, the inhibitors are contemplated in their "protected form."

Compounds of the present invention may contain one or more asymmetric centers and thus can occur as racemates and racemic mixtures, single enantiomers, diastereomeric mixtures and individual diastereomers. In certain embodiments, a single diastereomer is present. All possible stereoisomers of the compounds of the present invention are contemplated as being within the scope of the present invention. However, in certain aspects, particular diastereomers are contemplated. The chiral centers of the compounds of the present invention can have the S- or the R-configuration, as defined by the IUPAC 1974 Recommendations. In certain aspects, certain compounds of the present invention may comprise S- or R-configurations at particular carbon centers.

Synthetic techniques that may be used to prepare certain compounds of the present invention are provided in the Examples section. Other synthetic techniques to prepare compounds of the present invention as well as derivatives are well-known to those of skill in the art. For example, Smith and March, 2001 discuss a wide variety of synthetic transformations, reaction conditions, and possible pitfalls relating thereto. Methods discussed therein may be adapted to prepare compounds of the present invention from commerically available starting materials.

Solvent choices for preparing compounds of the present invention will be known to one of ordinary skill in the art. Solvent choices may depend, for example, on which one(s) will facilitate the solubilizing of all the reagents or, for example, which one(s) will best facilitate the desired reaction (particularly when the mechanism of the reaction is known). Solvents may include, for example, polar solvents and non-polar solvents. Solvents choices include, but are not limited to, tetrahydrofuran, dimethylformamide, dimethylsulfoxide, dioxane, methanol, ethanol, hexane, methylene chloride and acetonitrile. More than one solvent may be chosen for any particular reaction or purification procedure. Water may also be admixed into any solvent choice. Further, water, such as distilled water, may constitute the reaction medium instead of a solvent.

Persons of ordinary skill in the art will be familiar with methods of purifying compounds of the present invention. One of ordinary skill in the art will understand that compounds of the present invention can generally be purified at any step, including the purification of intermediates as well as purification of the final products. In preferred embodiments, purification is performed via silica gel column chromatography or HPLC.

In view of the above definitions, other chemical terms used throughout this application can be easily understood by those of skill in the art. Terms may be used alone or in any combination thereof.

The above definitions supersede any conflicting definition in any of the reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

V. PHARMACEUTICAL FORMULATIONS AND ROUTES FOR ADMINISTRATION

Pharmaceutical compositions of the present invention comprise an effective amount of one or more candidate substances (e.g., a Wnt protein signalling inhibitor) or additional agents dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one candidate substance or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, pp 1289-1329, 1990). Except insofar as any conventional carrier is incompatible with the active ingredient, its use in the therapeutic or pharmaceutical compositions is contemplated.

The candidate substance may comprise different types of carriers depending on whether it is to be administered in solid, liquid or aerosol form, and whether it needs to be sterile for such routes of administration as injection. Compounds of the present invention may be administered orally, intraadiposally, intraarterially, intraarticularly, intracranially, intradermally, intralesionally, intramuscularly, intranasally, intraocularly, intrapericardially, intraperitoneally, intrapleurally, intraprostaticaly, intrarectally, intrathecally, intratracheally, intratumorally, intraumbilically, intravaginally, intravenously, intravesicularlly, intravitreally, liposomally, locally, mucosally, orally, parenterally, rectally, subconjunctival, subcutaneously, sublingually, topically, transbuccally, transdermally, vaginally, in crèmes, in lipid compositions, via a catheter, via a lavage, via continuous infusion, via infusion, via inhalation, via injection, via local delivery, via localized perfusion, bathing target cells directly, or by other method or any combination of the foregoing as would be known to one of ordinary skill in the art (see, for example, Remington's Pharmaceutical Sciences, 1990). In particular embodiments, the composition may be formulated for oral delivery. Pharmaceutical compositions comprising a compound of the present invention are also contemplated, and such compositions may be adapted for administration via any method known to those of skill in the art, such as the methods described above.

In particular embodiments, the composition is administered to a subject using a drug delivery device. Any drug delivery device is contemplated for use in delivering a pharmaceutically effective amount of a Wnt protein signalling inhibitor.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. The practitioner responsible for administration will typically determine the concentration of active ingredient(s) in a composition and appropriate dose(s) for the individual subject.

The dose can be repeated as needed as determined by those of ordinary skill in the art. Thus, in some embodiments of the methods set forth herein, a single dose is contemplated. In other embodiments, two or more doses are contemplated. Where more than one dose is administered to a subject, the time interval between doses can be any time interval as determined by those of ordinary skill in the art. For example, the time interval between doses may be about 1 hour to about 2 hours, about 2 hours to about 6 hours, about 6 hours to about 10 hours, about 10 hours to about 24 hours, about 1 day to about 2 days, about 1 week to about 2 weeks, or longer, or any time interval derivable within any of these recited ranges.

In certain embodiments, it may be desirable to provide a continuous supply of a pharmaceutical composition to the patient. This could be accomplished by catheterization, followed by continuous administration of the therapeutic agent, for example. The administration could be intra-operative or post-operative.

In certain embodiments, pharmaceutical compositions may comprise, for example, at least about 0.1% of a Wnt protein signalling inhibitor. In other embodiments, the Wnt protein signalling inhibitor may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal, or combinations thereof.

The Wnt protein signalling inhibitor may be formulated into a composition, such as a pharmaceutical composition, in a free base, neutral, or salt form. Pharmaceutically acceptable salts are described herein.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. It may be preferable to include isotonic agents, such as, for example, sugars, sodium chloride, or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in certain embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the candidate substance is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. In certain embodiments, carriers for oral administration comprise inert diluents (e.g., glucose, lactose, or mannitol), assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain embodiments an oral composition may comprise one or more binders, excipients, disintegration agents, lubricants, flavoring agents, or combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar, or both.

Sterile injectable solutions may be prepared by incorporating a compound of the present invention in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, certain methods of preparation may include vacuum-drying or freeze-drying techniques which yield a powder of the active ingredient plus any additional desired ingredient from a previously sterile-filtered liquid medium thereof. The liquid medium should be suitably buffered if necessary and the liquid diluent (e.g., water) first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition should be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin, or combinations thereof.

VI. COMBINATION THERAPY

In order to enhance or increase the effectiveness of a Wnt protein signalling inhibitor of the present invention, the inhibitor may be combined with another therapy, such as another agent that combats and/or prevents cancer, osteopetrosis, a degenerative disease, or type II diabetes. For example, Wnt protein signalling inhibitors of the present invention may be provided in a combined amount with an effective amount another agent that is known to reduce tumor size.

It is contemplated that combination therapy of the present invention may be used in vitro or in vivo. These processes may involve administering the agents at the same time or within a period of time wherein separate administration of the substances produces a desired therapeutic benefit. This may be achieved by contacting the cell, tissue, or organism with a single composition or pharmacological formulation that includes two or more agents, or by contacting the cell with two or more distinct compositions or formulations, wherein one composition includes one agent and the other includes another.

The compounds of the present invention may precede, be co-current with and/or follow the other agents by intervals ranging from minutes to weeks. In embodiments where the agents are applied separately to a cell, tissue or organism, one would generally ensure that a significant period of time did not expire between the time of each delivery, such that the agents would still be able to exert an advantageously combined effect on the cell, tissue or organism. For example, in such instances, it is contemplated that one may contact the cell, tissue or organism with two, three, four or more modalities substantially simultaneously (i.e., within less than about a minute) as the candidate substance. In other aspects, one or more agents may be administered about 1 minute, about 5 minutes, about 10 minutes, about 20 minutes about 30 minutes, about 45 minutes, about 60 minutes, about 2 hours, about 3 hours, about 4 hours, about 5 hours, about 6 hours, about 7 hours about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, about 48 hours, about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 1, about 2, about 3, about 4, about 5, about 6, about 7 or about 8 weeks or more, and any range derivable therein, prior to and/or after administering the candidate substance.

Various combination regimens of the agents may be employed. Non-limiting examples of such combinations are shown below, wherein an Wnt protein signalling inhibitor is "A" and a second agent, such as an anti-cancer agent, is "B":

| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

A. Anti-Cancer Therapy

An anti-cancer agent may be used in combination therapy with Wnt protein signalling inhibitors of the present invention. As used herein, an "anti-cancer" agent is capable of negatively affecting cancer in a subject, for example, by killing one or more cancer cells, inducing apoptosis in one or more cancer cells, reducing the growth rate of one or more cancer cells, reducing the incidence or number of metastases, reducing tumor size, inhibiting tumor growth, reducing the blood supply to a tumor or one or more cancer cells, promoting an immune response against one or more cancer cells or a tumor, preventing or inhibiting the progression of a cancer, or increasing the lifespan of a subject with a cancer. Anti-cancer agents are well-known in the art and include, for example, chemotherapy agents (chemotherapy), radiotherapy agents (radiotherapy), a surgical procedure, immune therapy agents (immunotherapy), genetic therapy agents (gene therapy), reoviral therapy, hormonal therapy, other biological agents (biotherapy), and/or alternative therapies.

B. Osteopetrosis Therapy

Osteopetrosis, also known as marble bone disease and Albers-Schonberg disease, is an extremely rare inherited disorder whereby the bones harden, becoming denser, in contrast to the more prevalent osteomalacia, in which the bones soften. Bone marrow transplant therapy may be combined with administration of Wnt protein signalling inhibitors of the present invention to treat or prevent osteopetrosis. Other treatments targeting osteopetrosis that may be combined with Wnt protein signalling inhibitors described herein include those disclosed in the following documents, each of which is incorporated herein by reference: U.S. Pat. Nos. 7,241,732; 7,186,683; 6,943,151; 6,833,354; 6,699,873; 6,686,148; 5,806,529; 5,777,193; RE35,694; 5,641,747; and 4,843,063.

C. Degenerative Disease Therapy

As discussed herein, degenerative diseases may be treated using Wnt protein signalling inhibitors of the present invention. Accordingly, other treatments that target degenerative diseases may be combined with administration of the Wnt protein signalling inhibitors. Non-limiting examples of degenerative diseases include type II diabetes and age-related impairment of tissue repair.

1. Type II Diabetes Therapy

Type II diabetes is a chronic, progressive disease that has no clearly established cure. It is a metabolic disorder that is primarily characterized by insulin resistance, relative insulin deficiency and hyperglycemia. Treatment options that may be combined with Wnt protein signalling inhibitor administration include exercise, diet management to control the intake of glucose, and use of anti-diabetic drugs (e.g., metformin, phenformin, repaglinide, nateglinide, rosiglitazone, pioglitazone or miglitol).

2. Age-Related Impairment of Tissue Repair Therapy

A variety of tissues degenerate over time as one ages, such as skeletal muscle and organ tissues (e.g., heart, kidney, lung and liver). Wnt protein signalling inhibition has been implicated in, for example, muscle regeneration (Brack et al., 2007). Therapies pertaining to age-related impairment of tissue repair that may be combined with Wnt protein signalling inhibitor administration include, for example, gene therapy, such as described by Barton-Davis et al. (1998; incorporated herein by reference) and drugs described by Lynch (2004; incorporated herein by reference).

VII. EXAMPLES

The following examples are included to demonstrate certain preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Cell Lines, Constructs, Antibodies, and siRNAs.

L-Wnt-STF cells were generated by transfecting L-Wnt cells (ATCC) with SuperTopFlash (STF; provided by R. Moon) and SV-40*Renilla* luciferase plasmids and selecting for clones resistant to G418 and Zeocin. Constructs for expression of Shh and Wnt3A were provided by P. Beachy, and Notch intracellular domain (NICD) by R. Kopan. Notch reporter construct was provided by J. LaBorda, Wnt 1 and Wnt 2 expression constructs were purchased from OpenBiosystems and are part of the MGC Clone collection. The Wnt-GL expression construct was generated by ligating Wnt3A coding sequence to GL (lacking the signal sequence; AA15-185) using an engineered XbaI site. CMV-GL was generated by inserting the CMV promoter into the pGluc-Basic vector (New England Biolabs). Expression constructs for mPorc-myc, hAxin2-myc and hAxinADIX were engineered using PCR-based cloning and mutagenesis strategies. The following primary antibodies were used for detection: β-catenin, Kif3A, Actin, and β-tubulin (all purchased from Sigma); phosphorylated LRP6, Dvl2, and Axin2 (from Cell Signalling Technology); E-Cadherin (BD Transduction Laboratories); APC (Santa Cruz Biotechnology); and GSK3 (Stressgen). Pools of pre-designed siRNA reagents (four siRNAs per gene) used in RNAi experiments were purchased from either Qiagen (GSK3β, CK1α, PP1, PP2CA, PP2CB, KAP, WTX, ASEF, DLG1) or from Dharmacon (APC, Axin2).

Biochemical Studies.

Biochemical studies involving L-Wnt-STF or DLD-1 cells were performed in either 48- or 6-well format with IWR (10 µM) or IWP (5 µM) compounds and/or cycloheximide (100 µM) in a 48 hr assay period. Targeting of APC using RNAi in L-cells was achieved by transfecting cells with SMARTPool APC siRNAs (50 nM; Dharmacon). E-cadherin depletion studies were performed at 4° C. using DLD-1 cells lysed in PBS/1% NP-40/protease inhibitors. For Wnt3A phase separation assays, murine Porcupine (C isoform) and human Wnt3A-myc were transfected into HEK 293 cells (6 well format, 400K cells/well) as appropriate using Effectene transfection reagent (QIAGEN). After 48 hrs of incubation, cells were lysed for 15 min, RT with PL buffer (distilled water, 10 mM tris-HCl, 150 mM NaCl)/1% TritionX-114. Lysate was briefly chilled on ice, pelleted for 10 min 4° C., and the supernatant combined with an equal volume of PL buffer/ 3.5% TX-114. Solutions were rotated for 15 min at 4° C., placed at 37° C. for 5 min followed by an additional centrifugation for 5 min at 2000 g, RT. Distinct phases were collected and combined with PL buffer to a total volume of 1 mL. Samples were chilled on ice, ConA sepharose (GE Healthcare) added, and samples rotated for 2 hrs at 4° C. Beads washed 2× with PL buffer, and a Western blot performed with eluted proteins using an anti-c-myc antibody. For IWP-PEG-Biotin binding studies, cell lysate (PBS/1% NP-40) derived from HEK293 cells transfected with the Porc-myc construct was incubated with either DMSO, linker (165 μM), IWP-biotin (165 μM), or IWP-biotin (165 μM)+IWP3 (585 μM) and rotated for 30 min prior to addition of NeutrAvidin agarose resin (Pierce) and an additional 20 in rotation at RT. Resin was then washed lysis buffer and protein eluted with sample loading buffer.

Example 2

Identification of Wnt Protein Signalling Inhibitors

A high stringency cell-based screening strategy identified small molecular modulators of the Wnt/β-catenin pathway from a ~200K synthetic chemical library from U.T. Southwestern (Dallas, Tex.) (UTSW) (FIG. 1). This assay may be employed to identify Wnt-protein signalling inhibitors as well as chemicals that can increase Wnt/β-catenin activity.

Experimental Conditions: Primary Screen and Secondary Reporter-Based Assays.

For the "primary screen" and "dose-dependent test," 5,000 L-Wnt-STF cells were seeded into each well of a white opaque 384 well plate and individual compounds from the UTSW chemical library added 24 hrs later to each well at a final concentration of 2.5 μM (primary screen) or otherwise indicated concentrations. Luciferase activities were measured 24 hrs later. To identify FL inhibitors and compounds that blocked protein secretion, L-cells were transiently transfected with CMV-FL and CMV-GL constructs and immediately incubated with compounds. Culture medium and cell lysates were analyzed for GL and FL activities, respectively, after 24 hrs. For the "exogenous Wnt test," Wnt3A-containing conditioned medium, prepared following the protocol provided ATCC, was applied to HEK293 cells transiently transfected with STF and control reporters. For Hedgehog and Notch tests, NIH-3T3 cells or L-cells, respectively, were transiently transfected with indicated reporter constructs and immediately incubated with compounds. Luciferase activities were measured 24 hrs later. The "Wnt secretion test" was performed in L-cells transiently transfected with the Wnt-GL expression construct and immediately incubated with compounds. Culture medium and cellular lysate were analyzed 48 hrs later for GL activity. Assays used to calculate IC50's for compounds were performed as before in L-Wnt-STF cells.

Figure 8:
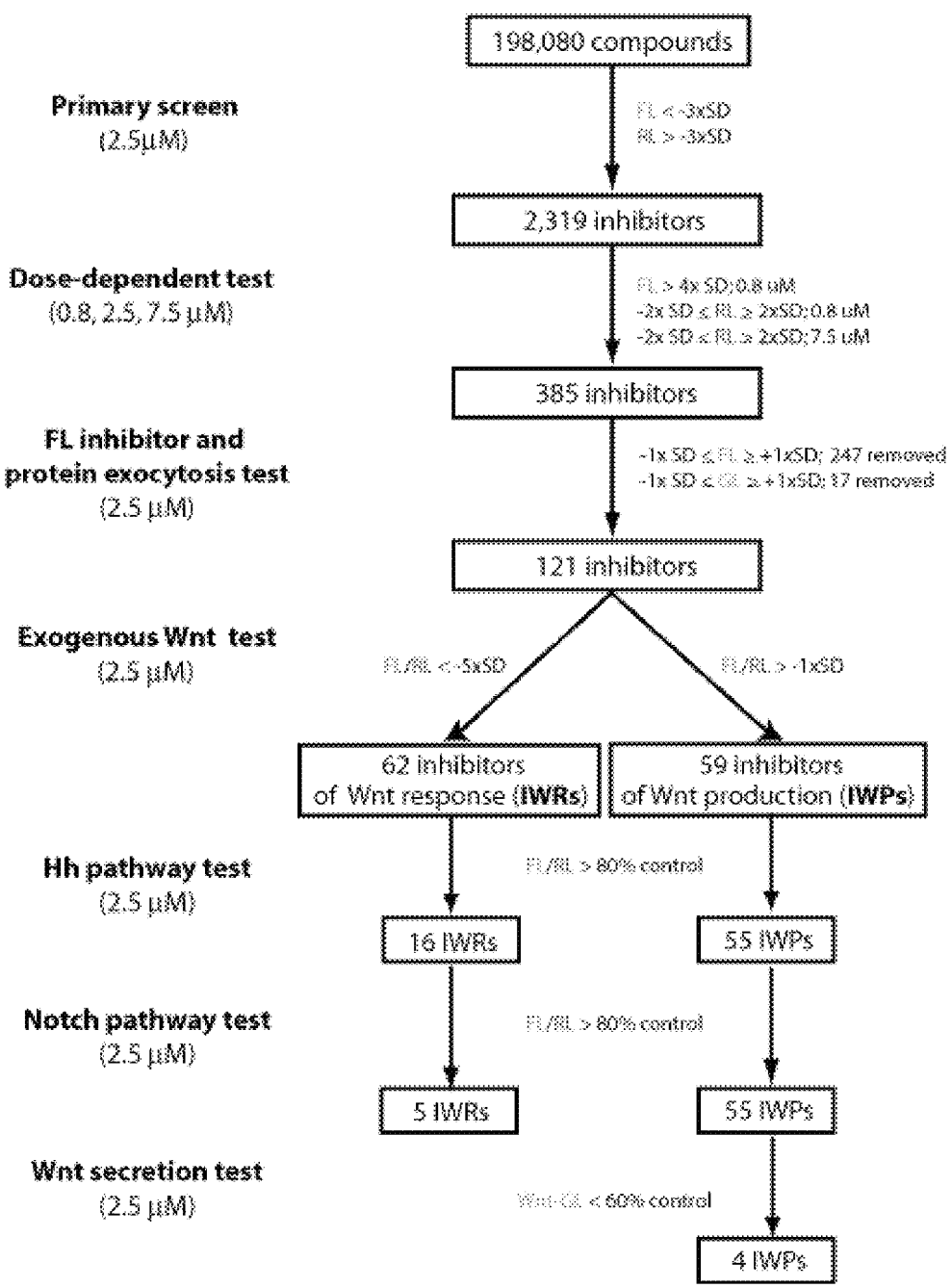
FIG. 8. Criteria used to identify hits in the screen. Flow diagram of screening process to identify chemical inhibitors of Wnt/β-catenin pathway activity as shown in FIG. 1 except with criteria used to identify compounds of interest noted in each step.
Figure 10:
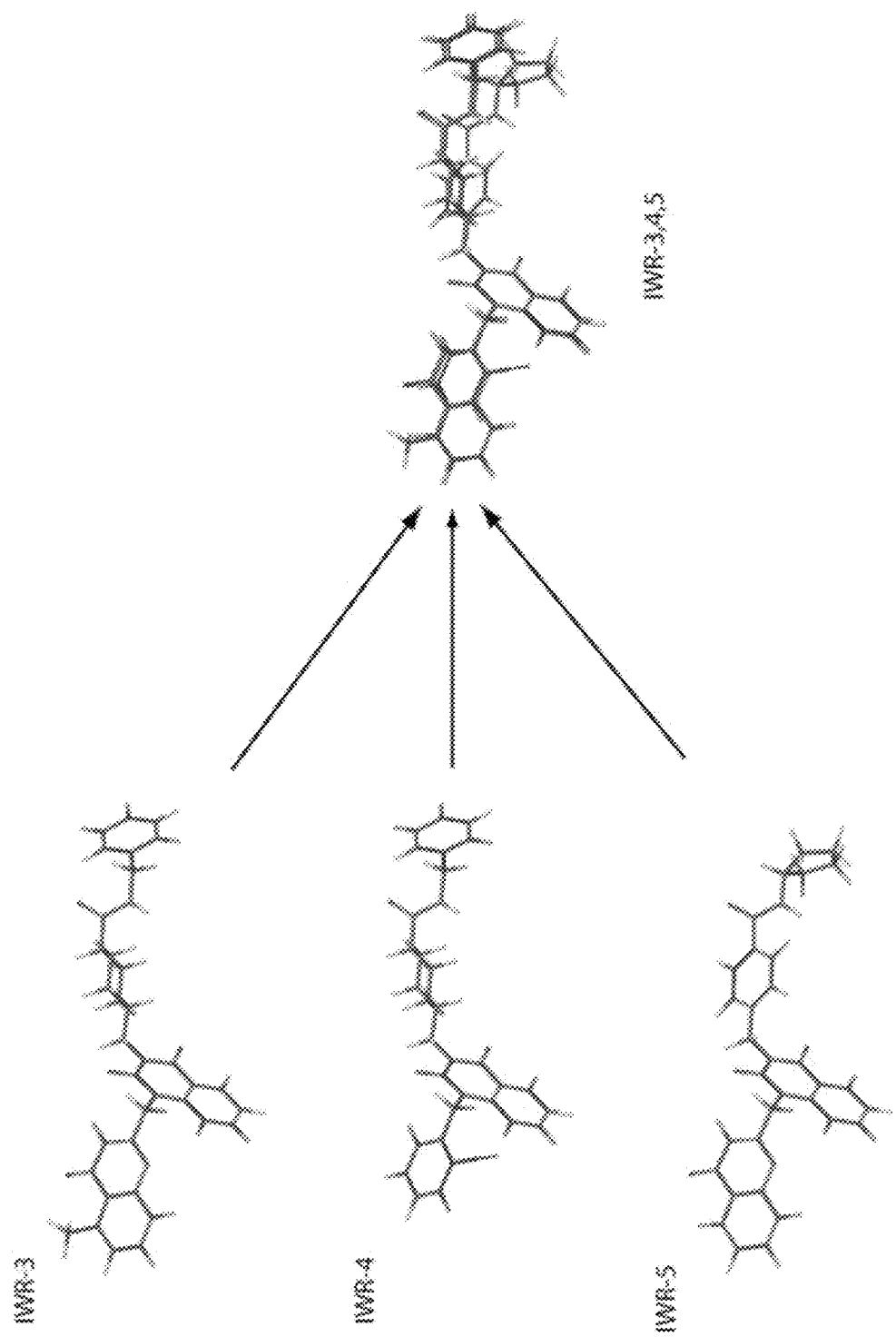
FIG. 10. IWR 3-5 share structural similarity. Three dimensional representation of IWRs 3-5 in equilibrium geometry using AM1 semi-empirical methods reveals similarities in structure. All three structures are superimposed on the right.
Figure 14:
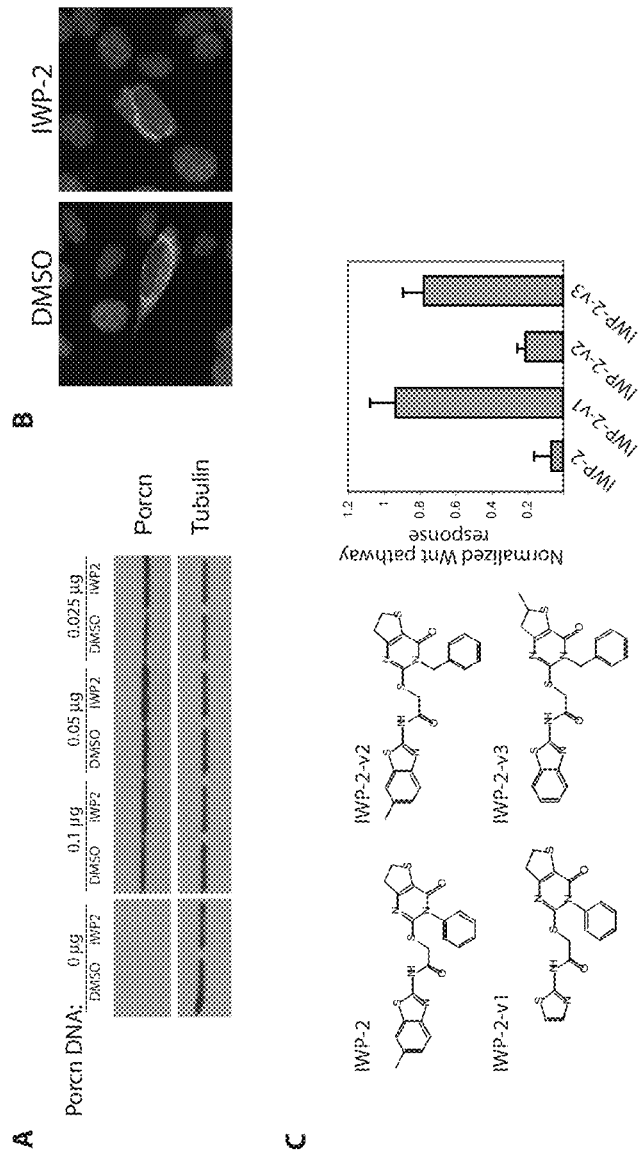
FIGS. 14A-C. Characterization of IWP action and specificity.
Figure 15:
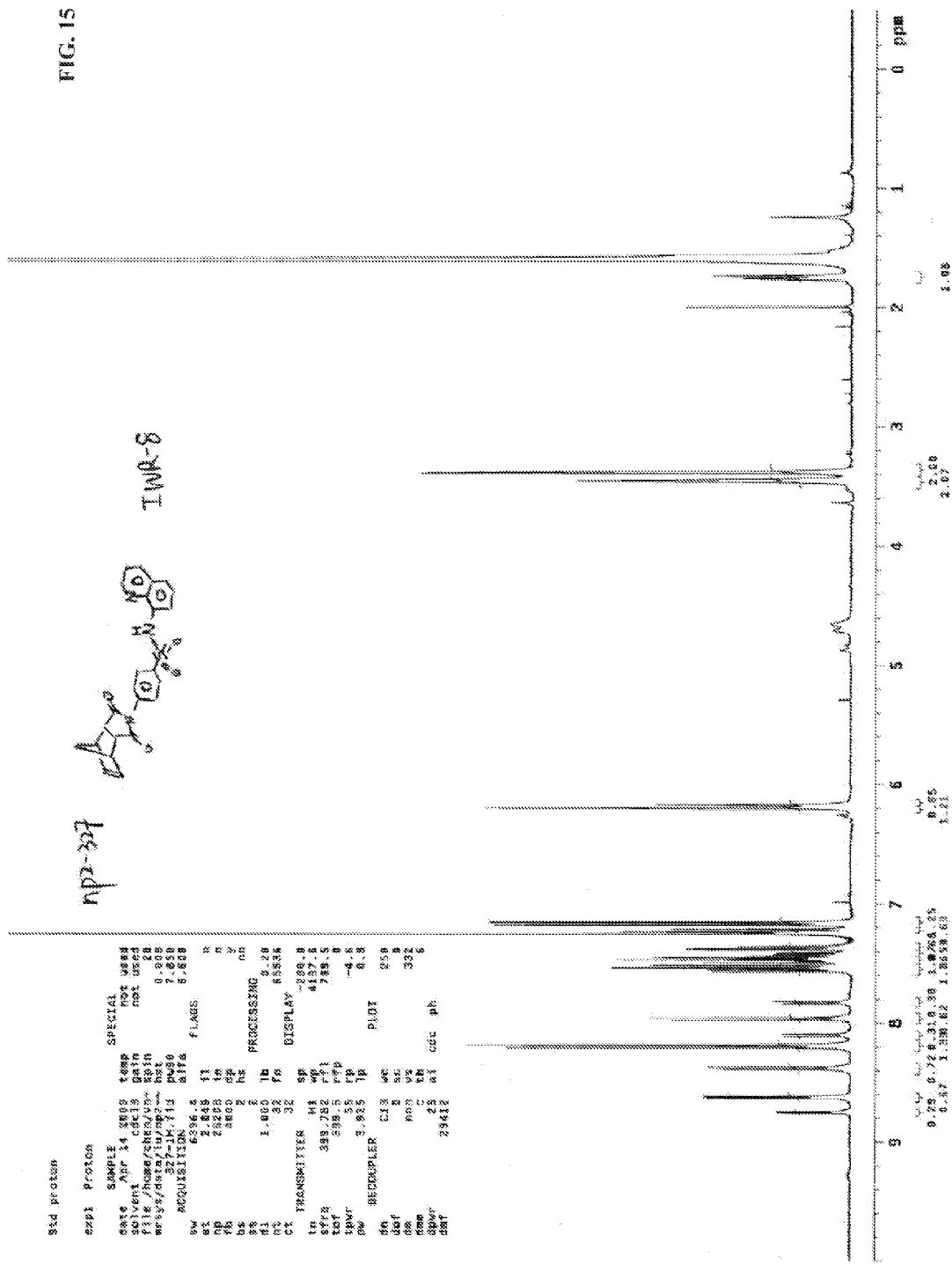
FIGS. 15-24. $^1$H-NMR Spectra for Inhibitors of Wnt Response.
Figure 16:
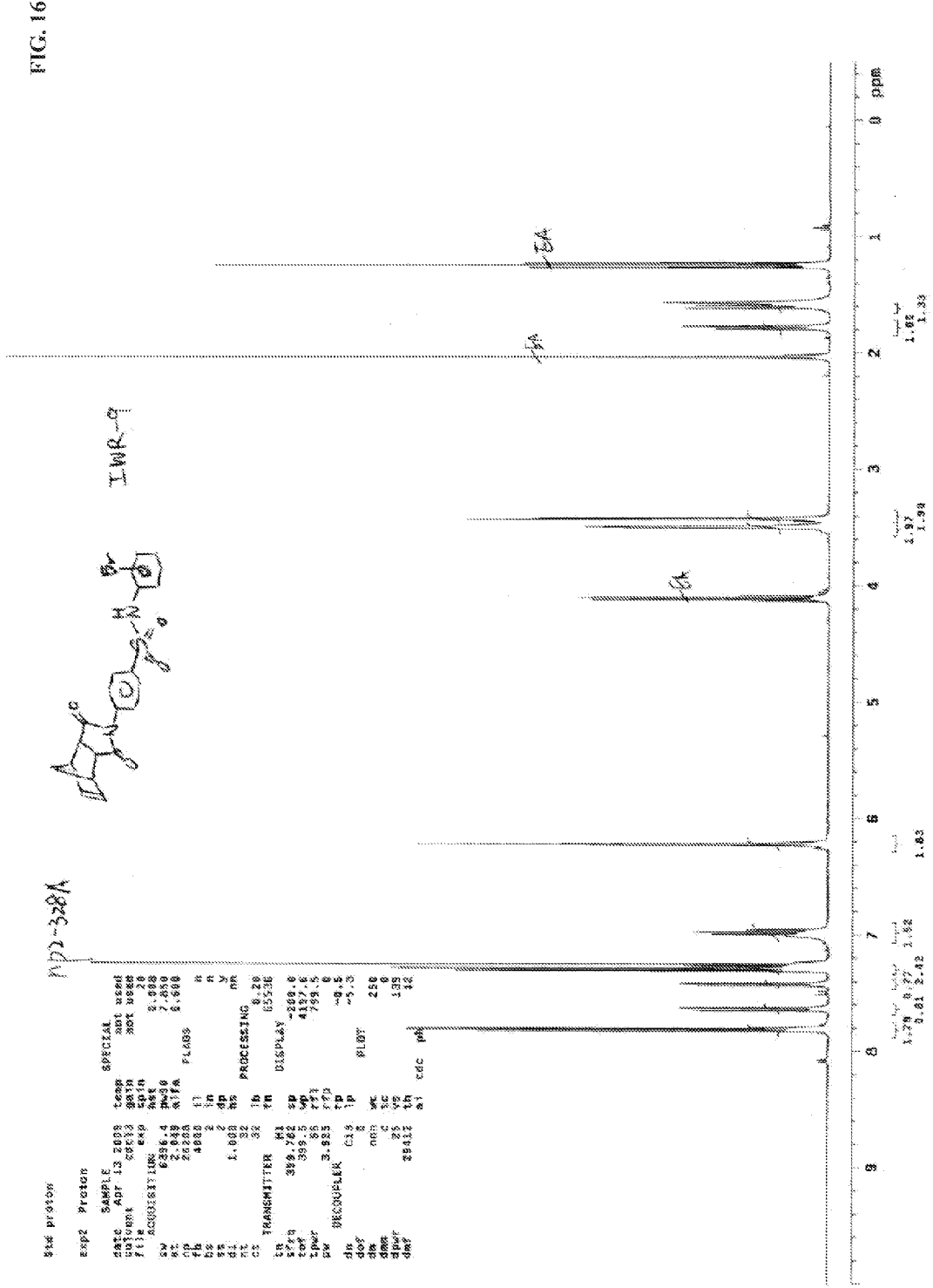
Figure 17:
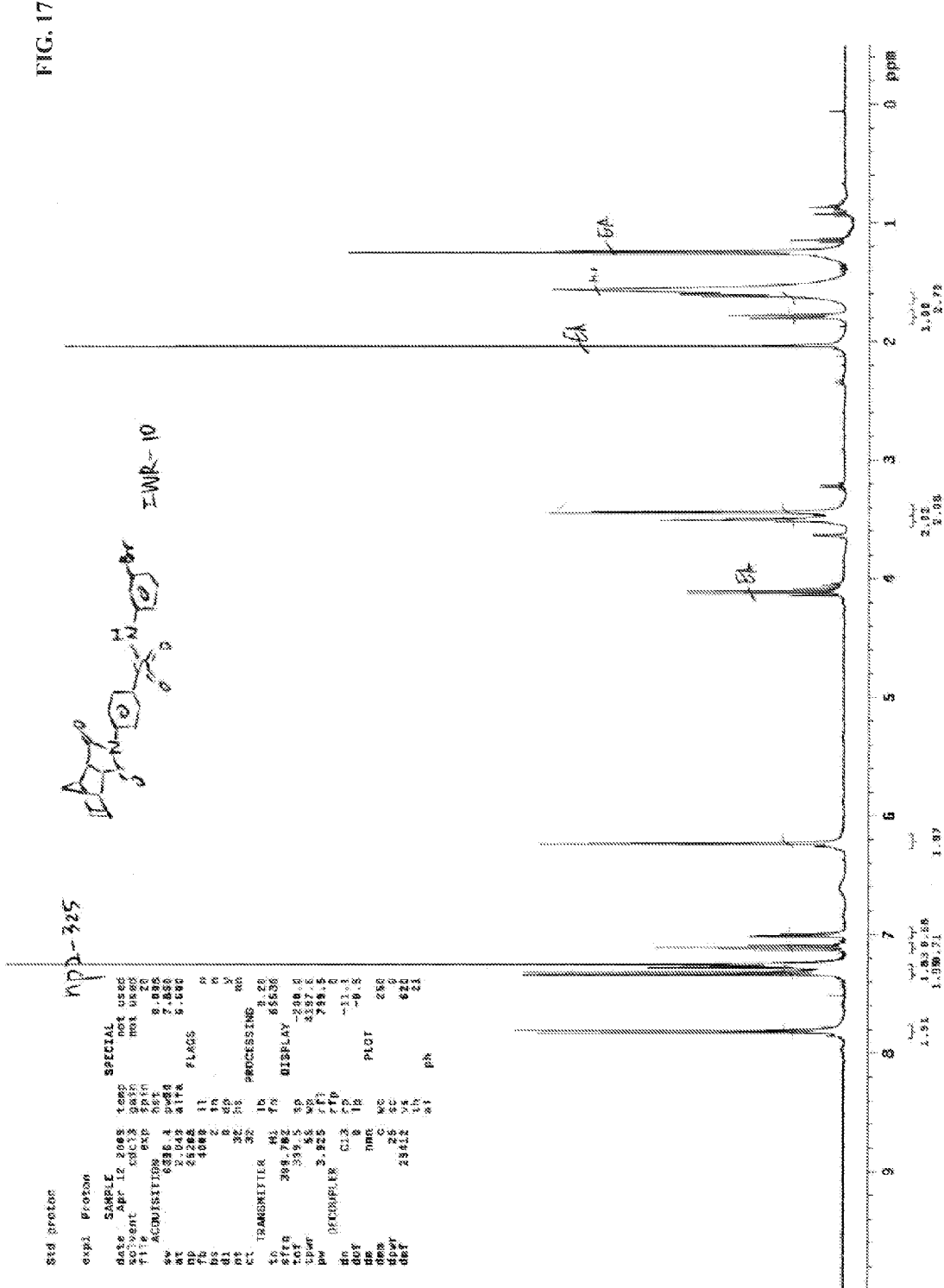
Figure 18:
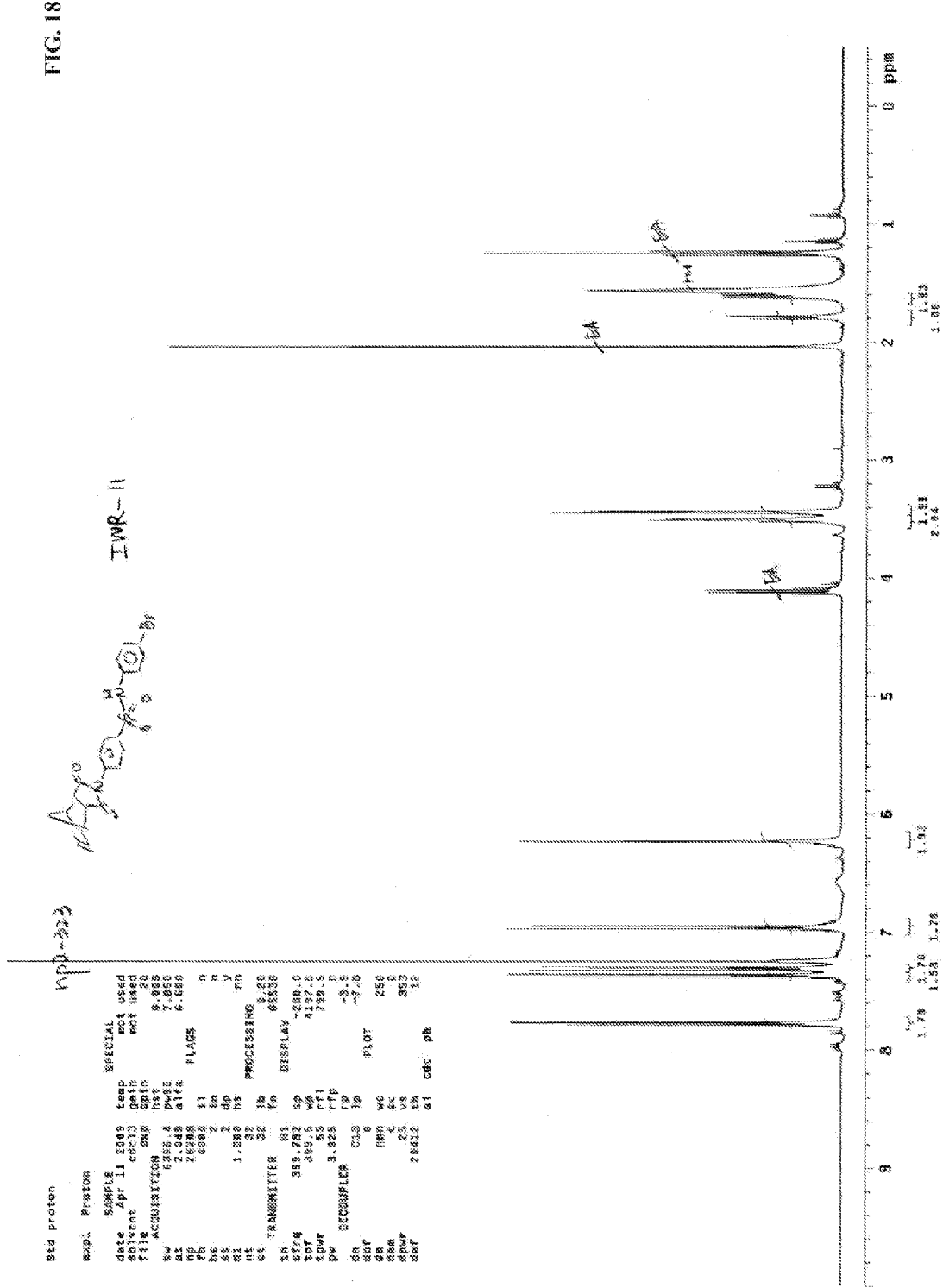
Figure 19:
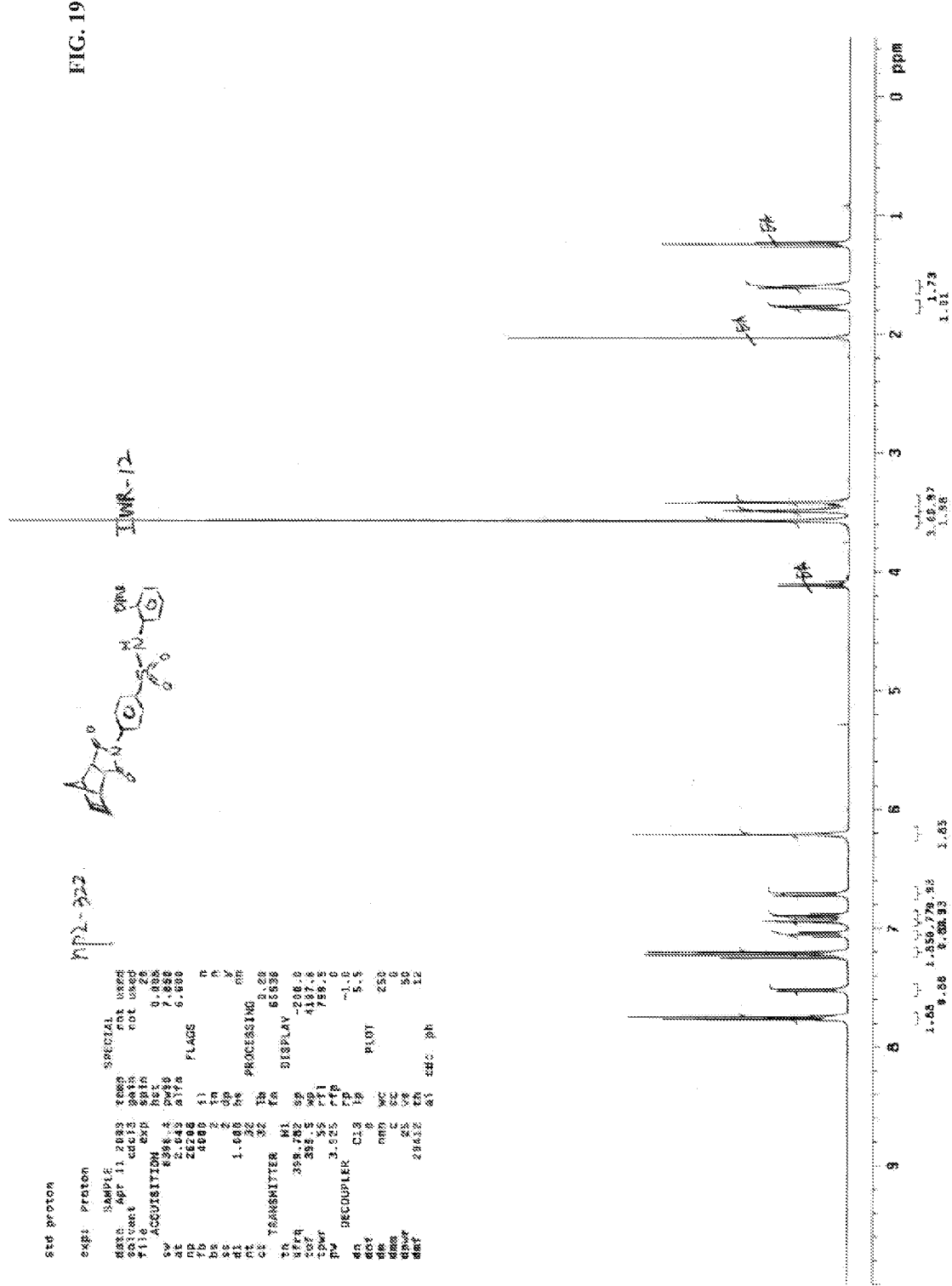
Figure 20:
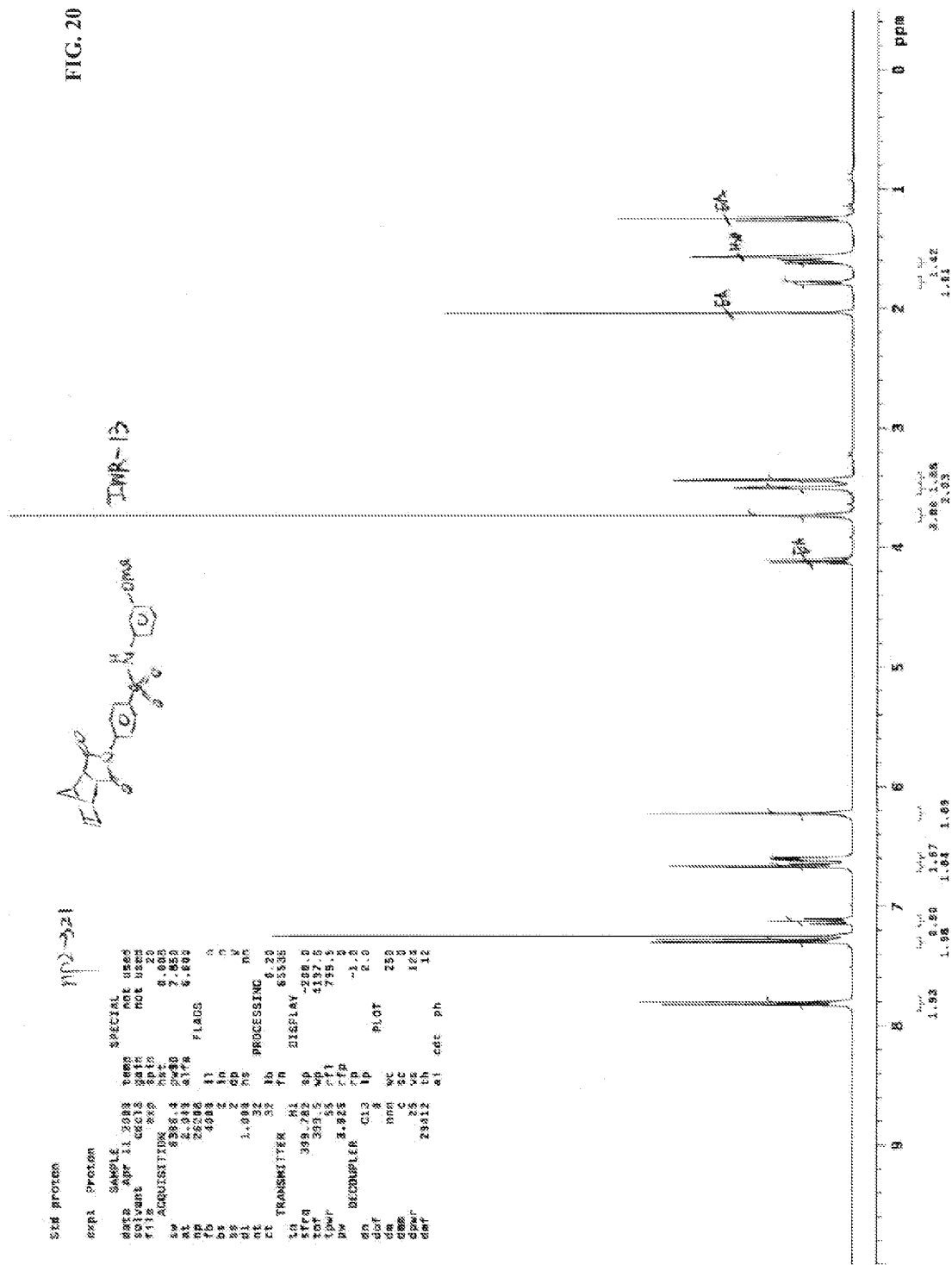
Figure 21:
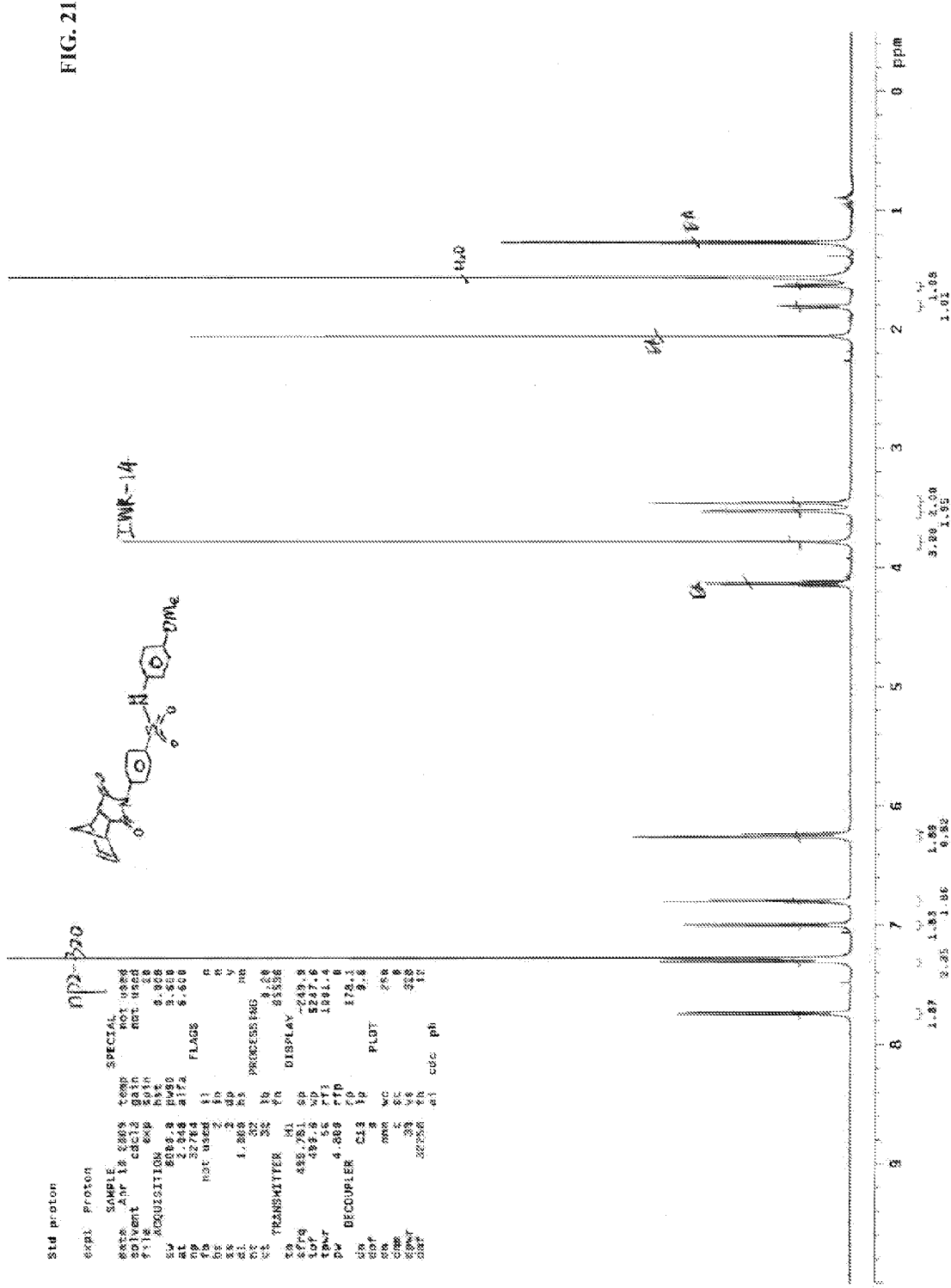
Figure 22:
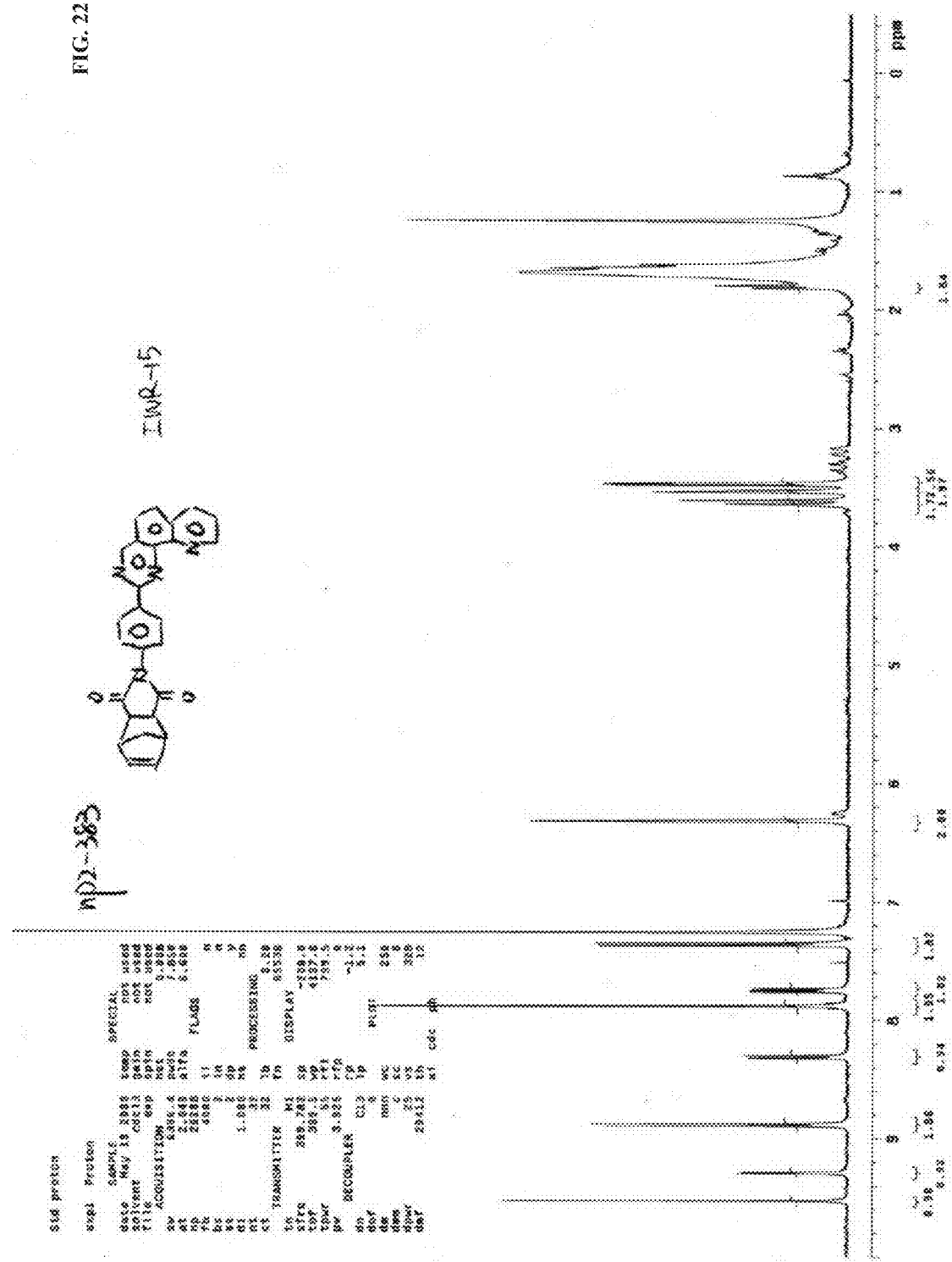
Figure 23:
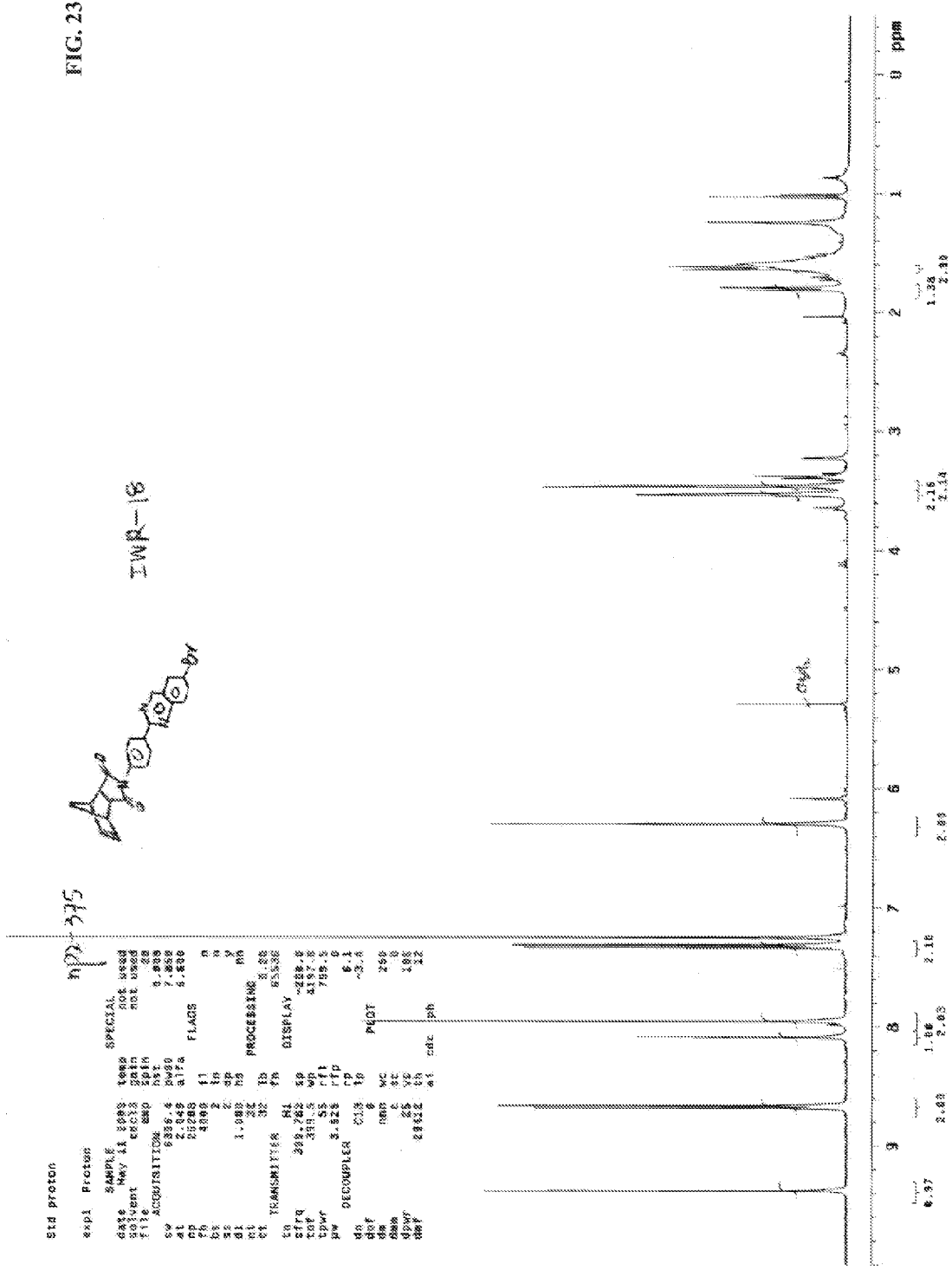
Figure 24:
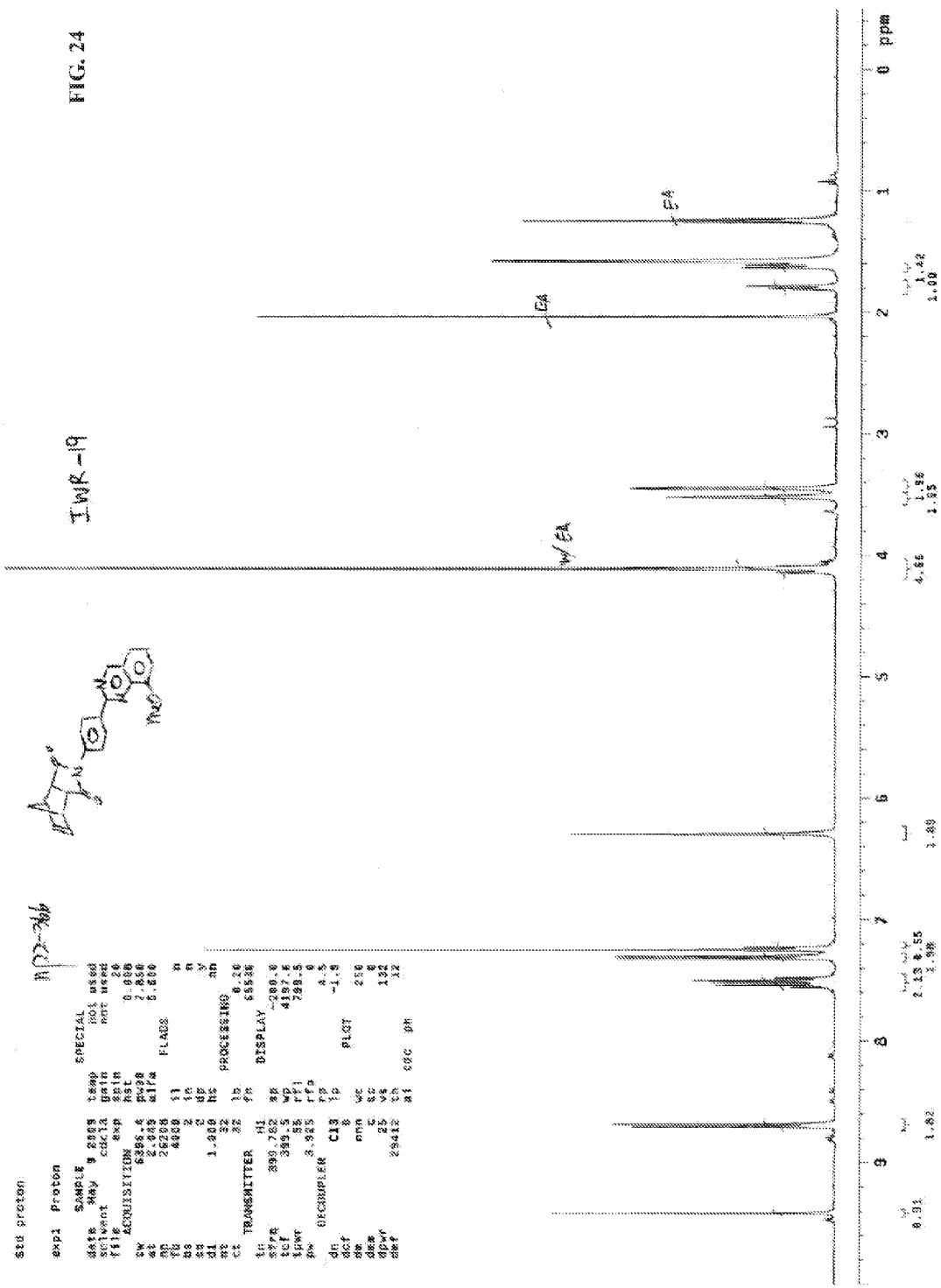

Discussion of Results:

A brief overview of the screen is as follows: mouse L-cells that stably harbor a well-characterized Wnt/β-catenin pathway-responsive firefly luciferase (FL) reporter plasmid (SuperTopFlash or STF), a control reporter, and an expression construct encoding the Wnt protein, Wnt3A, were exposed to individual compounds for two days prior to measurement of reporter activities. Chemicals that altered FL but not control reporter activity were selected for further testing (FIG. 1; FIG. 8). The screening strategy allows for identification of compounds that either potentially increase or decrease Wnt/β-catenin pathway activity.

Several secondary tests were employed in order to further select compounds of interest. These tests were designed to identify especially potent compounds with minimal cellular cytotoxicity ("dose-dependent test") and specificity for attacking the Wnt/β-catenin pathway ("Hh and Notch pathway tests" and "FL inhibitor/protein exocytosis test"; FIG. 1). As the cell-autonomous signalling assay used in the primary screen would be predicted to yield compounds that disrupt either ligand production or response, compounds were identified that retained activity when tested in cells treated with exogenously supplied Wnt protein and that likely function as inhibitors of response. Among those compounds that failed to block Wnt/β-catenin pathway response in this test and that likely block production of Wnt ligand (FIG. 9A), four inhibited Wnt secretion as determined using a Wnt-luciferase fusion protein (FIG. 1 and FIG. 9). Based on the results from these secondary tests, seven compounds were identified that act as inhibitors of Wnt response (IWRs) and four compounds were identified that act as inhibitors of Wnt production (IWPs; FIG. 1).

Figure 3:
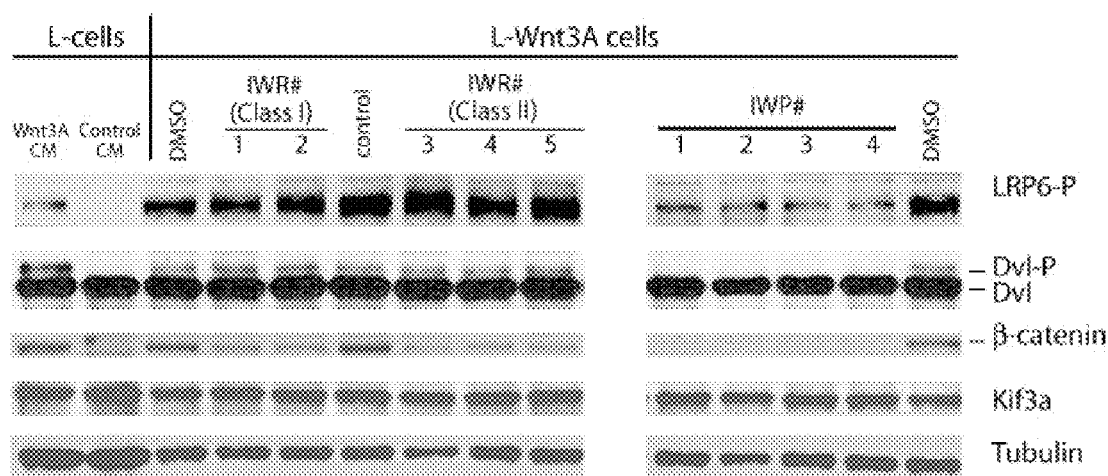
FIG. 3. Biochemical evidence for Wnt/β-catenin pathway inhibition by IWR and IWP compounds. L-Wnt-STF cells that exhibit constitutive Wnt pathway activation were incubated with IWR (10 mM) and IWP (5 mM) compounds for 24 hrs prior to lysis. Cellular lysates were subjected to Western blot analysis to determine levels of LRP6 and Dvl2 phosphorylation, and β-catenin accumulation, all biochemical events associated with Wnt/13-catenin pathway activity. Predictably, IWPs blocked all three biochemical events, whereas IWRs appear to block β-catenin accumulation without affecting LRP6 and Dvl2 phosphorylation. Kif3A and tubulin serve as loading controls. Wild-type L-cells stimulated with exogenous Wnt3A protein provided in conditioned medium exhibit similar biochemical changes in Wnt pathway components as that observed in the L-Wnt-STF cells.

Whereas the IWPs all share the same core chemical structure, two different classes of IWRs could be identified based on structural similarities (FIG. 2A and FIG. 2B). In general, the IWPs are more potent pathway antagonists than those in the strongest class of IWRs (~40 nM vs 200 nM, respectively). Using biochemical markers of Wnt/β-catenin pathway activation, the site of action for each compound was generally localized (FIG. 3). Consistent with their predicted effects on Wnt protein production, IWPs blocked all Wnt-dependent biochemical changes that were assayed (phosphorylation of the LRP6 receptor and Dvl2, and (β-catenin accumulation; FIG. 3). On the other hand, IWR compounds appear to only affect β-catenin levels suggesting they target regulatory events downstream of LRP6 and Dvl2.

Example 3

Synthesis and Characterization

Synthesis of IWR-1, IWP-2, IWR-1-PEG-Biotin, IWP-PEG-Biotin, and IWR-Cy3 were carried out as described in FIG. 12 and FIG. 13. Exemplarary characterization data of some of the compounds disclosed herein is provided below. $^1$H-NMR spectra for compounds IWR-8, 9, 10, 11, 12, 13, 14, 15, 18 and 19 are provided in FIGS. 15-24, respectively.

IWP-1: $^1$H NMR (400 MHz, DMSO-$d_6$) δ 12.42 (br, 1H, NH), 8.98 (t, J=5.9 Hz, 1H, NH), 8.73 (d, J=7.8 Hz, 1H), 8.38 (d, J=7.8 Hz, 1H), 7.99 (dd, J=7.8, 7.6 Hz, 1H), 7.92 (dd, J=7.8, 7.6 Hz, 1H), 7.65 (d, J=8.2 Hz, 2H), 7.63 (d, J=8.5 Hz, 1H), 7.54 (d, J=2.3 Hz, 1H), 7.08 (d, J=8.2 Hz, 2H), 7.02 (dd, J=8.5, 2.3 Hz, 1H), 4.28 (d, J=5.9 Hz, 2H), 3.83 (s, 3H), 3.80 (s, 3H); $^{13}$C NMR (100 MHz, DMSO-$d_6$) δ 179.7, 168.3, 163.7, 158.7, 158.4, 156.2, 155.7, 137.9, 134.3, 133.9, 132.8, 132.3, 128.0, 127.5, 127.3, 126.8, 126.7, 121.2, 114.9, 113.7, 104.7, 55.6, 55.5, 42.4; MS (ES+) calc'd. for $C_{26}H_{22}N_5O_5S$ $(M+H)^+$ 516.1. found 516.1.

IWR-1: $^1$H NMR (400 MHz, CDCl$_3$) δ 10.72 (s, 1H, NH), 8.89 (dd, J=7.3, 1.1 Hz, 1H), 8.81 (dd, J=4.1, 1.2 Hz, 1H), 8.17 (dd, J=8.2, 1.1 Hz, 1H), 8.13 (d, J=8.4 Hz, 2H), 7.56 (dd, J=8.2, 7.3 Hz, 1H), 7.53 (dd, J=8.2, 1.2 Hz, 1H), 7.46 (dd, J=8.2, 4.1 Hz, 1H), 7.37 (d, J=8.4 Hz, 2H), 6.28 (s, 2H), 3.53 (s, 2H), 3.47 (s, 2H), 1.80 (d, J=8.8, 1H), 1.62 (d, J=8.8, 1H); $^{13}$C NMR (100 MHz, CDCl$_3$) δ 176.5, 164.6, 148.4, 138.8, 136.5, 135.2, 134.9, 134.8, 134.5, 128.2, 128.0, 127.5, 126.9, 122.0, 121.8, 116.6, 52.4, 46.0, 45.7; MS (ES+) calc'd. for $C_{25}H_{20}N_3O_3$ (M+H)$^+$ 410.2. found 410.1.

IWR-3: $^1$H NMR (400 MHz, DMSO-$d_6$) δ 8.24 (t, J=6.0 Hz, 1H, NH), 8.09 (dd, J=7.8, 0.4 Hz, 1H), 7.70-7.64 (m, 2H), 7.32-7.19 (m, 9H), 6.92 (d, J=6.9 Hz, 1H), 6.05 (s, 1H), 5.25 (s, 2H), 4.23 (d, J=6.0 Hz, 2H), 3.88 (d, J=6.9 Hz, 2H), 2.90 (s, 3H), 2.16-2.11 (m, 1H), 1.77-1.71 (m, 5H), 1.37-1.28 (m, 2H), 1.09-1.00 (m, 2H); $^{13}$C NMR (75 MHz, CDCl$_3$) δ 175.1, 161.5, 161.2, 160.6, 153.4, 151.0, 143.6, 139.9, 136.9, 135.4, 128.3, 128.2, 127.1, 126.7, 124.5, 123.0, 118.9, 115.1, 114.8, 101.9, 47.2, 46.9, 44.0, 41.8, 35.7, 29.7, 28.9, 24.1; MS (ES+) calc'd. for $C_{33}H_{34}N_5O_4$ (M+H)$^+$ 564.3. found 564.1.

Example 4

Inhibitors of Wnt Production (IWPs) Target the Porcupine Acyltransferase

Figure 4:
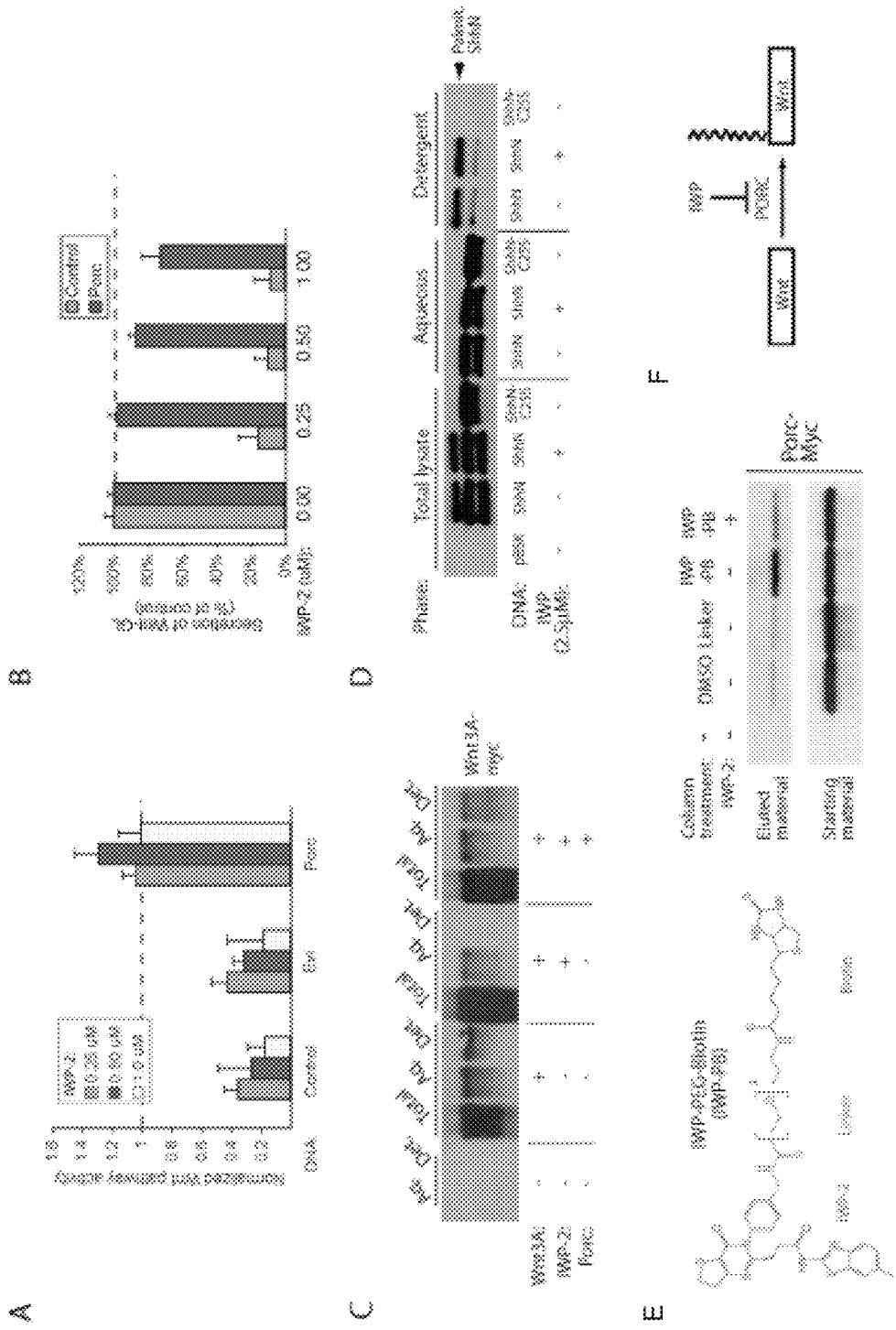
FIGS. 4A-G. IWP compounds target the Porcupine O-acyltransferase.

Tha ability of two genes known to be essential to the production of Wnt ligands were tested, Evenness interrupted (Evi) and Porcupine (Porc), to rescue pathway response in cells treated with an IWP. Expression of Porc but not Evi alleviated the effects of IWP-2 on pathway activity (FIG. 4A) and Wnt secretion (FIG. 4B), suggesting that in general IWPs may act on Porc. Porc, a member of the membrane-bound O-acyltransferase (MBOAT) family, adds a palmitoyl group to Wnt proteins that is essential to their normal function, and is required for Wnt protein transport out of the ER (Takada et al., 2006). Consistent with an inhibition of Porc function by IWPs, the levels of lipidated Wnt3A as measured using a detergent solubility fractionation assay are decreased in IWP-2-treated cells but are unchanged in those cells over-expressing Porc (FIG. 4C). In order to test if Porc interacts with IWP compounds, a biochemical reagent was generated that would allow pull-down of IWP-associated proteins using streptavidin-coated matrix [IWP-PEG-Biotin (IWP-PB); FIG. 4D]. Indeed, specific binding of Porc to IWP-PB was observable (FIG. 4E). Considering the functional and biochemical data together, and without being bound by theory, the simplest model for IWP action is that it directly inhibits the activity of Porc (FIG. 4F). Recent evidence suggests a cytoplasmic acyltransferase controls LRP6 protein maturation by addition of a palmitoyl adduct to residues juxtaposed to the transmembrane sequence (Abrami et al., 2008). Consistent with the specificity of IWPs for Porc and Wnt ligand production, these compounds do not alter cellular response to exogenously supplied Wnt protein (FIG. 9A).

Example 5

Figure 5:
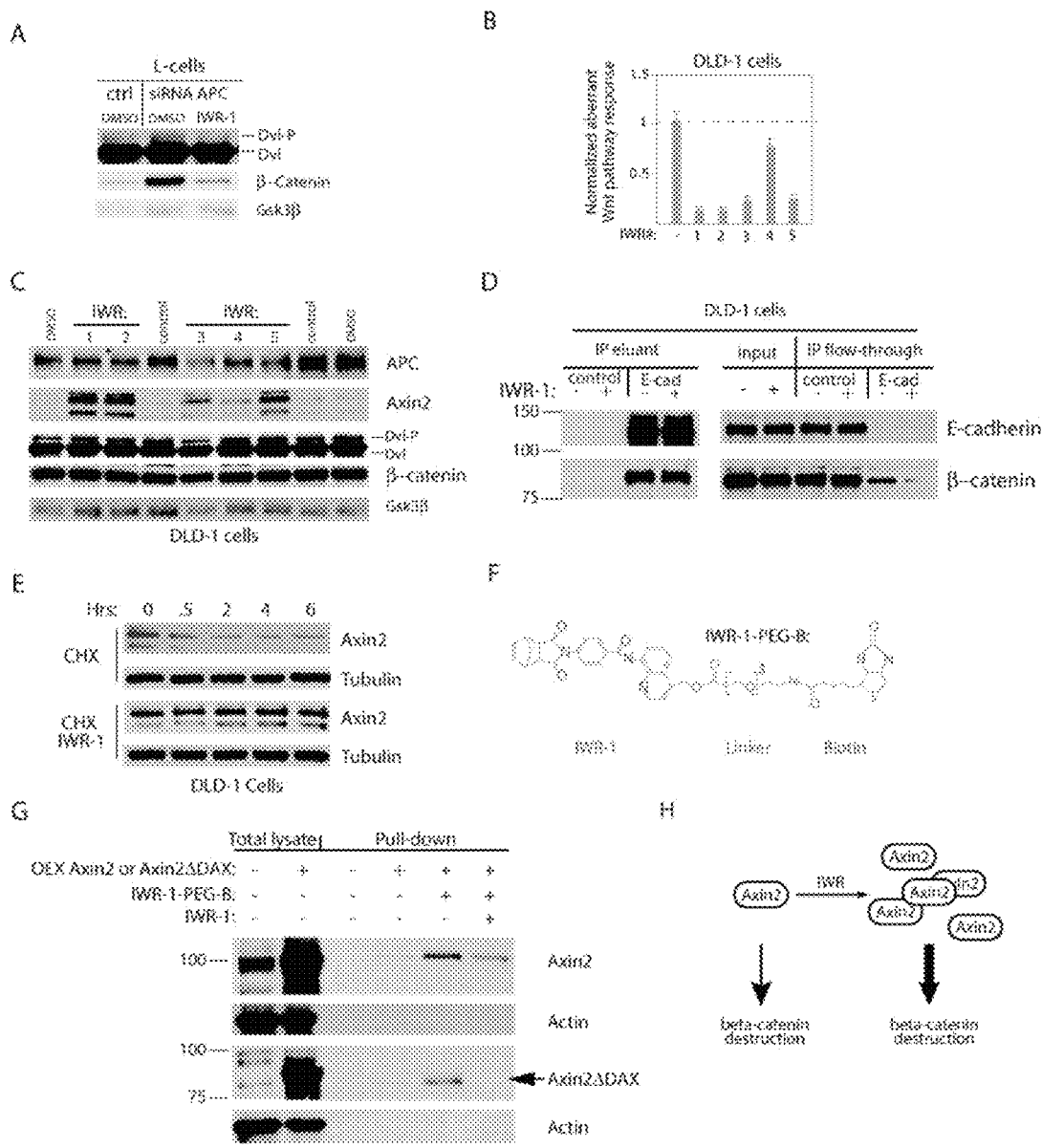
FIGS. 5A-H. Stabilization of the Axin2 destruction complex by IWR compounds.

IWR Compounds Down-Regulate β-Catenin Protein Levels by Stabilizing the Axin2 Destruction Complex Based on biochemical evidence, IWR compounds likely inhibit Wnt-induced accumulation of β-catenin by targeting a pathway component that functions downstream of LRP6 and Dvl2 (see FIG. 3). To further localize their site-of-action, the ability of IWR-1 to block β-catenin accumulation in mouse L-cells treated with siRNAs targeting the APC tumor suppressor was tested (FIG. 5A). The effectiveness of IWR-1 in this context prompted testing of the IWR compounds in colorectal cancer (CRC) cells that frequently harbor loss-of-function mutations in APC (Sjoblom et al., 2006). Indeed, the IWR compounds were able to abrogate to varying degrees aberrant Wnt pathway activity exhibited in DLD-1 cells, a CRC line that expresses a truncated form of APC (FIG. 5B).

The β-catenin destruction complex, which consists of APC, Axin, CK1, and GSK3β, promotes proteasome-mediated proteolysis of phosphorylated β-catenin (Huang and He, 2008). The biochemical effects of IWR compounds on components of this destruction complex in DLD-1 cells and observed an IWR-dependent induction of Axin2 protein with little change in levels of APC or GSK3β (FIG. 5C). Despite this increase in Axin2 protein, a concomitant decrease in β-catenin levels was not observed, as would be expected based on the reporter assay results (see FIG. 5B) and the understanding of Axin2 function. As the majority of β-catenin protein in colonic epithelial cells are sequestered in complexes with the cell-cell adhesion molecule E-cadherin (Orsulic et al., 1999), the pool of "free" β-catenin that is available for Wnt-mediated response was examined. Indeed, levels of β-catenin not bound to E-cadherin are decreased in DLD-1 cells after addition of IWR-1 (FIG. 5D). The induction of Axin2 protein by IWRs does not appear to be dependent upon transcription suggesting these compounds act by stabilizing the protein (FIG. 5E). The effectiveness of the IWR compounds for inhibiting Wnt/β-catenin pathway response can in part be explained by the rate-limiting role that Axin2 occupies in pathway response (Lee et al., 2003).

Interaction of Axin2 with a biotinylated IWR compound in vitro suggests that IWR compounds interact either directly target Axin2 or an Axin2 associated protein (FIG. 5F,G). Without being bound by theory regarding how IWR compounds alter Axin2 protein turnover, the inventors postulate that their effectiveness for inhibiting Wnt/β-catenin pathway response can in part be explained by the rate-limiting role that Axin2 occupies in pathway response (Lee et al., 2003). Taken together, the IWR compounds have revealed a chemically tractable regulatory mechanism within this pathway that could be exploited to control levels of Wnt/β-catenin pathway response (FIG. 5H).

Example 6

Chemical Disruption of the Wnt/O-Catenin Pathway in Regeneration

In order to test the in vivo activity of the identified IWR and IWP compounds, a simple and rapid assay of Wnt/β-catenin pathway activity was pursued—regeneration of the caudal fin in zebrafish (Stoick-Cooper et al., 2007).

Experimental Conditions: Zebrafish Studies.

6 month-old zebrafish were incubated 8 or 14 days at 28.5° C. in aquarium water supplemented with 10 μM IWR or in 0.1% DMSO as a control. Fish were fed standard diet, and solutions were changed daily. At the end of the exposure, zebrafish were incubated in 1 mM BrdU in aquarium water for 2 hrs at room temperature, then washed several times in aquarium water, anesthetized with 0.1% Tricaine, and fixed in 4% paraformaldehyde for 48 hrs at 4° C. The intestine was dissected out, dehydrated, paraffin embedded and sectioned at 5 mm intervals. Sections were stained with Hematoxylin and Eosin or processed for BrdU immunohistochemistry as described (Shepard et al., 2005). Sections from 8 animals each from IWR and DMSO groups were independently scored by four blinded observers. The total number of intestinal folds and total number of BrdU-positive nuclei in the mid and distal sections of the intestine were counted from each section. For caudal fin regeneration assays, zebrafish, 3-6 months of age, were anaesthetized in 0.2% Tricaine and half of the fin was resected using a razor blade to remove. Amputees were reared at 31° C. in tanks containing either 300 ml of water with DMSO or IWR (10 µM). Water and compounds were replenished daily for a total assay period of 4 days.

Discussion of Results:

Whereas the inclusion of IWR-1 in the water of zebrafish suppressed fin regeneration after mechanical resection, addition of IWP-2 failed to do so, suggesting that IWP compounds either have poor bioavailability, or that the determinants in the gene product that they target are not conserved in zebrafish (FIG. 6A). Next, the effects of IWR-1 treatment on maintenance of dividing cells in the zebrafish gastrointestinal (GI) tract, another Wnt-dependent process (Muncan et al., 2007), was examined. An abundance of genetic evidence suggests that the GI tissue in metazoans is particularly sensitive to perturbations in Wnt pathway activity (Clevers, 2006). Consistent with the specific activity of IWR-1 against the Wnt/β-catenin pathway in zebrafish, a decreased number of the bromodeoxyuridine (BrdU)-labeled cells typically found at the base of the intestinal in IWR-1-treated fish (FIG. 6B left, 6C) was found. Fish treated for periods longer than 4 days exhibit lethargy and decreased appetite, which correlates with gross histological changes in the architecture of GI tissue (FIG. 6B, right). Taken together, the ability of IWR-1 to block Wnt/β-catenin pathway-dependent processes in zebrafish suggest the IWR compounds may be similarly useful for in vivo studies in mammals.

Example 7

Chemical Disruption of Wnt Pathway Responses in Cancer

As discussed herein, aberrant Wnt pathway activity, sustained either by genetic changes that result in altered Wnt ligand activity or the function of pathway regulators, has been associated with a broad range of cancers (Clevers, 2006; Polakis, 2007). Many colorectal- and some lung cancer-derived cells harbor molecular changes that result in aberrant activation of Wnt-mediated cellular responses. The DLD-1 cells, like many other CRC cells, harbor a mutation in APC whereas the selected lung cancer cell lines (A549, H1299, H460 cells) have been shown to aberrantly express excessive levels of Porc that contributes to their tumorigenic behavior (Chen et al., 2008; Polakis, 2007). In both instances, aberrant pathway activity can be influenced by inhibition of normal Wnt protein function (Clevers, 2006).

Experimental Conditions: Cancer Cell Growth Studies:

In experiments involving IWR and IWP treatments, cancer cells were seeded into a 24 well format (2.5K cells/well) in the presence of the noted Wnt pathway inhibitors (0.5% DMSO final). Media and compound changed every 24 hours for 5 days. On day 6, ATP levels were quantitated via cell titer glo assay (Promega). In experiments involving siRNA transfections, cells were transfected with 50 nM control, Ctnnbl, or Porcn siRNAs (SMARTPools, Dharmacon) using Effectene transfection reagent (Qiagen) and seeded into a 96 well plate, 7.5K cells/well, in triplicate. After 48 hrs, 2.5K cells were transferred from each well into a six well format. ATP levels were measured 120 hrs later via Cell Titer Glo assay (Promega).

Figure 7:
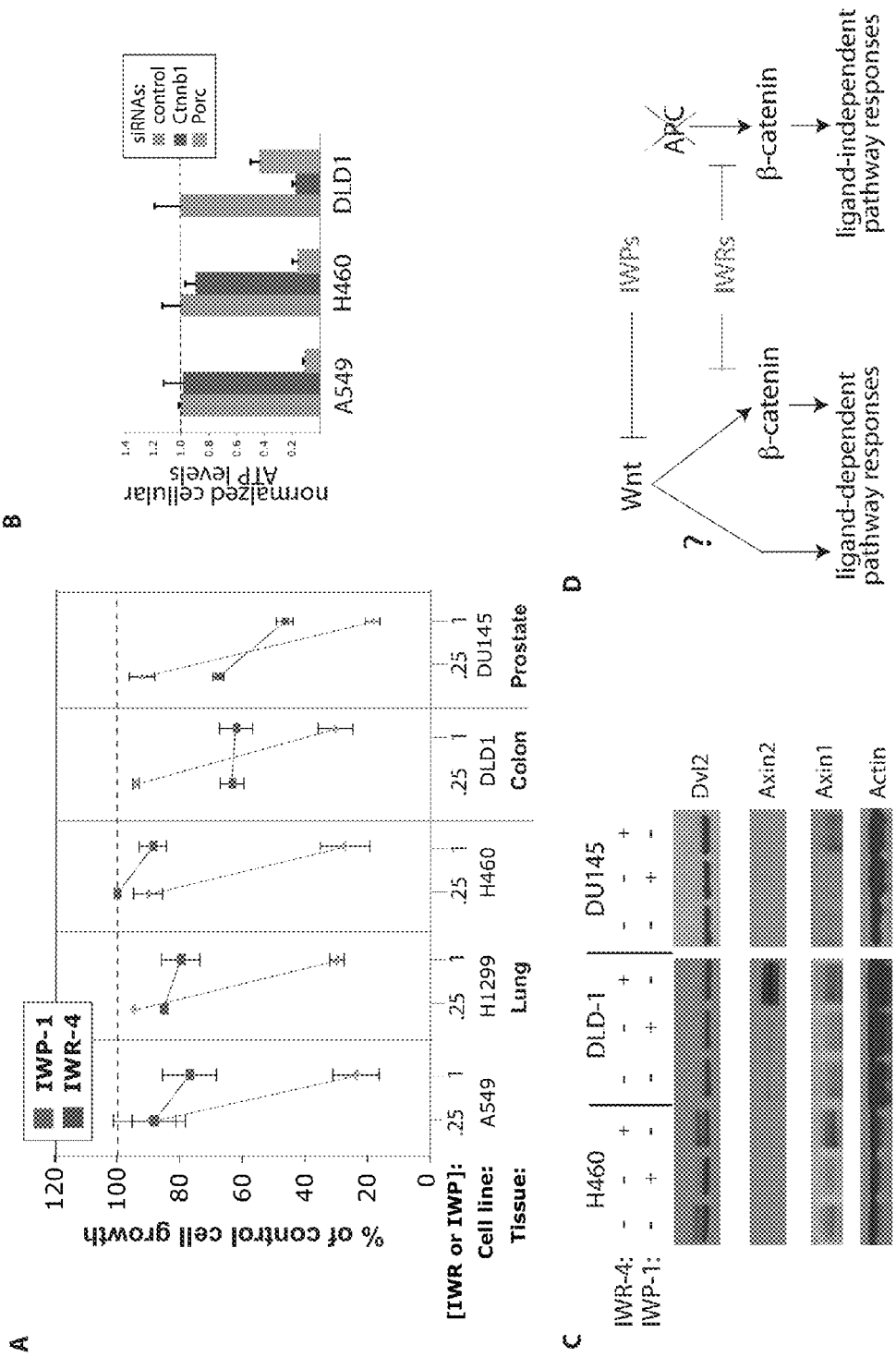
FIGS. 7A-D. Chemical inhibition of Wnt-mediated cellular responses in cancer.

Discussion of Results:

In a growth-sensitivity test of lung cancer and colorectal cancer cells, dose-dependent responses to both IWR and IWP compounds were generally observed (FIG. 7A) that are consistent with chemically-induced biochemical changes in these cells (FIG. 7B). Interestingly, IWP-1 was found to be consistently more effective than IWR-4 at inhibiting cancerous cell growth, likely reflecting the greater potency of IWP compounds in general for inhibiting the pathway (see FIGS. 2,3). Also relevant is the likelihood that IWP but not IWR compounds affect all Wnt pathway responses, including those that are not dependent upon β-catenin (the so called "non-canonical Wnt pathways). Indeed, the Wnt proteins that control these others pathways also appear to be reliant upon Porc for maturation and functionality (FIG. 7C; Kurayoshi et al., 2007). In the case of DLD-1 treated with IWPs, the inventors suspect that that one or more non-Dvl-dependent pathway responses have been inhibited. Currently, little is known about the contribution of these other Wnt pathways to carcinogenesis. Consistent with a role for Wnt pathways that are not dependent upon β-catenin for sustaining growth of both cancer cell lines, treatment of either cell types with Porc siRNAs resulted in loss of cell growth, whereas β-catenin siRNAs mostly influenced the DLD-1 growth behavior (FIG. 7D). Though it is currently not known which "non-canonical" Wnt pathways may be active in these cells, the inventors, without being bound by theory, favor a model whereby the IWR compounds selectively inhibit β-catenin-dependent signalling and the IWP compounds more broadly attack Wnt-mediated cellular responses (FIG. 7E).

All of the methods and apparatuses disclosed and claimed herein can be made and executed without undue experimentation in light of the present disclosure. While the compositions and methods of this invention have been described in terms of preferred embodiments, it will be apparent to those of skill in the art that variations may be applied to the methods and apparatuses and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,843,063
U.S. Pat. No. 5,641,747
U.S. Pat. No. 5,777,193
U.S. Pat. No. 5,806,529
U.S. Pat. No. 6,686,148
U.S. Pat. No. 6,699,873
U.S. Pat. No. 6,833,354
U.S. Pat. No. 6,943,151
U.S. Pat. No. 7,186,683
U.S. Pat. No. 7,241,732
U.S. Pat. RE35,694
U.S. Provisional Patent Appln. 61/130,149
Abrami et al., *Proc. Natl. Acad. Sci. USA*, 105(14):5384-53849, 2008.
Ailles and Weissman, *Curr. Opin. Biotech.*, 18:460-466, 2007.
Barker and Clevers, *Nat. Rev. Drug Discov.*, 5:997-1014, 2006.
Barton-Davis et al., *Proc. Natl. Acad. Sci. USA*, 95:15603, 1998.
Bilic et al., *Science*, 316:1619-1622, 2007.

Brack et al., *Science*, 317:807-810, 2007.
Chen et al., *Oncogene*, 27:3483-3488, 2008.
Chen et al., *Nat. Chem. Biol.*, 5:100-107 2009.
Clevers, *Cell*, 127:469-480, 2006.
Cole et al., *Genes Dev.*, 22:746-755, 2008.
Fevr et al., *Mol. Cell. Biol.*, 27:7551-7559, 2007.
Greene and Wuts, In: *Protective Groups in Organic Synthesis*, 2nd Ed.; Wiley, NY, 1999.
Handbook of Pharmaceutical Salts: Properties, Selection and Use, 2002.
Huang and He, *Curr. Opin. Cell Biol.*, 20(2):119-125, 2008.
Kinzler and Vogelstein, Cell, 87:159-170, 1996.
Korinek et al., *Nat. Genet.*, 19:379-383, 1998.
Kurayoshi et al., *Biochem. J.*, 402:515, 2007.
Lee et al., PLoS Biol., 1:E10, 2003; erratum in *PLoS Biol.*, 2:E89 (2004).
Liu et al., *Science*, 317:803-806, 2007.
Lu et al., *Bioorg. Med. Chem. Lett., Apr.* 18, 2009 (Epub ahead of print).
Lynch, *Exp. Opin. Emerging Drugs*, 9:345, 2004.
March's Advanced Organic Chemistry: Reactions, Mechanisms, and Structure (March's Advanced Organic Chemistry), Smith and March (Eds.), 2001.
Muncan et al., *EMBO Rpts.*, 8:966-973, 2007.
Orsulic et al., *J. Cell Sci.*, 112 (Pt 8):1237-1245, 1999.
Polakis, *Curr. Opin. Genet. Develop.*, 17:45-51, 2007.
Remington's Pharmaceutical Sciences, 18th Ed. Mack Printing Company, 1289-1329, 1990.
Reya and Clevers, *Nature*, 434:843-850, 2005.
Schwarz-Romond et al., *J. Cell Sci.*, 120:2402-2412, 2007.
Shepard et al., *Proc. Natl. Acad. Sci. USA*, 102:13194-13199, 2005.
Sjoblom et al., *Science*, 314:268-274, 2006.
Stoick-Cooper et al., *Development*, 134:479-489, 2007.
Takada et al., *Dev. Cell*, 11:791-801, 2006.
Van der Flier et al., *Gastroenterology*, 132:628-632, 2007.
Veeman et al., *Developmental Cell*, 5:367, 2003.

The invention claimed is:

1. A method of inhibiting Wnt protein signalling in a cell comprising administering to the cell an effective amount of a compound of the formula:

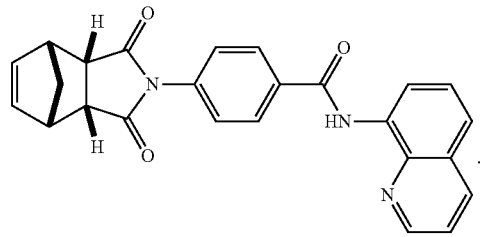

2. The method of claim 1, wherein the cell is in vitro.
3. The method of claim 1, wherein the cell is in vivo.
4. The method of claim 1, wherein the method of inhibiting Wnt protein signalling is further defined as a method of inhibiting Wnt response.
5. The method of claim 1, wherein the method of inhibiting Wnt protein signalling is further defined as a method of inhibiting Wnt protein production.
6. A pharmaceutical composition comprising a pharmaceutically acceptable carrier, diluent, and/or excipient and any one or more of the following compounds:

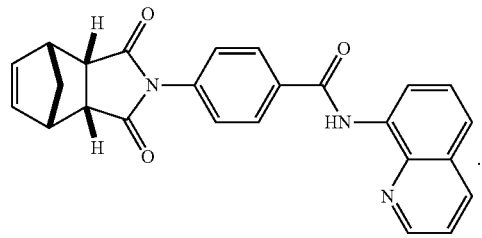

* * * * *